US005837509A

United States Patent [19]
Israelsen et al.

[11] Patent Number: 5,837,509
[45] Date of Patent: Nov. 17, 1998

[54] RECOMBINANT LACTIC ACID BACTERIUM CONTAINING AN INSERTED PROMOTER AND METHOD OF CONSTRUCTING SAME

[75] Inventors: Hans Israelsen, Alleroed; Egon Bech Hansen, Broenshoej; Eric Johansen, Hoersholm; Soeren Michael Madsen; Dan Nilsson, both of Copenhagen; Astrid Vrang, Lyngby, all of Denmark

[73] Assignees: Bioteknologisk Institut, Lyngby; CHR Hansen's Laboratorium Danmark A/S, Hoersholm, Denmark

[21] Appl. No.: 179,557

[22] PCT Filed: Mar. 1, 1994

[86] PCT No.: PCT/DK94/00004

§ 371 Date: Mar. 1, 1995

§ 102(e) Date: Mar. 1, 1995

[87] PCT Pub. No.: WO94/16086

PCT Pub. Date: Jul. 21, 1994

Related U.S. Application Data

[63] Continuation-in-part of Ser. No. 36,681, Mar. 25, 1993, abandoned.

[30] Foreign Application Priority Data

Dec. 30, 1992 [DK] Denmark ................................. 1579/92
Sep. 1, 1993 [DK] Denmark ................................. 0988/93

[51] Int. Cl.$^6$ .......................... C12N 15/11; C12N 15/74; C12N 1/21; C12P 21/02
[52] U.S. Cl. .................... 435/172.3; 435/69.1; 435/71.1; 435/252.3; 435/320.1; 435/853; 536/84.1
[58] Field of Search ................................. 435/172.3, 69.1, 435/71.1, 252.3, 320.1, 853, 854, 855, 856, 857; 536/24.1, 23.1; 935/22, 23, 29, 33, 38, 66, 59, 63, 64, 72

[56] References Cited

U.S. PATENT DOCUMENTS 4,160,038  7/1979  Groben et al. .............................. 426/53
5,340,577  8/1994  Nisbet et al. ......................... 424/93.21

FOREIGN PATENT DOCUMENTS 0 228 726  7/1987  European Pat. Off. .
0 307 011  3/1989  European Pat. Off. .
0 380 823  8/1990  European Pat. Off. .
92/04451   3/1992  WIPO .

OTHER PUBLICATIONS

Berg et al., "Uses of Transposable Elements and Maps of Known Insertions," in Niedart et al., *Escherichia coli and Salmonella typhimurium, Cellular and Molecular Biology*, pp. 1071–1109 (1987).

Berg et al., "Transposable Elements and the Genetic Engineering of Bacteria," in Berg et al, *Mobile DNA*, pp. 879–925 (1989).

Birnboim et al., "A Rapid Alkaline Extraction Procedure for Screening Recombinant Plasmid DNA," *Nucleic Acids Research*, vol. 7, No. 6, pp. 1513–1523 (1979).

Boe et al., "Cloning and Characerization of Two Plasmids from *Bacillus thuringiensis* in *Bacillus subtilis*," *Plasmid*, vol. 25, pp. 190–197 (1991).

Bohall et al., "Transposition of Tn917 in *Bacillus megaterium*," *Journal of Bacteriology*, vol. 167, No. 2, pp. 716–718 (Aug. 1986).

Camilli et al., "Insertional Mutagenesis of *Listeria monocytogenes* with a Novel Tn917 Derivative That Allows Direct Cloning of DNA Flanking Transposon Insertions," *Journal of Bacteriology*, vol. 172, No. 7, pp. 3738–3744 (Jul. 1990).

Chopin et al., "Insertion and Amplification of Foreign Genes in the *Lactococcus lactis* subsp. *lactis* Chromosome," *Applied and Environmental Microbiology*, vol. 55, No. 7, pp. 1769–1774 (Jul. 1989).

DeVos et al., "Molecular Cloning of Lactose Genes in Dairy Lactic Streptococci: The Phospho–β–galactosidase and β–galactosidase Genes and Their Expression Products," *Biochimie*, vol. 70, pp. 461–473 (1988).

Froseth et al., "Molecular Characterization of the Nisin Resistance Region of *Lactococcus lactis* subsp. *lactis* Biovar Diacetylactis DRC3," *Applied and Environmental Microbiology*, vol. 57, No. 3, pp. 804–811 (Mar. 1991).

Gasson et al., "Plasmid Complements of *Streptococcus lactis* NCDO 712 and Other Lactic Streptococci After Protoplast–Induced Curing," *Journal of Bacteriology*, vol. 154, No. 1, pp. 1–9 (Apr. 1983).

Gasson et al., "The Genetics of Dairy Lactic–acid Bacteria," in Davies et al., *Advances in the Microbiology and Biochemistry of Cheese and Fermented Milk*, Ch. 4, pp. 99–126 (1984).

Holo et al., "High–Frequency Transformation, by Electroporation, of *Lactococcus lactis* subsp. *cremoris* Grown with Glycine in Osmotically Stabilized Media," *Applied Environmental Microbiology*, vol. 55, No. 12, pp. 3119–3123 (Dec. 1989).

Klaenhammer "Bacteriocins of Lactic Acid Bacteria," *Biochimie*, vol. 70, pp. 337–349 (1988).

(List continued on next page.)

*Primary Examiner*—Nancy Degen
*Attorney, Agent, or Firm*—Foley & Lardner

[57] ABSTRACT

A method of isolating a lactic acid bacterial DNA fragment comprising a promoter, the method comprising introducing a DNA molecule comprising a transposable element comprising a promoterless structural gene as a promoter probe gene into a population of a lactic acid bacterium, methods of constructing a recombinant lactic acid bacterium comprising a regulatable promoter by using the above method, a recombinant lactic acid bacterium comprising a gene coding for a desired gene product and operably linked thereto a regulatable lactic acid bacterial promoter not natively associated with the gene, the use of such a recombinant lactic acid bacterium and recombinant plasmids comprising a regulatable lactic acid bacterial promoter.

71 Claims, 17 Drawing Sheets

OTHER PUBLICATIONS

Kok, "Genetics of the Proteolytic System of Lactic Acid Bacteria," *FEMS Microbiology Reviews*, vol. 87, pp. 15–42 (1990).

Kok et al., "Construction of Plasmid Cloning Vectors for Lactic Streptococci Which Also Replicate in *Bacillus subtilis* and *Escherichia coli*," *Applied and Environmental Microbiology*, vol. 48, no. 4, pp. 726–731 (Oct.

Le Bourgeois et al., "Genome Comparison of Lactococcus Strains by Pulsed–Field Gel Electrophoresis," *FEMS Microbiology Letters*, vol. 59, pp. 65–69 (1989).

Mayo et al., "Molecular Cloning and Sequence Analysis of the X–Prolyl Dipeptidyl Aminopeptidase Gene From *Lactococcus lactis* subsp. *cremoris*," vol. 57, pp. 38–44 (Jan. 1991).

Nardi et al., "Cloning and DNA Sequence Analysis of an X–Prolyl Dipeptidyl Aminopeptidase Gene From *Lactococcus lactis* subsp. *lactis* NCDO 763," *Appl. Environ. Microbiol.*, vol. 57, pp. 46–50 (1991).

Perkins et al., "A Physical and Functional Analysis of Tn917, a Streptococcus Transposon in the Tn3 Family That Functions in Bacillus," *Plasmid*, vol. 12, pp. 119–138 (1984).

Sanders, "Phage Resistance in Lactic Acid Bacteria," *Biochimie*, vol. 70, pp. 411–422 (1988).

Sanders et al., "A Method for Genetic Transformation of Nonprotoplasted *Streptococcus lactis*," *Applied and Environmental Microbiology*, vol. 53, No. 8, pp. 1730–1736 (Aug. 1987).

Shaw et al., "Complete Nucleotide Sequence of Macrolide–Lincosamide Streptogramin B–Resistance Transposon Tn917 in *Streptococcus faecalis*," *Journal of Bacteriology*, vol. 164, No. 2, pp. 782–796 (Nov. 1985).

Tomich et al., "Properties of Erythromycin–Inducible Transposon Tn917 in *Streptococcus faecalis*," *Journal of Bacteriology*, vol. 141, pp. 1366–1374 (1980).

Tanskanen et al., "Pulsed–Field Gel Electrophoresis of SmaI Digests of Lactococcal Genomic DNA, a Novel Method of Strain Identification," *Applied and Environ. Microbiology*, vol. 56, No. 10, pp. 3105–3111 (1990).

Belkum et al., "Organization and Nucleotide Sequences of Two Lactococcal Bacteriocin Operons," *Applied and Environmental Microbiology*, vol. 57, No. 2, pp. 492–498 (Feb. 1991).

Vandeyar et al., "Chromosomal Insertions of Tn917 in *Bacillus subtilis*," *Journal of Bacteriology*, vol. 167, No. 2, pp. 530–534 (Aug. 1986).

Youngman, "Plasmid Vectors for Recovering and Exploiting Tn917 Transpositions in Bacillus and Other Gram–positive Bacteria," in Hardy, *Plasmids: A Practical Approach*, pp. 79–103 (1987).

Youngman et al., "Methods for Genetic Manipulation, Cloning, and Functional Analysis of Sporulation Genes in *Bacillus subtilis*," in Smith et al., *Plasmids: A Practical Approach*, Ch. 3, pp. 65–87 (1989).

Youngman et al., "Genetic Transposition and Insertional Mutagenesis in *Bacillus subtilis* with *Streptococcus faecalis* Transposon Tn917," *Proc. Natl. Acad. Sci. USA*, vol. 80, pp. 2305–2309 (Apr. 1983).

Youngman et al., "New Ways to Study Developmental Genes in Spore–Forming Bacteria," *Science*, vol. 228, pp. 285–291 (Apr. 1985).

Romero et al., "IS946–Mediated Integration of Heterologous DNA into the Genome of *Lactococcus lactis* subsp. *lactis*," *Applied and Environmental Microbiology*, vol. 58, No. 2, pp. 699–702 (Feb. 1992).

Koivula et al., "Isolation and Characterization of *lactococcus lactis* subsp. *lactis* Promoters," *Applied and Environmental Microbiology*, vol. 57, No. 2, pp. 333–340 (Feb. 1991).

Hill et al., "Development of High–Frequency Delivery System for Transposon Tn919 in Lactic Streptococci: Random Insertion in *Streptococcus lactis* subsp. *diacetylactis* 18–16", *Applied and Environmental Microbiology*, vol. 53, No., 1, pp. 74–78 (Jan. 1987).

Rausch et al., "Characterization of the Novel Nisin–Sucrose Conjugative Transposon Tn5276 and Its Insertion in *Lactococcus lactis*," *Journal of Bacteriology*, vol. 174, No. 4, pp. 1280–1287 (Feb. 1992).

Steen et al., "Characterization of the Nisin Gene as Part of a Polycistronic Operon in the Chromosome of *Lactococcus lactis* ATCC 11454," *Appl. and Environ. Microbiology*, vol. 57, No. 4, pp. 1181–1188 (1991).

Israelsen et al., "Insertion of Transposon Tn917 Derivatives into the *Lactococcus lactis* subsp. *lactis* Chromosome," *Applied and Environmental Microbiology*, vol. 59, No. 1, pp. a–f (Jan. 1993).

Bruinenberg et al., "Proteinase Overproduction in *Lactococcus lactis* Strains: Regulation and Effect on Growth and Acidification in Milk," *Applied and Environmental Microbiology*, vol. 58, No. 1, pp. 78–84 (Jan. 1992).

Hahn, et al., "Tn5099, a xyIE Promoter Probe Transposon for Streptomyces spp." J. Bacteriol., vol. 173(17):5573–5577.

ATCC Catalogue of Bacteria & Bacteriophages, (1992):176–177.

Van der Vossen, et al., "Isolation and Characterization of *Streptoccocus cremoris* Wg2–Specific Promoters", Applied and Environmental Microbiology, vol. 53, No. 10, Oct. 1987, pp. 2452–2457.

Simons, et al., "Construction of a Promoter–Probe Vector for Lactic Acid Bacteria Using the IacG Gene of *Lactococcus lactis*", Developments in Industrial Microbiology, vol. 31, No. 5, 1990, pp. 31–39.

Alexieva, Z. et al., "Chloramphenicol Induction of cat–86 Requires Ribosome Stalling at a Specific Site in the Leader", *Proc. Natl. Acad. Sci. USA*, vol. 85, pp. 3057–3061 (May 1988).

Beresford, T. et al., "Physiological and Genetic Regulation of rRNA Synthesis in Lactococcus", Journal of General Microbiology, vol. 139, pp. 2009–2017 (1993).

Bhowmik, T. et al., "Development of an Electroporation Procedure for Gene Disruption in *Lactobacillus helveticus* CNRZ 32", *Journal of General Microbiology*, vol. 139, pp. 1433–1439 (1993).

Bojovic, B. et al., "Improved Vector for Promoter Screening in Lactococci", *Applied & Environmental Microbiology*, pp. 385–388 (Feb. 1991).

Chiaruttini, C., et al., "Gene Organization, Primary Structure and RNA Processing Analysis of a Ribosomal RNA Operon in *Lactococcus lactis*", *J. Mol. Biol.*, vol. 230, pp. 57–76 (1993).

David, S., "*Leuconostoc lactis* β–Galactosidase is Encoded by Two Overlapping Genes", *Journal of Bacteriology*, vol. 174, pp. 4475–4481 (Jul. 1992).

Hanahan, D., "Studies on Transformation of *Escherichia coli* with Plasmids", *J. Mol. Biol.*, vol. 166, pp. 557–580 (1983).

Henkin, T. M. et al., "Mutations in the Spacer Region of a *Bacillus Subtilis* Promoter", *Genetics and Biotechnology of Bacilli*, vol. 2, pp. 63–67 (1988).

Jahns, A. et al., "Identification, Cloning and Sequencing of the Replication Region of *Lactococcus lactis* ssp. *lactis* biovar. diacetylactis Bu2 citrate Plasmid pSL2", *FEMS Microbiology Letters* 80, pp. 253–258 (1991).

Jinks–Robertson, S. et al., "Ribosomes and tRNA", Cellular and Molecular Biology, pp. 1358–1385 (1987).

Johansen, E. et al., "Characterization of *Leuconostoc* isolates from Commercial Mixed Strain Mesophilic Starter Cultures", *J. Dairy Sci.*, vol. 75, pp. 1186–1191 (1992).

Johansen, E., et al., "Isolation and Characterizaton of IS1165, an Insertion Sequence of *Leuconostoc mesenteroides* subsp. *cremoris* and Other Lactic Acid Bacteria", *Plasmid*, vol. 27, pp. 200–206 (1992).

Kiewiet, R. et al., "The Mode of Replication is a Major Factor in Segregational Plasmid Instability in *Lactococcus lactis*", Applied and Environmental Microbiology, vol. 59, pp. 358–364 (1993).

Leenhouts, K. J. et al., "Campbell–Like Integration of Heterologous Plasmid DNA Into the Chromosome of *Lactococcus lactis* subsp. *lactis*", *Applied & Environmental Microbiology*, vol. 55, pp. 394–400, (Feb. 1989).

Macrina, F. L. et al., "Novel Shuttle Plasmid Vehicles for Escherichia–Streptococcus Transgeneric Cloning", *Gene*, vol. 25, pp. 145–150 (1983).

Marsh, J. L. et al., "The pIC Plasmid and Phage Vectors with Versatile Cloning Sites for Recombinant Selection by Insertional Inactivation", *Gene*, vol. 32, pp. 481–485 (1984).

Nilsson, D. et al., "Isolation of Purine Auxotrophic Mutants of *Lactococcus lactis* and Characterization of the Gene hpt Encoding Hypoxanthine Guanine Phosphoribosyltransferase", *Mol. Gen. Genet.*, vol. 235, pp. 359–364 (1992).

Nygaard, P., "Utilization of Preformed Purine Bases and Nucleosides", *Metabolism of Nucleotides, Nucleosides and Nucleobases in Microorganisms*, pp. 27–93 (1983).

Ogasawara, N. et al., "Structure and Organization of rRNA Operons in the Region of the Replication Origin of the *Bacillus Subtillis* Chromosome", *Nucleic Acids Research*, vol. 11, pp. 6301–6318 (1983).

O'Sullivan, D. J. et al., "Rapid Mini–Prep Isolation of High–Quality Plasmid DNA from Lactococcus and Lactobacillus spp.", *Applied and Environmental Microbiology*, vol. 59, pp. 2730–2733 (1993).

Pedersen, M. L. et al., "Genetic Analysis of the Minimal Replicon of the *Lactococcus lactis* subsp. *lactis* biovar *diacetylactics* Citrate Plasmid", *J. Bacteriol.*, pp. 1–22 (1993).

Youngman, P., "Plasmid Vectors for Recovering and Exploiting Tn917 Transpositions in Bacillus and Other Gram–Positive Bacteria", *Plasmids: A Practical Approach*, pp. 79–103 (1987).

Youngman, P. et al., "Methods for Genetic Manipulation, Cloning, and Functional Analysis of Sporulation Genes in *Bacillus Subtilis*", *Regulation of Procaryotic Development*, pp. 65–87 (1989).

Youngman, P. et al., "New Ways to Study Developmental Genes in Spore–Forming Bacteria", *Science*, 228, vol. 228, pp. 285–291 (1985).

van der Vossen, J. M. B. M. et al., "Construction of Cloning, Promoter–Screening, and Terminator–Screening Shuttle Vectors for *Bacillus subtilis* and *Streptococcus lactis*," *Applied and Environmental Microbiology*, vol. 50, pp. 540–542 (Aug. 1985).

Sibakov et al., "Secretion of TEM β–Lactamase with Signal Sequences Isolated from the Chromosome of *Lactococcus lactis* subsp. *lactis*", *Applied and Environmental Microbiology* 57:341–348 (1991).

FIG. 12

```
     <tma                                                                                                          -44
  1  ACAGATTCTAAACCAGAAGAGAAATAAGGAAAAATCAGAAGATGAAACAGCCGAATAAGGCTGTGTTTTCTTTTTTTTATGTTTAGAATAAGTGGTCTAGT
      T  D  S  K  P  E  E  N  K  E  K  S  E  D  E  T  A  E  *
         -35                    PI       -10    stringent
                                         PII
                                                                  -44               stringent
 101 TTATTCTTGACAAAAATAATATATTTGATATAATTAAATAGTGTCGTTTGAGACGACTGACTTCTCTTATTATTCATCTAAAATATTATTTGAAAAGAT
        -35           PI         -10     stringent
                      PII
                                                                                                  gluT
 201 AACACAGTTTATTCTTGACAAAAATATAAAAGTGTATAATAGAAAAAGTACTGTTTGAGACAGCACAACAATATATGGTCCGTTGGTCAAGGGGTTAAG
                                                            ScaI
                                                                          serI
 301 ACACCGGCCTTTTCACGGGCGTAACACGGGTTCGAATCCCGTACGGACTATATCTGGAGGATTACCCAAGTCCGGCTGAAGGGAACGGTCTGAAAACCGT metI
 401 CAGGCGTGTAAAAGCGTGCGTGGGTTCGAATCCCACATCCTCCTTTTTAATTATCGCGGGATGGAGCAGTAGGTAGCTCGTCGGGCTCATAACCCGAAG pheI
 501 TCATAGGTTCAAATCCTATTCCCGCAATTTGGCTCGGTAGCTCAGTTGGTAGAGCAATGAAGCTCCATGTGCGGGTTCGATTCCGTCGTCTCGC
                   glyT
 601 GCCATTCCTTATTAGCGGATGTAGTTAATGGTAGAACCCCAGCCTTCCAAGCTGGTACGCGAGTTGCATTCTCGTCATCCGCTTAACTTAATATTT
     ileT                                                               rrfU
 701 GGGAGTTAGCTCAGTTGGTTAGAGCACTGTGTTGATAACCGCAGGGGTCCCAGGTTCGAATCCTGGAATTCCCATATTTGGTATTTATTGCATAGGAGAT asnT
 801 ATACCTGTCCATGTCGAACACAGAAGTCAAGTCCTTTTGCGCTGGAAGTACTTGGGGGTTGCCCCTGGGAGATAAAGACGATGCCAAGTTTACATTG SpeI
 901 CGGATTAGCTCAGTTGGTAGTAGCGCATGACTGTTAATCATGATGTCGTCAGTTCGAGTCTGACATCCGCAGTAACTAAGGGTGACTTTT 1001 TTATTTTATAAATATTATCAATAAATCTTGGCACGCCTTTTTGTGTCAAGATTTTTATTTACAGCTTTATTGGTAGCGGTTACAATATAATTATACTAGT
```

FIG. 13

```
          -44                -35                            -15      -10          Stringent
A    AGAATAAGTGGTCTAGTTTATTCTTGACA..AAAAATAATATATTTGATATAATTAAATA.GTTGTCGTTT
B    TGAAAGATAACACAGTTTATTCTTGACA..AAAAAATATAAAAGTG.TATAATAGAAAA.GTACTGTTTG
C    ATCAGTGATTATGAGTTTTTTCTTGACAGAAGAAGGCGAAAAATGGTATTATATTTAG..GTACTGTTTT
D    ATCAGTGATTATGAGTTTTTTCTTGACAGAAGAAGATGGCGAAAAATGGTATTATATCTAG..GTACTGTTTT
E    CTTGAAATAAATAAGTTAAAACTTGAAA.TTTATGAGGGTTTTTGGTAAAATATTTCTTGTCGTCATCA
F    TTTTGCATGTAATGAGTTTATTCTTGACA.ACTTTTGGGAAACTTGGTATACTTGGTATACTAATATA.GTCGTTTAAG
G    GGTATAAAAGTCACAGTTAATTCTTGACA.AGTTTAGTTAGGTTTGATAGAATATAATA.GTTGTCGCAA
H    ACCTAAAAATTGACAGTTAATTCTTGACA.GGGAGAGATAGGTTTGATAGAATATAA...GTTGTCACGA Con.              AGTT....CTTGA.A............TG.TA...T......GT..T....

I    TAGTTATTCTTATTCATATTATTCAGG.AAGGTAATTAACTATGGTATAATGAAATTAGATAAGGGA

J    TATCCTATTAATCAAGTTGAC.CTTGAAA.AAAAACTGAAAATCTGTTATCATAAATAATGGACATTTT
```

```
  1 GATCATCTACAATCATTAAAGTTTATCAAAGAGCCGAAGATAGTTCTCAGATTCTCGGTGGATAATCCATCATCAATTGTGCCGAGGTTTGGATAAGATTC   100
101 TAAAACAGTATAAATATTTTACCATAGACGAAAAGGGGTCTTGCCACGTTTCTCATTTGCTGGAAAATAATTTCAAGGCTTGCTTTATCAATAAGT       200
201 TCTGCAAAAAGTGCTTCTTTACTTGAAAATGGTAGTAAAGAGAAGACACTGTCATTCCTACGGCACTAGCTAACTTACGCATTGAAAATTCTGTGAGAG   300
301 TAAGTTCTCTAAAAGTTCCCAGCTGCTACTAATAATTTTATCTTGGTTGGTTGAGTCGCCATAAGTTTTCGCTTTCTTTTCTACTTAGATTTATTT       400
401 ACATGTTTTTAATGAAAATTGCGATAGAAAAGCTGATAAACAAATTTGTCATTTAAATATTGTAAGGGAAAACTCTAGCTATAATTGAGTAAATACCGA   500
501 ACAATCTCTCTTCTTATTTCTTGAAACTTTTGTTCAGGCTTTTTCTTTTATCACACAAATCTTTAAGATAGAATTATAAGATTTATAAAGCAAGAAAAGAT 600
601 AGATGAGCTATCGTCACTTTGACTTTATTATTCGTTCAAGATTTGTTGAATAATAAAATAGCTGAATACACAAGTCTGTGTATATAAAAGCGTT       700
701 TGGGAATATCGGAGAAATGATGAAAATTTGGTAATTGGTTCTGGCGGCCGAACATGCCTAGCAAAAAAATTTATGGAAAGTCCTCAAGTTGAAGAA      800
                                      .RBS                           M  K  I  L  V  I  G  S  G  G  R  E  H  A  L  A  K  K  F  M  E  S  P  Q  V  E  E
                                                                    PurD-->
                                                                                                                                                   .EcoRI
801 GTCTTTGTAGCTCCAGGCAATTCAGGAATGAAGAAAAAGATGGAATTC  846
    V  F  V  A  P  G  N  S  G  M  E  K  K  D  G  I
```

FIG. 14

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TGAATTCAGA GGTTTGATGA CTTTGACC         28

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGAATTCCTA ACAAAAGACT ATTAACGC         28

( 2 ) INFORMATION FOR SEQ ID NO:3:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ATAGATCTGC AGGATCCCGG GTAACTTTGA AAGGATATTC CTC         43

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ATTGAGGGTA TACGGTGGGC G         21

( 2 ) INFORMATION FOR SEQ ID NO:5:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AAGCTTTCGC GAGCTCGAGA TCTGCAGGAT CCCGGGTAAC TTTGAAAGGA TATTCCTCAT         60

G         61

( 2 ) INFORMATION FOR SEQ ID NO:6:

( i ) SEQUENCE CHARACTERISTICS:
        ( A ) LENGTH: 12 base pairs
        ( B ) TYPE: nucleic acid ( C ) STRANDEDNESS: single
        ( D ) TOPOLOGY: linear ( x i ) SEQUENCE DESCRIPTION: SEQ ID NO:6:

GGGTCTAGAT TA                                                                                    12

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TAATCTAGAC CC                                                                                    12

( 2 ) INFORMATION FOR SEQ ID NO:8:

( i ) SEQUENCE CHARACTERISTICS:
        ( A ) LENGTH: 73 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:8:

AAGCTTTCGC GAGCTCGAGA TCTGCAGGAT CCCGGGTCTA GATTAGGGTA ACTTTGAAAG                                 60

GATATTCCTC ATG                                                                                   73

( 2 ) INFORMATION FOR SEQ ID NO:9:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GATCGCCATC GATGGC                                                                                16

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GATCGCCATC GATGGC                                                                                16

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GTTAAATGTA CAAAATAACA GCG                                                                        23

( 2 ) INFORMATION FOR SEQ ID NO:12:

( i ) SEQUENCE CHARACTERISTICS:
        ( A ) LENGTH: 23 base pairs
        ( B ) TYPE: nucleic acid (C) STRANDEDNESS: single
(D) TOPOLOGY: linear (x i) SEQUENCE DESCRIPTION: SEQ ID NO:12:

CCAGTCAACT TTAAAACATA ACC      23

(2) INFORMATION FOR SEQ ID NO:13:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (x i) SEQUENCE DESCRIPTION: SEQ ID NO:13:

CTCACTGGTC ACCTTTATCC      20

(2) INFORMATION FOR SEQ ID NO:14:

(i) SEQUENCE CHARACTERISTICS:
  (A) LENGTH: 1185 base pairs
  (B) TYPE: nucleic acid
  (C) STRANDEDNESS: single
  (D) TOPOLOGY: linear (x i) SEQUENCE DESCRIPTION: SEQ ID NO:14:

| | | | | | |
|---|---|---|---|---|---|
| CTGGTCACCT | TTATCCATTG | AAAATTGATA | ACAAAGGATT | ACAAGTAGAA | GAATCTGTAT | 60 |
| TTTAATACAG | GTTCTTTTTG | TTGATTATTT | TATAGATAAA | ATGATATAAT | CATTAAAGCA | 120 |
| AAAAGAATG | TAAAGTAGTT | CACTAACTTT | CGTTTTATTT | GTCAGAATAA | GGTTTTTGAT | 180 |
| TTATCATTTT | TTTAAAGTTA | AAAGTAATGA | ATTATTAAAT | TTCTTCTAAT | GACAAAAAAT | 240 |
| GTGATTTAAA | TGAGAAACCA | CGATTGCCCT | ACTGTCCGCT | TTTTAAAGC | AAGAGTTTAT | 300 |
| AAAGAAAAGG | AAACTCAAAT | GACTCAAACA | AAAAAGGCAA | AAGTCAGAAA | TCTGATTATT | 360 |
| GCTGCGATGC | TTACTGCACT | TGGAATTTTA | ATTCCAATGA | TGATGCCGGT | TAAACTCATT | 420 |
| ATTGGCCCAG | CCTCATTCAC | GCTTGCTGCA | CATGTTCCGG | TAATGGCTGC | CATGTTTTC | 480 |
| AGTCCACTTA | TGACTGCTTT | TGTTGCTCTG | GGAACAACTC | TCGGATTCAT | GATTAGTATT | 540 |
| CCGGTGCCAA | CAATTTGGTT | GCGCGCGCTG | ATGCACCTTC | CTGTAATGAC | TGTTGGTGCC | 600 |
| TATGTCTTGA | AAAAATATCC | AGAATTTGTT | CATCAAAAAG | TTAAAATCCA | AATCTTTAAT | 660 |
| TTTATTCTCG | GTATTTTTCA | TGCTGGTTTG | GAAACTTTAG | TTGTTTATGC | TTTTTATTCT | 720 |
| CTAGGATTTG | CGAATATTGA | GCAAGGTGCT | TTATTGAACT | TCCTCTTATT | GATTGCTCTT | 780 |
| GGAGGACTTG | TCCATAGCAT | GATTGACTTC | AACTTAGCGC | TTGGTTTGGG | TAATGTTTTG | 840 |
| AGTAAAGCCT | TTCCTATTGA | CATCTTTGAT | AAAGCTAAAA | ATCTTGTGAA | TAAAAAGAAA | 900 |
| GTTAAAGCCG | AAATTTAAGA | CAAAATTGTC | ATCTTTAATA | GAAAATGATA | AATAAGGTT | 960 |
| ATGATAAAAG | AAACTGATCT | TGAAAATATC | CCAGATTTAC | TGATTAAATT | TAATGAACCC | 1020 |
| CTATCAAATT | ATACTTACAC | AAAAGTAGGA | GGACCAGCTG | ATATTCTGGC | TTTTCCGGCT | 1080 |
| ACAATAGAAG | CATTGACAGA | ACTGTCAGCA | AAAGCGAACA | GACTGATACA | CCGGTTACAG | 1140 |
| TTCTTGGAAA | TGCCTCAAAT | TTGATTGTTC | GTGATGGTGG | AATTC | | 1185 |

(2) INFORMATION FOR SEQ ID NO:15:

(i) SEQUENCE CHARACTERISTICS:
  (A) LENGTH: 1430 base pairs
  (B) TYPE: nucleic acid
  (C) STRANDEDNESS: single
  (D) TOPOLOGY: linear ( x i ) SEQUENCE DESCRIPTION: SEQ ID NO:15:

| | | | | | | |
|---|---|---|---|---|---|---|
| CATCATTTAT | TTCAAAGTAT | AAAAAAAATC | AATGGAAAAG | TTGTATGGAT | TAATATCAGT | 60 |
| TTTCTTTTCG | TATTATCACT | AATTCCTATT | TTTCAAACT | GGGTATCAAT | ATATCCCAAT | 120 |
| TCATTTATTC | CAGAACTAGG | TTATGTCATT | ATCTTTTCT | TTGGAAACTT | CATCTACTTT | 180 |
| CTATTAACAA | GGGAATTATT | AAAATTAAT | GGTCACCGTA | AAACTTCTGA | ATCAACTGTA | 240 |
| AGAAAAAATA | TCATCAGTGT | TGGACTTAAT | GTCATTAGCA | TTATTCTTGG | ATATTTATT | 300 |
| GCACCGGTGA | TTATGCTCAT | TGCTTCGGCG | TTGATTTTT | CAATGTGGGT | CATTCCAGAT | 360 |
| AAGAACATTG | AAAAAATGTT | TAAATAAGTA | TTTTATAAAA | ATAGAATTTG | TATCAAGAAA | 420 |
| AATTTGGAAA | AACTGACTAA | ATTGTCTGTC | AGTAAATTAA | ATATAAATTG | AGGAGAAAAT | 480 |
| AATGATTAAA | GCATACATTA | AATATTGGAA | AAAAGCAGGC | GATTTCAAAA | CATATTCAAG | 540 |
| TCGTTCAGAT | TACTGGTGGG | TTTTCTTGGC | GAATTTCATT | ATCTTTGCTA | TTCTAAGCTT | 600 |
| TTTTAATTTT | ATGATTATGA | TACCAAGAGC | TGCCAAAATC | ATGAATCAAG | CAGGTGACTC | 660 |
| ATCTCAAACA | GAAATCATTC | GACAAGTCAC | GGATTTATAC | ACAAATCCTA | CAGGTGGAGC | 720 |
| ATTAGTGATT | ATTATCATTA | CAGCTATTGC | TGGTTTGGCT | ATTCTTATTC | CAAGCGTTAG | 780 |
| TCTGACAGCC | CGTCGTTTGC | GAGATGCACG | TCTTCCTTGG | TGGATTTCTC | TTATCTTTGG | 840 |
| TTTAGCAGCC | ATTTATGGTT | TACTTACAAT | GTTATTCAT | CAAGAAATGC | TTCAACAGTT | 900 |
| AGGATTCATT | TTTAACTTAA | TCACTTTCAT | TGTCTATATC | CTCTGTCTTT | TCCCAACAAA | 960 |
| ATATGGAGTT | GAGGAAGAAG | ATGACTCAAG | ATCTTATGAA | TAGTACAAAA | AAGAAAGGTA | 1020 |
| AAATATGATA | CAAGCTTATA | AAAATATTG | GCAAGGGACT | TTTGTTTTCA | ATAAAAGAAC | 1080 |
| AAGTCGTAAG | GATTTTGGA | TGGCTTTATT | CACCCATCTG | ATTATTTTG | TGGTTTTACT | 1140 |
| AAAGGGCTAT | AATTTTTTTA | ACGGATTGGG | TTATTTCCCA | CTGTCAGTTT | TATGGCAATC | 1200 |
| AATCGGTTCA | TTTTTACTTT | GGCTTTTGTG | GATATATTTT | TTAGGAAGTT | TACTAGCCTT | 1260 |
| CTTGGCCATA | ACAGTTCGAC | GATTAAATGA | TACTGATTTG | CCTTGGGGAT | TAGTATTTCT | 1320 |
| AAATCTTGTT | TTTGGCTTAG | GAACTCTTGT | ACTATTGGTT | CTCAATTTAT | TTCCAAGTTC | 1380 |
| TCCTAAAAGA | GACAAGTTTA | AAGAGTTTGA | ATTAAAAAAT | AGTTCTAATT | | 1430 |

( 2 ) INFORMATION FOR SEQ ID NO:16:

( i ) SEQUENCE CHARACTERISTICS:
        ( A ) LENGTH: 994 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

| | | | | | | |
|---|---|---|---|---|---|---|
| TTTTCATTGC | CTACATTGGG | ATTAAAAACG | CTGGAATTTT | GCGCTTCATC | GCTGACCCAG | 60 |
| GAACTTATGT | GAACAATCAC | GGAACAATTA | CAGCAAATTC | ATCAATTGTT | CCAGAGCTTG | 120 |
| TAACTTTTAA | TAACCCAGGA | GTGTTGGTAG | CACTTGTTGG | GATTGTCGTG | ACAATGTTCT | 180 |
| TTGTCATTCG | TAAATGGCGG | GCAGGATTT | TGCTTTCAAT | CTTGGTAACA | ACTATCTTGG | 240 |
| CTCTTTTGAC | TGGCGTGGTT | AAAGTTGATG | TGAATACTTT | ATTTGCTGAA | AATAATTTGG | 300 |
| GGACTGCAAT | CAATCAAATG | GGAACAACCT | TGGTGCAGC | ATTTGGTCCA | AAAGGATTTG | 360 |
| GTTCTTTATT | CTCTGATTCA | TCACGTTATA | TTGAAGTATT | AATGACAGTT | CTTGCTTTCT | 420 |
| CATTGACTTC | AATCTTTGAC | CCAATCGGAA | CTTTCATCGG | AACTGGTCGC | GCGACAGGAA | 480 |
| TCTTTACTGA | TGAAGATTTG | AAAGACATGG | AAACAAGCCA | TGGTTTCTCA | TCAAAAATGG | 540 |
| ACAAAGCTTT | GTTTGCTGAC | ATGATTGCTA | CTCCAATCGG | AGCAATTTTC | GGAACATCAA | 600 |

| | | | | | | |
|---|---|---|---|---|---|---|
|ATACAACCGT|TTATGTTGAG|TCTGCTGCCG|GAATCGGTGC|AGGAGGACGT|ACTGGTCTTG|660|
|CATCAGTTGT|AACAGCAATT|ATGTTTGCTA|TCTCAAGCTT|GTTCTTACCA|CTTCTTGCGA|720|
|TTGTTCCAAC|ACAAGCAACA|GCACCAATTT|TGATTATCGT|TGGGATGATG|ATGCTTGGTT|780|
|CATTTAAAGA|AATTAAATGG|GGTGATTTGA|CAGAAGCGAT|TCCTGCTTTC|TTCGCCTCAG|840|
|TATTCATGGG|ACTTGCTTAT|TCAATCTCTT|ACGGGATTGC|AGCTGGATTT|ATCACTTATA|900|
|TCCTTGTCAA|ATTATTCACC|GGAAAAGTGA|AAGAAATTAA|ACCTGTAATT|TGGGTCGTTG|960|
|CTCTCTTGTT|CTTAATTAAC|TTTGGGGTCC|CGAG| | |994|

( 2 ) INFORMATION FOR SEQ ID NO:17:

( i ) SEQUENCE CHARACTERISTICS:
        ( A ) LENGTH: 1070 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

| | | | | | | |
|---|---|---|---|---|---|---|
|TGTCGTTTTT|TCTTCCAAAT|AAACGACAAT|ATGATTGTAC|TGCGCTCGAT|TAGGAAAGAC|60|
|AAATGGAAAA|AGAATCCAGC|AAAAATGGAA|TAAGCACTCC|AAACCAACTC|AGAATAGCCA|120|
|CCAATGTTTG|AAATATTTTA|CTCCCATAAT|TCCCTTTTTC|AAAATACGGG|TCATAAACTA|180|
|AAGATTTTTT|CGCCTCTTCA|CGGCTCAAGT|TTTGTTTCAT|TTCCGACCTT|TCTGAACTTT|240|
|TCAACCTTTT|ATAGTTATAG|TCAATACAAT|ACATTTCTT|TAATTATCTC|ATTTTTGTT|300|
|CACAAAAGCC|ATTTTATGAG|TCTATTTTA|ATTACAAAAA|ACAGTCAGAC|ACTCTATCAA|360|
|ACTGCTTTAT|ATTTATTATT|TATAATGATA|ACAGTCGATT|CTCCTTTTTT|ATCAACTTTT|420|
|GCTTTATGCT|ATAATTTACA|GATAAGAACG|ATCTACCTAA|AAAGGTTAAA|GGAGTATTAT|480|
|GATAAAAATT|TTAAAAATGA|CTCAAGATGG|CTTTGACCAT|TATATGTTGT|CCGCTATTAA|540|
|AAATTATGCT|AATGAGAAAG|TAAATAATGG|AACATGGGAG|TCTAAAGATG|CCCTTTCAAA|600|
|TTCAAAGAAA|CAGTATGCAC|TCCTGCTTCC|CGACGGCTTC|AAACTGCTAA|TCATTATTTT|660|
|TACTCAATTT|TTAATAAAGA|AGAAAAAATC|GGATATATCT|GAAATTTATG|AAGAATTTCA|720|
|AAATCTAGGA|TTTGGCTCAA|AAACCCTTGA|TTTAGTTGCC|GATAAAGCAA|AGAACTTGG|780|
|ATTCTCTTTT|TTGGGACTCC|ACGTTTTGG|AAGTAATTCT|AGAGCTTTGC|ATGTCTATAA|840|
|AAAAATGGGA|TTCCAAATTA|CCGATATCAA|TATGCGAAAA|GAACTATGAA|TATCCACTCC|900|
|ATTTTTGGTT|GCCATTTGTT|AACGCTGCCT|CCTCTCCCTA|GTGCTATAAT|AAAAATGGCC|960|
|AAAAAAAAAC|CATTTTATTG|ACTATATTTG|CAATTTATTT|ACACATTATC|TTTTCAGAAC|1020|
|CAAAATCTGG|CCCATTTTGG|AACAGACTTC|TACTATTTTG|TTGTCTAGTA| |1070|

( 2 ) INFORMATION FOR SEQ ID NO:18:

( i ) SEQUENCE CHARACTERISTICS:
        ( A ) LENGTH: 480 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

| | | | | | | |
|---|---|---|---|---|---|---|
|GAATTCTTGA|TTCAATGAGA|GCTATTATGC|TTATCGTCGA|ATTAGAAGGT|GCATTTGATA|60|
|TTAGTCTTCC|ACCATCAGAA|ATGGACCGTG|AAGATTGGAA|TACAGCAAAT|AAAATAGCAG|120|
|CACGCGTTCA|GGAAAAAACG|GATGAAAATT|AAAATTTTTA|GAGCAATTGG|CCCACTAATT|180|
|GCAGCTTTAG|TTCTCGTTGC|TTTATTAATA|TTTCTCCCTT|TTAACGTTG|GAATGAAATA|240|

```
TTCTAAAGAC  CAACTCGTTA  AGTTTGCACA  GTCACCCTTA  AATACACCTA  CTTTTACAGG    300

ATATTCAATT  AAGAAACAAG  CCTATTCAGA  TCCTGAATTT  TTACCAGTTC  TCGGTTCGTC    360

AGAAATGGAA  CACGTTGATT  CATTTCACCC  AAGTGCTTAT  TTCAGCAAAT  ATAATTCAGG    420

TTTCATACCA  TTTTTAGTAG  GACAACCCGG  AACAACGACA  TTAACTCACT  TTTTCTATAT    480
```

( 2 ) INFORMATION FOR SEQ ID NO:19:

( i ) SEQUENCE CHARACTERISTICS:
         ( A ) LENGTH: 853 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:19:

```
TTAGAACGTC  AATGAGATAG  AAAAACAAAA  TATTTAAGAA  TAAAATGATA  CTGTTTTCCT     60

TAACTTAATG  ACATTGGGGT  ATACCCTGTT  GTCCATCAAA  AAAAATCTTC  TAAAATTATT    120

TTACTCAAAT  TGATAGATTA  TTTTTATGAA  ATGTGTTAAC  ATTTATTACT  ATCTAAATAG    180

CCAGAAAATT  CTACAATAGA  GTTATAAATT  AATGGAGACT  CTATATGAGA  AAAAATAAAA    240

CCAAGTTTAT  TGCTTTTGCA  CTTGCTTAAG  CAGTTATTGC  AGTAGGTTAC  TCAACTGCAG    300

CTTCTGCTGA  TTCTGTTACT  TCCTCAGATA  AAGATACAGT  CTCAAATCCA  ATTCTGACAA    360

TTACACCTCG  TATGAATGTT  GAGTTTCAAG  GTGGTGGATA  TTGGACAAAT  ACTTCGCACC    420

TGACCTACAT  TCAAAATACA  GGTTCTGGAG  TACTGTATTA  TGACCGAGTA  AATCATAAAT    480

ATGTATTTTC  ACAAACAAGA  GGTGCAATGG  GTGCAGCTAT  TTATGTTTTT  AACGCTCAGG    540

GTGTAAACTG  GTATAGAGGA  GTACTTTATG  TTTAAGAGTA  AAAAAAATGA  TGAGAAGAAG    600

GTTGAAATAC  TCAATTCTAT  TGATAAACTT  CTTCATCAAG  ATGTTGAATT  AACAATAGAC    660

GAAAAGAAA  TACTGTTAAA  ATATAAAGAG  CGGATTCAAA  ATTCAAAAAA  TATTGAATTT    720

GAACTGATTC  ATCTTAGAAA  TGCTCTTCTT  CCATTTGTTA  TAAGTTCGAA  ACTTTCCGAA    780

CCTACATTAA  ATTTCTATAA  AAAAATACGA  GCAGATAGAA  AAATTAGATG  GGGAGAAGGT    840

AGCTCTCTAA  TTA                                                          853
```

( 2 ) INFORMATION FOR SEQ ID NO:20:

( i ) SEQUENCE CHARACTERISTICS:
         ( A ) LENGTH: 1100 base pairs
         ( B ) TYPE: nucleic acid
         ( C ) STRANDEDNESS: single
         ( D ) TOPOLOGY: linear ( i x ) FEATURE:
         ( A ) NAME/KEY: CDS
         ( B ) LOCATION: 1..57

( x i ) SEQUENCE DESCRIPTION: SEQ ID NO:20:

```
ACA  GAT  TCT  AAA  CCA  GAA  GAA  AAT  AAG  GAA  AAA  TCA  GAA  GAT  GAA  ACA            48
Thr  Asp  Ser  Lys  Pro  Glu  Glu  Asn  Lys  Glu  Lys  Ser  Glu  Asp  Glu  Thr
  1                5                    10                   15

GCC  GAA  TAAGGCTGTT  TTTCTTTTTT  TTATGTTTA  GAATAAGTGG  TCTAGTTTAT        104
Ala  Glu

TCTTGACAAA  AAATAATATT  TTGATATAAT  TAAATAGTTG  TCGTTTGAGA  CGACTGACTT    164

TCTTATTATT  CATCTAAAAT  ATTATTTTGA  AAAGATAACA  CAGTTTATTC  TTGACAAAAA    224

AATATAAAAG  TGTATAATAG  AAAAGTACTG  TTTGAGACAG  CACAACAATA  TATGGTCCGT    284

TGGTCAAGGG  GTTAAGACAC  CGCCTTTTCA  CGGCGGTAAC  ACGGGTTCGA  ATCCCGTACG    344
```

```
GACTATATCT  GGAGGATTAC  CCAAGTCCGG  CTGAAGGGAA  CGGTCTTGAA  AACCGTCAGG    404

CGTGTAAAAG  CGTGCGTGGG  TTCGAATCCC  ACATCCTCCT  TTTTAATTAT  CGCGGGATGG    464

AGCAGCTAGG  TAGCTCGTCG  GGCTCATAAC  CCGAAGTCAT  AGGTTCAAAT  CCTATTCCCG    524

CAATTTTGGC  TCGGTAGCTC  AGTTGGTAGA  GCAATGGATT  GAAGCTCCAT  GTGTCGGCGG    584

TTCGATTCCG  TCTCGCGCCA  TTCCTTATTT  AGCGGATGTA  GTTAATGGT   AGAACCCAG     644

CCTTCCAAGC  TGGCTACGCG  AGTTCGATTC  TCGTCATCCG  CTTAACTTAA  TATTTTGGGA    704

GTTTAGCTCA  GTTGGTTAGA  GCACTGTGTT  GATAACGCAG  GGGTCCCAGG  TTCGAATCCT    764

GGAATTCCCA  TATTTGGTAT  TTATTGCATA  GGAGATATAC  CTGTTCCCAT  GTCGAACACA    824

GAAGTCAAGT  CCTTTTGCGC  TGGAAGTACT  TGGGGGTTGC  CCCCTGGGAG  ATAAAGACGA    884

TGCCAAGTTT  ACATTGCGGA  TTAGCTCAGT  TGGTAGTAGC  GCATGACTGT  TAATCATGAT    944

GTCGTCAGTT  CGAGTCTGAC  ATCCGCAGTA  ACTAAGTCAC  CTAAGGGTGA  CTTTTTTTAT    1004

TTTATAAATA  TTATCAATAA  ATCTTGGCAC  GCCTTTTGT   GTCAAGATTT  TTATTTACAG    1064

CTTTATTGGT  AGCGGTTACA  ATATAATTAT  ACTAGT                                1100
```

( 2 ) INFORMATION FOR SEQ ID NO:21:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Thr Asp Ser Lys Pro Glu Glu Asn Lys Glu Lys Ser Glu Asp Glu Thr
 1               5                  10                  15
Ala Glu
```

( 2 ) INFORMATION FOR SEQ ID NO:22:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
AGAATAAGTG  GTCTAGTTTA  TTCTTGACAA  AAAATAATAT  TTTGATATAA  TTAAATAGTT   60

GTCGTTT                                                                   67
```

( 2 ) INFORMATION FOR SEQ ID NO:23:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
TGAAAAGATA  ACACAGTTTA  TTCTTGACAA  AAAAATATAA  AAGTGTATAA  TAGAAAAGTA   60

CTGTTTG                                                                   67
```

( 2 ) INFORMATION FOR SEQ ID NO:24:

( i ) SEQUENCE CHARACTERISTICS:
        ( A ) LENGTH: 69 base pairs
        ( B ) TYPE: nucleic acid
        ( C ) STRANDEDNESS: single ( D ) TOPOLOGY: linear ( x i ) SEQUENCE DESCRIPTION: SEQ ID NO:24:

ATCAGTGATT TATGAGTTTT TTCTTGACAG AAGAAGGCGA AAAATGGTAT TATATTTAGG      60

TACTGTTTT      69

( 2 ) INFORMATION FOR SEQ ID NO:25:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

ATCAGTGATT TATGAGTTTT TTCTTGACAG AAGATGGCGA AAAATGGTAT TATATCTAGG      60

TACTGTTTT      69

( 2 ) INFORMATION FOR SEQ ID NO:26:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CTTTGAAATA AATAAGTTAA AACTTGAAAT TTATGAGGGT TTTTGGTAAA ATATTTCTTG      60

TCGTCATCA      69

( 2 ) INFORMATION FOR SEQ ID NO:27:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

TTTTGCATGT AATGAGTTTA TTCTTGACAA CTTTTGGGAA ACTTGGTATA CTAATATAGT      60

CGTTTAAG      68

( 2 ) INFORMATION FOR SEQ ID NO:28:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GGTATAAAAG TCACAGTTAA TTCTTGACAA GTTTAGTTAG GTTTGATAGA ATATAATAGT      60

TGTCGCAA      68

( 2 ) INFORMATION FOR SEQ ID NO:29:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

ACCTAAAAAT TGACAGTTAA TTCTTGACAG GGAGAGATAG GTTTGATAGA ATATAAGTTG      60

TCACGA                                                                                                          66

( 2 ) INFORMATION FOR SEQ ID NO:30:

( i ) SEQUENCE CHARACTERISTICS:
    ( A ) LENGTH: 68 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

TAGTTATTCT TATTTCATAT TATTTCAGGA AGGTAATTAA CTATGGTATA ATGAAATTAG      60

ATAAGGGA                                                                                                        68

( 2 ) INFORMATION FOR SEQ ID NO:31:

( i ) SEQUENCE CHARACTERISTICS:
    ( A ) LENGTH: 67 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

TATCCTATTA ATCAAGTTGA CCTTGAAAAA AAACTGAAAA TCTGTTATCA TAAATAATGG      60

ACATTTT                                                                                                         67

( 2 ) INFORMATION FOR SEQ ID NO:32:

( i ) SEQUENCE CHARACTERISTICS:
    ( A ) LENGTH: 846 base pairs
    ( B ) TYPE: nucleic acid
    ( C ) STRANDEDNESS: single
    ( D ) TOPOLOGY: linear ( i x ) FEATURE:
    ( A ) NAME/KEY: CDS
    ( B ) LOCATION: 720..845

( x i ) SEQUENCE DESCRIPTION: SEQ ID NO:32:

GATCATCTAC AATCATTAAA AGTTTATCAA AGAGCCGAAG ATAGTTCTCA GATTCTGGTG      60

GATAATCCAT CATCAATTGT GCGAGGTTTG GATAAGATTC TAAAACAGTA TAAATATTTT     120

TACCATAGAC GAAAAGGCGG TCTTGCCACG TTTTCTCATT TGCTGGAAAA ATAATTTCAA     180

GGCTTGCTTT ATCAATAAGT TCTGCAAAAA GTGCTTCTTT ACTTGAAAAA TGGTAGTAAA     240

GAGAAGACAC TGTCATTCCT ACGGCACTAG CTAACTTACG CATTGAAAAT TCTGTGAGAG     300

TAAGTTCTTC TAAAAGTTCC CAGCTGCTAC TAATAATTTT ATCTTTGGTT GGTTGAGTCG     360

CCATAAGTTT TCGCTTTCTT TTTCTACTTA GATTTATTTT ACATGTTTTT AATGAAAATT     420

GCGATAGAAA AGCTGATAAA CAAATTTGTC ATTTAAATAT TGTAAGGGGA AAACTCTAGC     480

TATAATTGAG TAAATACCGA ACAATCTCTC TTCTTATTTC TTGAAACTTT TGTTCAGGCT     540

TTTTCTTTTA TCACAAATCT TTAAGATAG AATTATAAGA TTTATAAAGC AAGAAAGAT      600

AGATGAGCTA TCGTCACTTT GACTTTTATT ATTCGTTCAA GATTGTTGA ATAATAAATA    660

AAATAGCTGA ATACACAAGT CTGTGTATAT AAAAAGCGTT TGGGAATATC GGAGAAATG    719

ATG AAA ATT TTG GTA ATT GGT TCT GGC GGC CGC GAA CAT GCC TTA GCA     767
Met Lys Ile Leu Val Ile Gly Ser Gly Gly Arg Glu His Ala Leu Ala
 1      5        10       15

AAA AAA TTT ATG GAA AGT CCT CAA GTT GAA GAA GTC TTT GTA GCT CCA     815
Lys Lys Phe Met Glu Ser Pro Gln Val Glu Glu Val Phe Val Ala Pro
    20       25       30

```
GGC  AAT  TCA  GGA  ATG  GAA  AAA  GAT  GGA  ATT  C                                    846
Gly  Asn  Ser  Gly  Met  Glu  Lys  Asp  Gly  Ile
              35                        40
```

(2) INFORMATION FOR SEQ ID NO:33:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:33:

```
Met  Lys  Ile  Leu  Val  Ile  Gly  Ser  Gly  Gly  Arg  Glu  His  Ala  Leu  Ala
 1                  5                       10                       15
Lys  Lys  Phe  Met  Glu  Ser  Pro  Gln  Val  Glu  Glu  Val  Phe  Val  Ala  Pro
              20                      25                       30
Gly  Asn  Ser  Gly  Met  Glu  Lys  Asp  Gly  Ile
              35                      40
```

(2) INFORMATION FOR SEQ ID NO:34:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:34:

```
Lys  Leu  Ser  Arg  Ala  Arg  Asp  Leu  Gln  Asp  Pro  Gly
 1                  5                       10
```

(2) INFORMATION FOR SEQ ID NO:35:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:35:

```
Ser  Phe  Arg  Glu  Leu  Glu  Ile  Cys  Arg  Ile  Pro  Gly  Asn  Phe  Glu  Arg
 1                  5                       10                       15
Ile  Phe  Leu  Met
              20
```

(2) INFORMATION FOR SEQ ID NO:36:

(i) SEQUENCE CHARACTERISTICS:
        (A) LENGTH: 19 amino acids
        (B) TYPE: amino acid
        (D) TOPOLOGY: linear (xi) SEQUENCE DESCRIPTION: SEQ ID NO:36:

```
Ala  Phe  Ala  Ser  Ser  Arg  Ser  Ala  Gly  Ser  Arg  Val  Thr  Leu  Lys  Gly
 1                  5                       10                       15
Tyr  Ser  Ser
```

(2) INFORMATION FOR SEQ ID NO:37:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:37:

```
Lys  Leu  Ser  Arg  Ala  Arg  Asp  Leu  Gln  Asp  Pro  Gly  Ser  Arg  Leu  Gly
```

(2) INFORMATION FOR SEQ ID NO:38:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:38:

```
Ser Phe Arg Glu Leu Glu Ile Cys Arg Ile Pro Gly Leu Asp
 1               5                  10
```

(2) INFORMATION FOR SEQ ID NO:39:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:39:

```
Ala Phe Ala Ser Ser Arg Ser Ala Gly Ser Arg Val
 1               5                  10
```

RECOMBINANT LACTIC ACID BACTERIUM CONTAINING AN INSERTED PROMOTER AND METHOD OF CONSTRUCTING SAME

This is a continuation-in-part application of U.S. Ser. No. 08/036,681, filed Mar. 25, 1993, now abandoned.

FIELD OF INVENTION

This invention pertains to the field of genetically improved food grade lactic acid bacteria. In particular there are provided methods for isolating useful lactic acid bacterial promoters and construction of recombinant lactic acid bacteria in which such promoters are utilized to obtain improved lactic acid bacteria which are useful in the manufacturing of foods, animal feed and probiotically active compositions.

TECHNICAL BACKGROUND AND PRIOR ART

For centuries, lactic acid bacterial cultures have been used in food production due to their ability to convert sugars by fermentation into preserving organic acids, predominantly lactic acid, and various metabolites associated with the development in fermented food products of desirable taste and flavour. Several lactic acid bacteria produce hydrolytic enzymes including peptidases, proteases and lipolytic enzymes, the production of which may e.g. contribute to a desired flavour development in cheeses.

However, for industrial production of a wide range of fermented food products such as all the well-known traditional dairy products including yoghurt, acidophilus milk, butter and cheeses; fermented vegetables; fermented meat products and animal feed, a large range of lactic acid bacterial starter cultures, each being adapted to particular types of food products, are required. Such cultures are presently being selected from naturally occurring strains of lactic acid bacteria on the basis of characteristics such as their ability to ferment sugars present in the food product to be fermented, specific growth temperature requirements, production of desired flavouring compounds, the specific combination of which characteristics renders a specifically selected wild-type culture useful for the production of a particular food product but normally less useful for the production of others.

Obviously, this presently used procedure for developing useful lactic acid bacterial cultures by selection of naturally occurring strains is cumbersome and costly. Furthermore, it has proven difficult to provide starter culture strains which combine all of the required characteristics at an optimal level. Presently, this problem is usually solved by the use of starter cultures comprising a multiplicity of selected lactic acid bacterial strains each having one or several of the characteristics desirable for a particular food product. The necessity to use such mixed cultures will of course add to the costs in the manufacture of lactic acid bacterial starter cultures.

Based on their traditional and long term application in food manufacturing and the fact that they are considered as non-pathogenic, the lactic acid bacteria are generally recognized as safe (GRAS) food ingredients, even if they are present in a fermented food product as live bacteria at a very high number, such as $10^8$ to $10^9$ per g.

Currently, it is widely recognized that a substantial industrial need exists to find economically and technically more feasible ways of developing starter cultures. It is obvious that gene technology may provide the means to meet this need. In this context, it is crucial that lactic acid bacteria for food manufacturing which are developed by introduction of desired genes by use of gene technology can still by recognized as safe for consumption. It is therefore considered by the industry that it is essential that recombinant lactic acid bacteria contain only DNA of lactic acid bacterial origin including DNA from wild-type extrachromosomal plasmids frequently found in starter culture strains or non-lactic acid bacterial DNA which does not confer to the recombinant strains any hazardous phenotypic traits.

There have been several attempts of providing genetically improved lactic acid bacteria. Most of these attempts have been directed to the construction of recombinant expression vectors coding for desired gene products and capable of replicating in lactic acid bacteria. However, very few of these attempts have resulted in vectors comprising only lactic acid bacterial DNA.

Another approach to the improvement of lactic acid bacteria would be to have useful genes inserted into the chromosome of the bacteria or to enhance the expression of chromosomal genes coding for desired gene products. Such an approach might, if successful, circumvent the problem which is frequently encountered when new genes are introduced on a plasmid, viz. the loss of such plasmids due to inherent instability or as a result of the presence of other plasmids belonging to a different incompatibility group. In contrast thereto, an introduced gene which becomes integrated in the chromosome is generally stably inherited by daughter cells.

However, this latter approach is still not well-studied in lactic acid bacteria due to the lack of detailed knowledge of the chromosomes of lactic acid bacteria and due to lack of suitable methods of obtaining chromosomal integration of heterologous DNA, although recent publications have reported on such chromosomal integration in *Lactococcus lactis* ssp. *lactis* by means of so-called integration vectors (reference 46).

It is known that the expression of a homologous or heterologous gene may be enhanced, e.g. by replacing a promoter sequence naturally associated with that gene with a stronger promoter sequence which results in an enhanced expression of the gene at the transcriptional level. Thus, DD 228 564 discloses a method of preparing an expression vector capable of replication in *E. coli* and/or *B. subtilis*, comprising inserting into a unique restriction site a promoterless basic *E. coli* and/or *B. subtilis* plasmid comprising a structural gene, a promoter-carrying DNA fragment isolated from a Streptococcus species by restriction with a restriction enzyme corresponding to the unique restriction site of the basic plasmid, and isolating the thus recombinant vector from *E. coli* and/or *B. subtilis* transformed with the vector and expressing the structural gene.

Youngman et al. (1987) disclosed a method for the isolation of promoters in Bacillus spp. using the transposon Tn917. However, this method is based on the ability of Bacillus spp. to grow at temperatures above 37° C. and it has furthermore been found that this transposition procedure in Bacillus spp. results in the transposon being integrated into a dominating hot spot whereby a single dominant integrant will occur.

It has recently been suggested that sequences comprising a lactic acid bacterial promoter and/or promoter-signal peptide sequences may be used to replace weaker native promoters and/or promoter-signal peptide sequences in plasmids to obtain- a more efficient expression and secretion of an *E. coli* gene product, viz. β-lactamase in the lactic acid bacterium *Lactococcus lactis*. (reference 28). These authors identified the Lactococcus promoter sequences by means of a promoter probe vector capable of replication in E. coli and/or B. subtilis and comprising a promoterless cat gene and suitable restriction sites into which fragments of the Lactococcus chromosome could be inserted followed by screening for recombinant plasmids isolated from E. coli or B. subtilis and expressing the cat gene.

However, such a method involving the screening in a non-lactic acid bacterium for insertion of lactic acid bacterial promoters in a vector which is not of lactic acid bacterial origin and which is replicated in a non-lactic acid bacterium does not allow for a direct in situ identification of a useful lactic acid bacterial promoter while functioning in the lactic acid bacterium of origin. Such a direct method is provided by the present invention.

SUMMARY OF THE INVENTION

In one aspect the present invention relates to a method of isolating a lactic acid bacterial DNA fragment comprising a promoter, the method comprising the steps of:

(i) selecting a DNA molecule replicating in a lactic acid bacterium, said molecule comprising (a) a transposable element comprising a promoterless structural gene as a promoter probe gene, (b) a detectable selective marker gene, and (c) an origin of replication which is functional in a lactic acid bacterium, (ii) introducing the DNA molecule into a population of a lactic acid bacterium, followed by subjecting the population to conditions allowing transposition of the transposable element to occur, (iii) selecting a cell of the lactic acid bacterial population in which the promoterless gene is expressed, (iv) cloning said cell and isolating from the clone a DNA fragment comprising a lactic acid bacterial promoter being operably linked to the originally promoterless gene and possibly sequences regulating the function of the promoter.

In further aspects the invention provides methods of constructing a recombinant lactic acid bacterium comprising the steps of:

(i) isolating in accordance with the above method a DNA fragment comprising a regulatable lactic acid bacterial promoter, (ii) inserting the isolated fragment comprising the promoter into a lactic acid bacterium upstream of a gene coding for a desired gene product, the inserted promoter thereby becoming operably linked to said gene or a method of constructing a recombinant lactic acid bacterium comprising the steps of:

(i) isolating in accordance with the method of claim 1 a DNA fragment comprising a regulatable lactic acid bacterial promoter, (ii) inserting into a lactic acid bacterium a gene coding for a desired gene product, (iii) inserting the isolated fragment comprising the promoter into the lactic acid bacterium resulting from step (ii) upstream of the gene coding for a desired gene product, the inserted promoter thereby becoming operably linked to said gene.

In a still further aspect, the invention relates to a method of constructing a recombinant lactic acid bacterium comprising the steps of:

(i) selecting a DNA molecule replicating in a lactic acid bacterium, said molecule comprising (a) a transposable element comprising a promoterless structural gene as a promoter probe gene, (b) a detectable selective marker gene, and (c) an origin of replication which is functional in a lactic acid bacterium, (ii) introducing under conditions allowing transposition of the transposable element to occur, the DNA molecule of step (i) into a population of a lactic acid bacterium, (iii) selecting a cell of the lactic acid bacterial population in which the promoterless structural gene is regulatably expressed as a result of being operably linked to a native regulatable promoter of the lactic acid bacterial cell, (iv) identifying the site in a replicon of the lactic acid bacterial cell of step (iii) into which the transposable element is integratable, and (v) inserting into a non-integrant cell of the lactic acid bacterial population at a site as identified in step (iv) or at a functionally equivalent site, a gene coding for a desired gene product whereby the gene becomes operably linked to said native lactic acid bacterial promoter, the expression of the inserted gene hereby being altered as compared to the expression of the gene when operably linked to its native promoter.

In other further aspects the present invention relates to a recombinant lactic acid bacterium comprising a gene coding for a desired gene product and operably linked thereto a regulatable lactic acid bacterial promoter not natively associated with the gene, the presence of said promoter resulting in the expression of the gene being altered as compared to the expression of the gene when operably linked to its native promoter and to an isolated DNA fragment comprising a lactic acid bacterial promoter which is functional in a lactic acid bacterium and operably linked thereto, a gene coding for a desired gene product, said promoter being one which is not naturally associated with the gene.

The invention also relates to the use of a recombinant lactic acid bacterium as defined herein in the manufacturing of food products, in the preservation of animal feed and in the manufacturing of a probiotically active composition.

In yet an other aspect the present invention provides a recombinant plasmid comprising a DNA sequence comprising a regulatable lactic acid bacterial promoter, a gene coding for a desired gene product, a lactic acid bacterial replicon which is functional in a lactic acid bacterium, an insertion site allowing the DNA sequence to be inserted so that the gene coding for the desired gene product is operably linked to the promoter, whereby the gene can be transcribed when the plasmid is present in a lactic acid bacterium.

In a still further aspect, the present invention relates to a recombinant plasmid comprising a vector comprising a promoterless gene coding for a desired gene product, a theta-replicating lactic acid bacterial replicon which is functional in a lactic acid bacterium and an insertion site allowing a DNA sequence to be inserted, and inserted into said insertion site a DNA sequence comprising a regulatable lactic acid bacterial promoter, the insertion resulting in that the gene coding for the desired gene product is operably linked to the promoter, whereby the gene is transcribed. Thus, such a plasmid may comprise as the vector, the plasmid pAK80.

DETAILED DISCLOSURE OF THE INVENTION

A primary object of the present invention is to provide the means of constructing improved lactic acid bacteria which are food grade in the sense that they contain only DNA derived from a lactic acid bacterial species or DNA from a non-lactic acid bacterial species the presence of which may be generally recognized as safe. As used herein the term "lactic acid bacterium" designates gram-positive, microaerophilic or anaerobic bacteria which ferment sugars with the production of acids including lactic acid as the predominantly produced acid, acetic acid and propionic acid. The industrially most useful lactic acid bacteria are found among Lactococcus spp., Streptococcus spp., Lactobacillus spp., Leuconostoc spp., Pediococcus spp., Brevibacterium spp., Propionibacterium spp. and Bifidobacterium spp.

As it is mentioned above, the invention provides in one aspect a method of isolating a lactic acid bacterial DNA fragment comprising a promoter. In a first step of this method there is provided a DNA molecule capable of replicating in a lactic acid bacterium, said molecule comprising a transposable element, a promoterless structural gene as a promoter probe gene, a detectable selective marker gene, and an origin of replication which is functional in a lactic acid bacterium. Provided such a fragment can be introduced into a lactic acid bacterium and subsequently become integrated in a host cell replicon (including the chromosome and/or plasmids carried by the host) as a result of transposition events, host cell promoters may be identified by the detection of expression in the host cell of the promoterless structural gene of the integrated DNA fragment, since the structural gene lacking a promoter region cannot be expressed unless the insertion of the transposable element occurs at a site of a replicon where a promoter region present on the disrupted replicon molecule becomes operably linked to the gene.

In the present context, the term "transposable element" is used to designate double stranded DNA molecules which possess the capacity to insert themselves into other DNA molecules. The process by which a transposable element inserts itself is termed "transposition" and this process requires a protein known as a "transposase" (cf. reference 3 for detailed explanations). The transposition process results in the insertion of the transposable element into a particular site in a second DNA molecule. This insertion has several significant consequences. First, the original DNA sequence of the second (recipient) DNA molecule is physically and functionally disrupted. Second, since transposition results in the incorporation of new DNA into a second DNA molecule, it provides the means of introducing homologous or heterologous DNA into a particular DNA sequence. Third, it is possible to engineer a transposable element so that its insertion into a DNA sequence can provide information regarding the expression and organization of the DNA sequence which flank the site of insertion. For example, it is possible to insert a gene which encodes a non-expressed or non-excreted gene product near the end of a transposable element and accordingly, such a transposable element provides a probe for promoters and secretion signal peptide.

Transposable elements which may be used in accordance with the invention are diverse in both size and functional organization. Thus, simple transposable elements, termed "insertion sequences", encode no functions unrelated to their own movement and are generally shorter than 2 kb. Like all transposable elements, insertion sequences possess specialized termini which contain complementary sequences which are inverted repeats of one another. The presence of such inverted repeat sequences appears to be essential for transposition. Transposase enzymes are thought to mediate transposition by binding to DNA sequences at both ends of the transposable element.

Useful transposable elements include transposons. The term "transposons" denotes transposable elements which are larger than insertion sequences and which in addition to the transposase system encode several gene products such as proteins which confer cellular resistance to antibiotics or other selectable determinants.

Although most work concerning the exploitation of transposable elements as gene technology tools has been done in gram-negative bacterial species, several transposons which are functional in gram-positive species have been isolated and studied, mainly in Bacillus spp, Listeria spp and Coryne-bacterium spp, but also to less extent in lactic acid bacteria. Examples of transposons which may be used in lactic acid bacteria include Tn916 isolated from Streptococcus and functional i.a. in Listeria spp, Mycoplasma spp, Staphylococus spp; Tn9l9 isolated from *Streptococcus sanguis* which has been shown to transpose in the lactic acid bacterial species *Lactobacillus plantarum, Leuconostoc cremoris* and *Lactococcus lactis*; and Tn917 isolated from *Streptococcus faecalis* known to transpose in Bacillus spp and Listeria spp.

For the purpose of the present invention a useful transposable element is one that mediate operon fusion and transcriptional fusion. Accordingly, such fusion-generating derivatives of a transposon which has lactic acid bacterial DNA molecules as their target, including derivatives of the above gram-positive transposons may be used in the present method. As an example, fusion-generating transposon derivatives may comprise a promoterless structural gene, the expression of which is readily detectable. Such a promoterless structural gene may e.g. be selected from a gene coding for a gene product conferring antibiotic resistance, a gene coding for a gene product complementing an auxotrophic deficiency or a gene coding for an enzyme having a readily detectable end product such as a product resulting in a colour reaction in an appropriate solid or liquid medium.

For example, the insertion of a promoterless lacZ gene into a plasmid comprising the transposon, in an orientation suitable for obtaining transposition-mediated fusions results in a plasmid vector that turns bacteria containing it, blue when grown on plates containing 5-bromo-4-chloro-3-indolyl-β-D-galactopyranoside (X-gal) as a result of the expression of β-galactosidase. Transpositional insertions into the chromosome or into a plasmid, generated with such vectors produce white colonies, unless the insertions occur downstream of a functional promoter and in the right orientation to effect a transcriptional fusion. In this manner the promoterless gene serves as a promoter and/or operon probe gene. As another example, a suitable fusion-generating transposon derivative may comprise the promoterless gene cat-86 gene, the gene product of which mediate chloramphenicol resistance.

In the present context, an essential characteristic of a suitable transposable element is its ability to transpose with a high degree of randomness. Transposable elements vary greatly in target specificity, and their sites of insertion often exhibit little or no similarity to element sequences. Some elements may have from a few to hundreds of target sites in any gene, although no element has been found to insert completely randomly. Other elements are highly site specific, inserting into just a single chromosomal site. Yet other elements seem to insert quasi-randomly in some species, but prefer either particular regions of DNAs or certain regions of DNA molecules. For the purpose of the present invention a transposable element which is randomly or at least quasi-randomly integrated is preferred, the term "quasi-randomly" being defined herein as a degree of integration randomness in terms of the proportion of the total number of insertion events which is observed in a target DNA fragment of a known size relative to the proportion of insertions expected in this DNA fragment which is at the most 5, preferably at the most 4, more preferably at the most 3 and in particular at the most 2.5. In useful embodiments transposable elements which have a preference for chromosomal DNA may be preferred.

In certain preferred embodiments, a DNA molecule capable of replicating in a lactic acid bacterium and comprising a fusion-generating derivative of the Tn917 transposon may be selected for the present method. Such derivatives include plasmids of the pTV series which include pTV32, pLTV1, pLTV3, pTV51, pTV52 and pTV53. Of these, pTV32 and pLTV1 may be particularly useful.

Furthermore, the DNA molecule as provided in step (i) of the present method comprises a detectable selective marker gene allowing the selection of cells in which the DNA fragment has been introduced. In this connection, convenient marker genes include ones coding for gene products conferring resistance to antibiotics, e.g. resistance to macrolide antibiotics such as erythromycin and lincomycin; tetracycline, β-lactam antibiotics and chloramphenicol. As other examples, the marker gene may code for the complementation of auxotrophy in the host cell into which the DNA fragment is introduced or it may be a gene coding for an enzyme capable of generating a readily detectable end product such as e.g. the above-mentioned lacZ gene.

In a second step of the present method, the DNA molecule as defined above is introduced into a population of cells of a lactic acid bacterium. Such an introduction may be carried out in accordance with known techniques of introducing DNA into a host cells including transformation of protoplasted cells, transformation by electroporation or, if the DNA fragment is a conjugative element, by conjugation. The selected method should preferably result in a frequency of DNA introduction which is at least $10^4$ recombinant cells per µg of DNA such as at least $5 \times 10^4$ per µg of DNA, e.g. at least $10^5$ per µg of DNA.

In order to secure a high probability of obtaining integration of the transposable element into host cell DNA it is essential that the DNA molecule is one which is capable of replicating in the host cell. Accordingly, step (ii) may include a substep allowing the introduced replicon to replicate, followed by a procedure to study to what extent replication has occurred in the transformant or exconjugant. In the present context, a suitable extent of replication is considered to be a copy number which is in the range of 5 to 20 per cell. It is contemplated that a copy number substantially exceeding this range may render the curing of the replicons, which is an essential prerequisite for a subsequent transposition to occur, more difficult to achieve.

In a further substep, step (ii) comprises subjecting the transformant or exconjugant cells to conditions which allow transposition to occur. Transposition in non-lactic acid bacteria may be induced by one or more shifts in the environmental conditions of the cells. As an example hereof, the procedure for pTV-based Tn917 mutagenesis in *B. subtilis* includes a step involving an antibiotic switch combined with a temperature upshift. Both Tn917 erm gene expression and transposition are induced in *B. subtilis* by erythromycin (reference 57). In *B. subtilis*, the replication activity of pE194Ts-rep is blocked at temperatures above 37° C. (reference 56). Consequently, curing for pTV plasmids, induction of and selection for transpositions are done by growing *B. subtilis* at temperatures exceeding 42° C. in the presence of erythromycin.

During the experimentation leading to the present invention it was, however, found that the above procedure used in *B. subtilis* was not applicable to lactic acid bacteria such as the exemplified *Lactococcus lactis* ssp. *lactis* MG1614 and MG1363. However, it was surprisingly found that neither pTV32 nor pLTV1 could be extracted from the Lactococcus cells transformed with these plasmids when they were grown at 30° C. in the presence of erythromycin. This indicated that transposition (integration) of the Tn917 derivatives to the chromosome with a concomitant loss of plasmid had occurred under these conditions.

Accordingly, in one useful embodiment of the invention, step (ii) of the present method includes a substep where transposition of free transposable element-containing DNA molecules in transformed lactic acid bacteria is induced with a concomitant curing of such free molecules by growing the transformants at a temperature in the range of 20° to 35° C. such as 30° C. in the presence of an antibiotic to which the transposable element confers resistance.

In a subsequent step (iii) of the present method, integrant cells are cloned and subjected to a selection procedure to detect integrant cells wherein the promoterless gene of the transposable element is expressible. This selection procedure will depend on the type of the promoterless gene. When e.g. a promoterless lacZ gene is used, the selection may be carried out by plating the cloned integrants onto a medium containing a substance degradable by β-galactosidase with the development of a colour or, if an antibiotic resistance gene is used, the integrants may be selected on a medium supplemented with the corresponding antibiotic.

In step (iv) of the present method, a selected integrant expressing the promoterless structural gene is cloned and a lactic acid bacterial replicon region including a promoter being operably linked to the originally promoterless gene and possibly sequences regulating the function of the promoter is isolated from the cloned cells by the use of appropriate restriction enzymes. The resulting primary promoter-containing DNA sequences may have varying sizes depending on the location of restriction sites for the selected enzyme(s).

For further application of the isolated promoter-containing DNA sequences/fragments it may be advantageous to prepare subsequences of these primary sequences to obtain smaller fragments comprising the isolated promoter and possibly sequences regulating the function of the promoter. Whereas a primary promoter-containing fragment may e.g. have a size which is in the range of 40 to 600 kb, it is contemplated that a subsequence comprising the promoter and possibly other sequences required for its regulation may more appropriately have a size which is in the range of 50 to 10,000 base pairs.

In accordance with the present invention, the population of cells of a lactic acid bacterium into which the DNA fragment comprising the transposable element is introduced in the above-defined step (ii), are preferably selected from Lactococcus spp., Streptococcus spp., Lactobacillus spp., Leuconostoc spp., Pediococcus spp., Brevibacterium spp., Propionibacterium spp. and Bifidobacterium spp. In one particularly preferred embodiment, the lactic acid bacterium is selected from *Lactoccus lactis* subspecies *lactis* such as the *Lactoccus lactis* ssp. *lactis* strains MG1614 and MG1363. During industrial use in food manufacturing of genetically improved lactic acid bacteria as defined herein it may be advantageous that the function of the bacteria is regulatable so that specific phenotypic traits of the lactic acid bacterial starter cultures may be turned on or switched off or the rate of expression of that trait is enhanced or reduced during specified periods of the manufacturing process including a maturation process. As an example it may be desirable in cheese manufacturing to use cultures which are not proteolytically or lipolytically active to a high degree during the curdling process but which are so during the maturation of the cheese.

Accordingly, the present method may, in one advantageous embodiment be a method wherein the promoter comprised in the DNA fragment being isolated and selected is a regulatable promoter. Such a method includes steps whereby the isolated promoter-containing sequences possibly including regulatory sequences are screened for mode of regulation. In the present context, a regulatable promoter may be regulatable by a factor selected from the pH and/or the content of arginine in the environment, the growth temperature, a temperature shift eliciting the expression of heat chock genes, the composition of the growth medium including the ionic strength/NaCl content, and the growth phase/growth rate of the lactic acid bacterium into which the promoter-comprising DNA molecule is introduced. One example of a promoter regulation mode is the phenomenon of stringent control by which is understood that the RNA synthesis of a cell is suspended in case the cell is starved for an essential nutrient such as an amino acid.

Accordingly, a suitable regulatable promoter in accordance with the present invention may be one which is under stringent control.

An other example of a useful mode of regulating a promoter is to select a promoter that regulates a gene coding for an enzyme involved in the de novo synthesis of purine nucleotides from their precursors. By inserting into a lactic acid bacterium such a promoter which is regulated by being repressed in the presence of purine compounds, in front of a gene whose expression is to be regulated, this gene will only be expressed when the bacterium is growing in a medium not containing purine compound precursors. An example of such a regulated promoter is the lactococcal purD promoter as described hereinbelow.

As one example of screening for mode of promoter regulation, the isolated promoter may be screened for temperature/growth phase regulation by plating cells into which the promoter being operably linked to a gene coding for a gene product the expression of which is readily detectable, has been introduced by transposition, onto a suitable medium and incubating the plates at varying temperatures such as different temperatures within the range of 10° to 30° C. and observing for temperature dependent gene expression. However, since the growth rate of the integrants cells will depend on the growth temperature it cannot be determined whether an observed apparently temperature-dependent expression is a result of a direct temperature regulation or the dependence is due to growth phase regulation.

Likewise, a possible pH and/or arginine dependent regulation of gene expression may be screened for by plating the above integrant cells onto media having different compositions which will result in varying pH values after growth of the integrant cell cultures. As an example the cells may be grown on GM17 medium where the final pH will be about 5 and on a modified GM17 medium having ⅕ of the normal glucose content and supplemented with 0.5% arginine. The pH in such a medium after growth of a culture of *Lactococcus lactis* integrant cells as defined above will be about 9. When expression of the gene under control of the isolated gene is only observed at one of the two pH values, a pH and/or arginine dependent regulation is demonstrated.

Since one object of the present invention is to provide the means of constructing improved recombinant lactic acid bacteria by inserting promoter-containing sequences which result in enhanced expression of lactic acid bacterial gene(s) coding for desired gene products, it is part of the invention to screen promoter sequences for strength. This screening is carried out in accordance with methods which are known per se.

As it has been mentioned above, the present invention relates in a further aspect to a method of constructing a recombinant lactic acid bacterium containing a lactic acid bacterial gene coding for a desired gene product, the method comprising as a first step the isolation in accordance with the method as defined above, of a DNA sequence comprising a lactic acid bacterial promoter including where appropriate, additional regulatory sequences. The method comprises in a second step the insertion of the thus isolated DNA sequence into a lactic acid bacterium upstream of the lactic acid bacterial gene coding for the desired gene product so that the inserted promoter and possibly the above-defined regulatory sequences thereby becomes operably linked to the gene coding for a desired gene product.

The gene coding for a desired gene product may in accordance with the present invention be a homologous gene or it may be an inserted heterologous gene including a gene which is derived from a lactic acid bacterium. When the gene is an inserted gene it may be inserted on the same DNA sequence as that comprising the promoter sequence or it may be inserted on a separate DNA sequence.

In one useful embodiment, the insertion of the above isolated promoter-containing sequence may be on the chromosome of the lactic acid bacterium and in an other useful embodiment, the sequence may be inserted extrachromosomally e.g. on a plasmid harboured by the bacterium. As it has been mentioned above, it may be advantageous to have the promoter-containing sequence integrated into the chromosome, since the sequence and the gene to which it is operably linked is hereby more stably contained as compared to a location on an extrachromosomal element. The insertion of the promoter-containing sequence is done according to gene technology methods which are known per se such as by insertion into a plasmid by conventional restriction and ligation procedures or integration into the chromosome by the use of transposons or bacteriophages or by conventional recombinational techniques.

In one interesting embodiment, the isolated promoter-containing sequence comprises a further sequence whereby the isolated promoter becomes regulated by a stochastic event. Such a regulation may e.g. be useful in lactic acid cultures for which it is advantageous to have a gradually decreasing activity of the gene under control of the inserted promoter-containing sequence. Such further sequences may e.g. be sequences which result in a recombinational excision of the promoter or of genes coding for substances which are positively needed for the promoter function.

A stochastic regulation of the promoter function may also be in the form of recombinational excision of a regulatory sequence inhibiting the function of the promoter whereby a gradually increasing promoter activity is obtained at the recombinant cell population level.

As it is mentioned above, the present invention provides a further method of constructing a recombinant lactic acid bacterium which bacterium comprises a gene coding for a desired gene product, the expression of which is altered as compared to expression of the gene when it is operably linked to its native promoter. In this method a DNA molecule as defined above and comprising a transposable element with a promoter probe gene is utilized to identify a site/sites in a lactic acid bacterial replicon (chromosome or plasmid) in which the transposable element is integratable and where the promoterless probe gene becomes operably linked to a promoter sequence present in the replicon and subsequently, inserting in a non-integrant lactic acid bacterial cell at that or these sites or at a site/sites which are functionally equivalent thereto, a gene coding for a desired gene product, whereby this gene becomes operably linked to the identified promoter sequence.

Whereas the transposable element will become inserted between two base pairs, it will be understood that a gene coding for a desired gene product may, besides being inserted between those two base pairs also be inserted at a neighbouring site which is located at a distance from that specific insertion (integration) site which will still allow the identified promoter sequence to control transcription of the inserted gene. In the present context, such neighbouring sites are referred to as functionally equivalent sites. It is contemplated that the distance from the specific transposon integration site where such functionally equivalent sites may be found is within the range of 1 to 2000 base pairs.

In accordance with the invention, the gene coding for a desired gene product which is inserted into the above-defined site may be a homologous or a heterologous gene including a gene derived from a lactic acid bacterium.

The present invention provides in a further aspect a recombinant lactic acid bacterium comprising a gene coding for a desired gene product and operably linked thereto a lactic acid bacterial promoter not natively associated with the gene, the presence of said promoter resulting in the expression of the gene being altered as compared to the expression of the gene when operably linked to its native promoter.

As used herein, the term "altered expression" is used to indicate that the regulation of the expression of the gene quantitatively or qualitatively different from the regulation of the gene when operably linked to its native promoter. A quantitatively different expression may be recognizable as an increased level of expression of the gene products such as at least a 10% increased expression. It may e.g. be advantageous that the expression is increased by at least 25% such as at least 50%. In certain embodiments it may be advantageous to provide recombinant lactic acid bacteria in which expression of the gene coding for a desired gene product is less than that of the gene when under control of its native promoter. Accordingly, a useful recombinant bacterium may have an expression the level of which is at least 10% reduced, preferably at least 25% or more preferably at least 50% reduced.

Qualitatively, the expression of a gene coding for a desired gene product, the native promoter of which is a constitutive promoter may be altered by operably linking it to a regulatable promoter or the expression of a gene having a native regulatable promoter may be altered by linking it to a constitutive promoter. In further embodiments, the expression of a gene having a native regulatable promoter may be qualitatively altered by linking it to a regulatable promoter having a different mode of regulation.

In one useful embodiment, the present invention provides the recombinant lactic acid bacterium as one comprising an inserted lactic acid promoter-comprising DNA sequence as defined above, the lactic acid bacterial promoter being operably linked to a gene coding for a desired gene product. The gene coding for a desired gene product may in accordance with the invention be a chromosomal gene or an extrachromosomally located gene.

In certain preferred embodiments, the above gene coding for a desired gene product may be a native gene which in the present context is defined as a homologous gene which is in its natural position on a chromosome or on a plasmid naturally occurring in a particular lactic acid bacterium or it may be a homologous gene which is isolated from its natural position and reinserted into the same lactic acid bacterial strain, but in an other position. In still other useful embodiments, the gene coding for a desired gene product is a heterologous gene isolated from a non-lactic acid bacterial species or from an other lactic acid bacterial species.

Although it may in certain embodiments be preferred that the inserted promoter is a regulatable promoter, it may also in other useful embodiments be advantageous to provide a recombinant lactic acid bacterium wherein the inserted promoter is a constitutive promoter. When the selected promoter to be inserted is a regulatable promoter, the mode of regulation may be selected from the factors as defined hereinbefore, including regulation by a stochastic event.

It may be advantageous to provide the lactic acid bacterium according to the present invention as one in which an inserted DNA sequence comprising a lactic acid bacterial promoter is inserted into a plasmid. In certain preferred embodiments such a plasmid is one which further comprises a gene coding for a desired gene product as defined herein, a lactic acid bacterial replicon which is functional in a lactic acid bacterium, an insertion site allowing the DNA sequence to be inserted so that the gene coding for the desired gene product is operably linked to the promoter, whereby the gene can be transcribed when the plasmid is present in a lactic acid bacterium.

The promoter inserted into the plasmid may preferably be a promoter which is regulatable as it is described herein.

In this context, a suitable lactic acid bacterium is one harbouring the plasmid pAK80 which is described in the following or a derivative hereof including pAK80:SB, pAK80:143, pAK80:162, pAK80:163, pAK80:170, pAK80:224 and pAK80:242.

In an interesting embodiment, the lactic acid bacterium to be recombined in accordance with the present invention may carry the gene coding for a desired gene product on a plasmid having a conditional replication behaviour so that the plasmid copy number under certain conditions is substantially increased, e.g. to several hundreds or thousands. Plasmids having such a replication behaviour is also designated runaway plasmids.

A recombinant lactic acid bacterium as defined herein may be one which is selected from Lactococcus spp. including *Lactococcus lactis* ssp. *lactis*, *Lactococcus lactis* ssp. *diacetylactis* and *Lactococcus lactis* ssp. *cremoris*, Streptococcus spp. including *Streptococcus salivarius* ssp. *thermophilus*, Lactobacillus spp. including *Lactobacillus acidophilus*, *Lactobacillus plantarum*, *Lactobacillus delbrückii* ssp. *bulgaricus*, *Lactobacillus helveticus*, Leuconostoc spp. including *Leuconostoc oenos*, Pediococcus spp., Brevibacterium spp., Propionibacterium spp. and Bifidobacterium spp. including *Bifidobacterium bifidum*.

In preferred embodiments, the recombinant lactic acid bacterium is one in which the inserted promoter-containing sequence as defined herein is derived from Lactococcus spp. such as from *Lactoccus lactis* subspecies *lactis*., Streptococcus spp., Lactobacillus spp., Leuconostoc spp., Pediococcus spp., Brevibacterium spp., Propionibacterium spp. and Bifidobacterium spp. In certain specific embodiments, the inserted promoter may be isolated from *Lactoccus lactis* subspecies *lactis* strains MG1614, MG1363 or CHCC285

(Chr. Hansens Laboratorium A/S). Interesting promoters are tRNA and rRNA promoters including the PI and PII promoters and the purD promoter from *Lactoccus lactis* subspecies *lactis* as described in the following. Particularly interesting promoters are strong promoters such as tRNA or rRNA promoters which comprise the conserved sequence (motif) AGTT.

The present recombinant lactic acid bacterium is preferably one in which the gene coding for a desired gene product is selected from a gene coding for a lipase, a gene coding for a nuclease, a gene coding for a peptidase such as an aminopeptidase, a gene coding for a protease, a gene coding for a gene product involved in carbohydrate metabolism, a gene coding for a gene product involved in citrate metabolism, a gene coding for a gene product involved in bacteriophage resistance, a gene coding for a lytic enzyme such as lysozyme or a phage lytic enzyme and a gene coding for a bacteriocin including nisin. In an interesting aspect, the gene coding for a desired gene product may be one the gene product of which confer resistance to a bacteriocin sped as nisin, or pediocin.

The above genes coding for a desired gene product may be genes derived from a lactic acid bacterium or they may suitably be genes derived from a non-lactic acid bacterial microbial species or from a eucaryotic cell including plant cells and human or animal cells. As one example of a useful gene derived from a eucaryotic cell may be mentioned plasminogen.

In one specific preferred embodiment of the invention the gene is selected from the lacL gene of a Leuconostoc spp., the lacM gene of a Leuconostoc spp. and a *Lactococcus lactis* ssp. *lactis* gene coding for a peptidase such as a lysine aminopeptidase.

In accordance with the present invention the recombinant lactic acid bacterium as defined herein may suitably be one in which a gene coding for a desired gene product is inserted at a site in a replicon where it is under the control of a promoter present in the replicon, which site is identifiable by the insertion of a promoterless structural gene by means of a transposable element comprising the promoterless structural gene whereby the originally promoterless gene becomes expressible by being operably linked to the promoter present in said replicon, the insertion of the gene at said site having resulted in said gene becoming operably linked to the promoter being present in the replicon.

It will be understood that the site at which the gene coding for a desired gene product may be inserted is not limited to the specific site between two base pairs as identified by the insertion of the transposable element, but may be any site within a distance from this specific site which may still allow the lactic acid bacterial promoter to which the promoterless gene of the transposable element may become operably linked, to control the expression of the inserted gene. Insertion sites which are in such a distance from the specifically identified site may in the present context be referred to as functionally equivalent insertion sites.

There may also in accordance with the present invention be provided a recombinant lactic acid bacterium into which has been inserted a promoter-comprising sequence as defined above as well as a gene coding for a desired gene product also as defined above.

As mentioned above, the present invention provides in a still further aspect an isolated DNA fragment comprising (i) a regulatable lactic acid bacterial promoter which is functional in a lactic acid bacterium and operably linked thereto (ii) a gene coding for a desired gene product, said promoter being one which is not naturally associated with the gene and which confers to the gene coding for a desired gene product an altered expression as defined hereinbefore.

Such a DNA fragment is isolated in accordance with the method as described herein. In one useful embodiment the DNA fragment is one which further comprises at least one transcription terminator. The present DNA fragment is preferably a fragment having a size which is in the range of 100 to 10000 base pairs such as a size which is in the range of 200 to 5000 base pairs. In accordance with the invention, the DNA fragment may also be one which further comprises sequences coding for gene products involved in the regulation of the promoter.

In useful embodiments, the DNA fragment is one in which the gene coding for a desired gene product is selected from a gene coding for a lipase, a gene coding for a peptidase, a gene coding for a protease, a gene coding for a gene product involved in carbohydrate metabolism, a gene coding for a gene product involved in citrate metabolism, a gene coding for a gene product involved in bacteriophage resistance, a gene coding for a lytic enzyme and a gene coding for a bacteriocin. The gene may also be one which codes for a gene product conferring resistance to an antibiotic or a bacteriocin such as e.g. nisin or pediocin.

The DNA fragment as defined above may comprise a gene coding for a desired gene product which is a homologous or a heterologous gene including a gene derived from a lactic acid bacterium. Accordingly, the gene may in certain preferred embodiments be one which is selected from the lacL gene of a Leuconostoc spp., the lacM gene of a Leuconostoc spp. and a *Lactococcus lactis* ssp. *lactis* gene coding for a lysine aminopeptidase.

The lactic acid bacterial promoter comprised in the DNA fragment may be isolated from any lactic acid bacterial species as mentioned herein and may be a constitutive or regulatable promoter as also defined above. In specific embodiments of the invention the promoter is selected from the regulatable promoter contained in the *Lactococcus lactis* ssp. *lactis* MG1363 integrant clone P139-170 deposited under the accession number DSM 7360 and the promoter contained in the *Lactococcus lactis* ssp. *lactis* MG1614 integrant clone 63b deposited under the accession number DSM 7361.

The recombinant bacterium may in accordance with the invention be one in which the inserted DNA sequence comprising a regulatable lactic acid bacterial promoter is inserted into a vector comprising a promoterless gene coding for a desired gene product, a theta-replicating lactic acid bacterial replicon which is functional in the bacterium, an insertion site allowing the DNA sequence to be inserted so that the gene coding for the desired gene product is operably linked to the promoter, whereby the gene is transcribed. In one embodiment such a bacterium may as the vector into which the inserted DNA sequence is inserted comprise the plasmid pAK80.

The recombinant lactic acid bacterium as provided herein may be useful in starter cultures for the manufacturing of food products including dairy products, meat products and vegetable products and in the preservation of animal feed. In the latter context, the present recombinant bacteria are particularly interesting as inoculants in field crops which are to be ensiled. When the bacteria are to be used for these purposes they may conveniently be provided in the form of dried or frozen bacterial concentrates e.g. containing $10^{10}$ to $10^{12}$ colony forming units (CFUs) per g of concentrate.

An interesting use of a recombinant lactic acid bacterium as defined herein is in the manufacturing of a probiotically active composition. The term "probiotically active" indicates that the bacteria selected for this purpose have characteristics which enables them to colonize in the gastrointestinal tract and hereby exert a positive regulatory effect on the microbial flora in this habitat. Such effect may be recognizable as an improved food or feed conversion in human or animals to which the bacteria are administered, or as an increased resistance against invading pathogenic microorganisms.

Furthermore, it is contemplated that the present recombinant lactic acid bacteria may be useful in the preparation of recombinant vaccine strains in which one or more genes coding for antigenic determinants are inserted.

The recombinant plasmid according to the present invention is preferably one in which the lactic acid bacterial promoter is a promoter which is regulatable in a manner such as it has been defined hereinbefore. In this context useful plasmids may be selected from the plasmid pAK80 or a derivative hereof including pAK80:SB, pAK80:143, pAK80:162, pAK80:163, pAK80:170, pAK80:224 and pAK80:242.

BRIEF DESCRIPTION OF THE FIGURES

The invention is further illustrated in the following Examples and Figures, where:

FIG. 12 shows the gene organization and nucleotide sequence (SEQ ID NO:20) of trnA. The deduced amino acid sequence of tma (SEQ ID NO:21) is shown in one-letter code below, the stop codon indicated by an asterisk. Putative –35 and –10 promoter sequences (PI, PII), a conserved motif in the –44 region and a conserved sequence that might be involved in stringent control (Chiaruttini & Milet, 1993; Ogasawara et al., 1983) are double underlined. The coding regions of the tRNA genes and rrfU are underlined. Putative transcription terminators are indicated by arrows above the sequence. The location of restriction enzyme sites for ScaI and SpeI, used for the cloning and promoter cloning, is shown above the sequence, FIG. 13 shows a comparison of tRNA and rRNA promoter sequences from Lactococcus lactis and Lactococcus cremoris. The conserved –44 region, –35 region, a doublet TG (cf. reference 19), –10 and a conserved sequence suggested to be involved in control of expression during the stringent response of Bacillus subtilis (Ogasawara et al., 1983) are underlined. A (SEQ ID NO:22): PI of trnA; B (SEQ ID NO:24): PII of trnA; C(SEQ ID NO:24): P21 from a Lactococcus cremoris tRNA$^{leu}$ gene (van der Vossen et al., 1987; this study); D (SEQ ID NO:25): P2 from Lactococcus lactis (Koivula et al., 1991); E (SEQ ID NO:26): promoter region in front of a Lactococcus lactis ochre suppressor gene (F. Dickely & E. Bech Hansen, personal communication); F (SEQ ID NO:27): P10 from a Lactococcus lactis tRNA$^{arg}$ gene (Koivula et al., 1991; this study); G (SEQ ID NO:28): promoter of a Lactococcus lactis rRNA operon (Chiaruttini & Milet, 1993); H (SEQ ID NO:29): P2 from a Lactococcus lactis rRNA operon (Beresford & Condon, 1993); I (SEQ ID NO:30): putative promoter in front of a Lactococcus lactis amber suppressor gene (E. Johansen, unpublished results); J (SEQ ID NO:31): P21 from Lactococcus lactis (Koivula et al., 1991). Con., shows identical nucleotides in the aligned sequences A to H, FIG. 14 is a 846 bp DNA fragment (SEQ ID NO:32) from Lactococcus lactis containing the entire purD promoter region as well as an adjacent promoter initiating transcription in the opposite direction, (SEQ ID NO:33 is also shown in this Figure)

EXAMPLE 1

Figure 1:
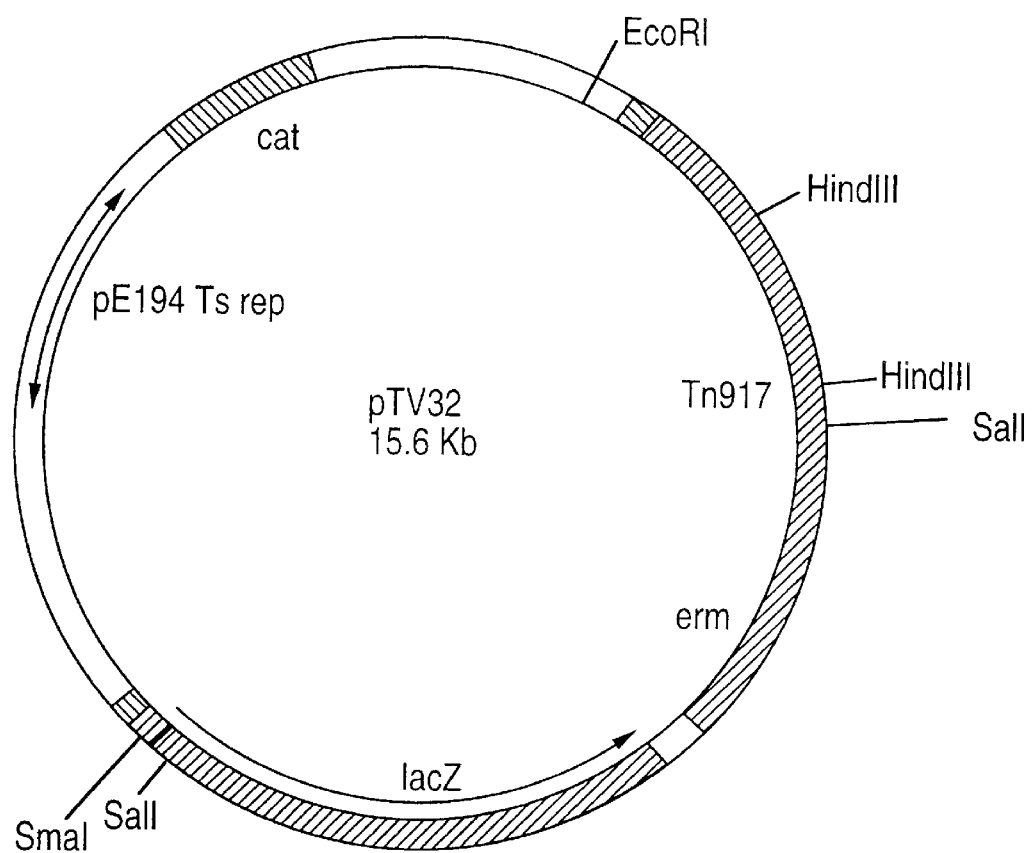
FIG. 1 is a map of pTV32 in which the following abbreviations indicate restriction enzyme sites: SalI, EcoRI, PstI, XbaI, KnpI and SmaI, Tn917 indicates the transposon part, erm indicates the gene coding for erythromycin resistance, bla the gene coding for β-lactamase, ColEI rep the origin of replication of the ColEI plasmid, cat indicate the gene coding for chloramphenicol acetyltransferase mediating resistance to chloramphenicol, lacZ the promoterless β-galactosidase gene or E. coli, tet indicates the gene coding for tetracycline resistance and pE194 Ts rep indicates the temperature sensitive origin of replication derived from plasmid pE194.
Figure 2:
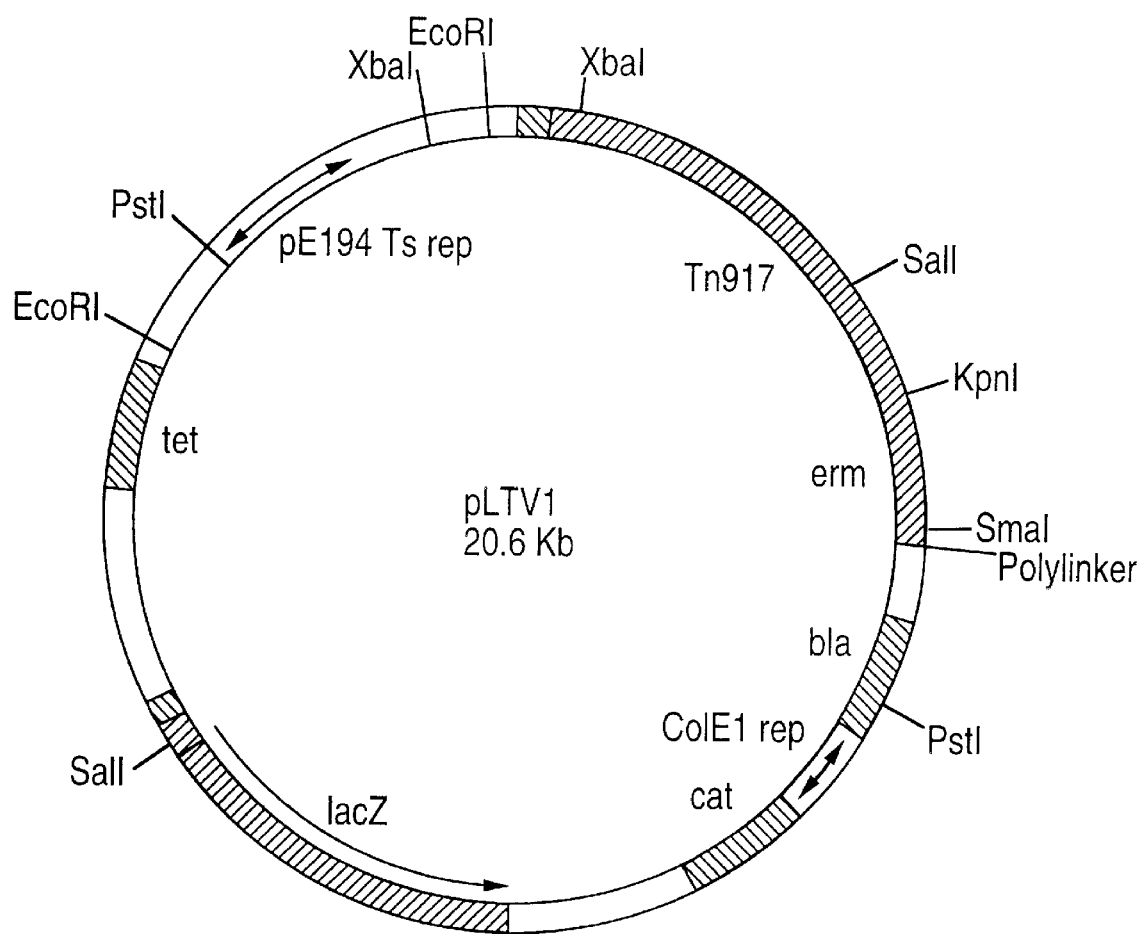
FIG. 2 is a map of pLTV1 (abbreviations, cf. the legend to FIG. 1)

Transformation of *Lactococcus lactis* ssp. *lactis* MG1614 with pTV32 and pLTV1 and demonstration of replication of these plasmids Several vectors (pTV plasmids) containing derivatives of the transposon Tn917 from the lactic acid bacterial species *Streptococcus faecalis* have been constructed for use in *Bacillus subtilis* and other gram-positive bacteria (references 10, 55 and 57). Two derivatives of the pTV plasmid series, pTV32 (reference 57) and pLTV1 (reference 55) were selected for this and the following experiments.

pTV32 (15.6 kb) and PLTV1 (20.6 kb) contain (i) a temperature sensitive replicon (pE194Ts-rep) from the plasmid E194, (ii) on the replicon part of the plasmid, a cat gene (pTV32) which confers chloramphenicol resistance ($Cm^r$) or tetracycline resistance ($Tc^r$) gene (pLTV1), (iii) Tn917 harbouring an erm gene which confers erythromycin resistance ($Em^r$), and (iv) a promoterless *E. coli* lacZ gene with a ribosomal binding site from *Bacillus subtilis* inserted in non-essential Tn917 DNA at the erm-proximal end (FIGS. 1 and 2). pTV32 and PLTV1 were isolated from *E. coli* PY1173 and *Bacillus subtilis* PY258, respectively. These strains were obtained from P. Youngman, University of Pennsylvania.

*Lactococcus lactis* ssp. *lactis* MG1614 which is a prophage-free, plasmid-free, streptomycin- and rifampicin resistant derivative of strain NCDO 712 was transformed with pTV32 or pLTV1 using the electroporation method described by Holo and Ness (reference 20) and primary transformants were selected by plating onto M17 medium (Sigma Chemical Co.) containing 0.5% glucose (GM17 medium) supplemented with 0.5M sucrose, 2 mM $CaCl_2$ (SGM17,Ca medium) and the appropriate selective antibiotic (erythromycin or chloramphenicol) and incubated at 30° C. The antibiotics were purchased from Sigma and were used at the following concentrations: erythromycin, 1.0 μg $ml^{-1}$; chloramphenicol, 5.0 μg $ml^{-1}$.

With either plasmid, the transformation efficiencies were $10^4$ to $5 \times 10^4$ transformants per μg of DNA when selecting for $Cm^r$ or $Em^r$.

Selected primary transformant colonies were transferred to GM17 liquid medium supplemented with 5.0 μg $ml^{-1}$ of chloramphenicol and the transformant cells were grown up till a number of generations being in the range of 10 to 50. Plasmid DNA was subsequently extracted from these transformants by performing an alkaline lysis of the cells substantially in accordance with the method described by Birnboim et al. (reference 6) with modifications as indicated in the following. Cells were grown exponentially to an $A_{600}$ of 0.3, and 5 ml cultures were harvested by centrifugation at 4,000×g. Pellets were washed in TS buffer (25% sucrose, 50 mM Tris hydrochloride, pH 8.0), resuspended in 0.25 ml S1 solution (5 mM EDTA, 50 mM NaCl, 25% sucrose, 50 mM Tris hydrochloride, pH 8.0) with 10 mg/ml lysozyme and incubated at 30° C. for 30 min. 0.5 ml S2 solution (0.2M NaOH, 1% SDS) was gently added and the suspension kept on ice for 5 min. Subsequently 0.4 ml 3M sodium acetate pH 4.8 was added and the suspension kept on ice for 5 min. Following centrifugation of the suspension at 10,000×g, plasmids were extracted from the supernatant in accordance with the method described by Birnboim et al (reference 6).

A portion of the thus extracted plasmid DNA and plasmids pTV32 and pLTV1 isolated from *E. coli* PY1173 and *Bacillus subtilis* PY258, respectively were subjected to a treatment under standard conditions with the restriction enzymes EcoRI, SalI and HindIII. Undigested extracted plasmid DNA isolated from *Lactococcus lactis* ssp. *lactis* MG1614 and from *E. coli* PY1173 and *Bacillus subtilis* PY258 as well as the restriction enzyme treated plasmid DNA were then subjected to an agarose gel electrophoresis analysis and it was found that the sizes of pTV32 and pLTV1 extracted from the transformed *Lactococcus lactis* ssp. *lactis* MG1614 as well as the restriction enzyme sites EcoRI, SalI and Hind III were retained as compared to with the original plasmids. By assuming that the level of recovery in the above plasmid preparation procedure was 100%, the average copy number of both the plasmids in the transformed *Lactococcus lactis* ssp. *lactis* MG1614 was estimated to be 6 to 12 copies per cell by performing a comparison on agarose gels with a standard of phage lambda DNA of known concentration digested with HindIII. Accordingly, it could be concluded from this experiment that lactic acid bacteria may be transformed with pTV32 and pLTV1 at a high efficiency and that these plasmids are capable of replicating in a lactic acid bacterium.

EXAMPLE 2

Induction of Tn917 transposition in *L. lactis* ssp. *lactis* and curing for DTV-plasmids

*Lactococcus lactis* ssp. *lactis* MC1614 ceases to grow in M17 broth (Sigma Chemical Co.) containing 0.5 glucose at temperatures exceeding 37° C. Since pTV32 or pLTV1 could be extracted from *L. lactis* ssp. *lactis* MG1614 transformed with these plasmids and grown at 37° C. under selection for $Cm^r$, the temperature curing procedure developed for *B. subtilis* could not be used in the Lactococcus strain.

However, it was demonstrated that neither pTV32 DNA nor pLTV1 DNA could be extracted from Lactococcus transformants grown at 30° C. with selection for $Em^r$. This indicated transposition (integration) of Tn917 to the chromosome with concomitant loss of plasmid.

Production of independent *Lactococcus lactis* ssp. *lactis* Tn917 integrants from individual cultures were carried out according to the following procedure:

Primary transformed cells prepared as described in Example 1 were plated on SGM17,Ca agar containing erythromycin and incubated at 30° C. for about 40 hours. 12 single colonies were subcultured twice in M17 broth medium selecting for $Em^r$. In order to obtain single colonies each culture was streaked on GM17 agar containing erythromycin and a single colony from each culture was restreaked once. All incubations were done at 30° C.

To verify that these assumed independent integrants had lost the plasmids as free molecules and had Tn917 inserted in the chromosome, a Southern hybridization was carried out on DNA from the 12 independent $Em^r$ MG1614 clones initially transformed with pTV32 and subcultured twice in liquid medium selecting for $Em^r$. From the isolates, the total DNA content was extracted from 100 ml cultures by harvesting the cells by centrifugation at 7000 rpm for 10 minutes. The cells were washed in TE buffer (10 mM Tris hydrochloride, 1 mM EDTA pH 7.5) and harvested. The pellets were frozen at −20° C. and subsequently dissolved in 3 ml STET buffer ( 8 w/v % sucrose, 5 v/v % Triton X-100, 50 mM EDTA [pH 8.0], 50 mM Tris hydrochloride (pH 8.0]. 750 µl lysozyme (10 mg/ml) was added and the solution incubated at 37° C. for 1 hour. 750 µl of 10% SDS was added and incubation continued at 37° C. for ½ hour followed by incubation at 65° C. for ½ hour. Two ml of TE buffer was added and the aqueous solution extracted three times with 5 ml phenol:chloroform (1:1). To the suspension ¹/₁₀ volume of 5M NaCl and 1 volume of isopropanol was added. The solution was mixed very carefully until DNA precipitated as long white threads. The DNA was wound on an inoculation needle and transferred to Eppendorf tubes and washed 3 times in 70% ethanol. The DNA was dissolved in 500 µl of TE buffer.

1 µg of the thus prepared DNA from each isolate was digested with EcoRI and separated by electrophoresis through 1.0% agarose gels and transferred to Hybond-N membranes (Amersham, UK) and subjected to hybridization using two $^{32}$P-labelled DNA probes, viz pLTV1 and a 4 kb EcoRI fragment of pLTV1 containing the pE194 replicon. The 4 kb fragment was isolated from agarose gels by electroelution into dialysis bags. The probes were nick translated with [α-$^{32}$P]dCTP (Amersham, UK). The restriction enzyme digestion, electrophoresis, DNA transfer, nick translations and hybridizations were done as described by Maniatis at al. (reference 34).

Figure 3A:
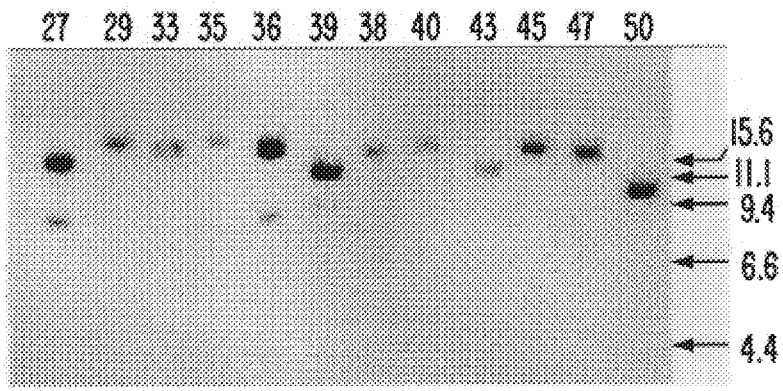
FIGS. 3A–3B illustrates Southern hybridization analysis of 12 independent L. lactis ssp. lactis TV32 integrants. DNA from integrants, indicated on top of each lane, was digested with EcoRI, electrophoresed through an agarose gel, transferred to a nylon membrane and hybridized with A: $^{32}$p labelled pLTV1. B: $^{32}$p labelled pE194 replicon-specific probe. Size markers are given in kilobase pairs.
Figure 3B:
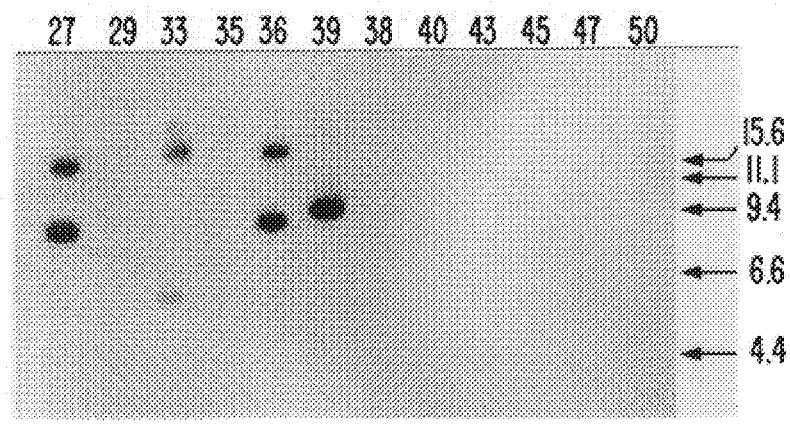

The integrant clones hybridized with the $^{32}$P-labelled pLTV1 and/or the pTV replicon-specific probe as illustrated in FIG. 3. pTV32 is 15.6 kb and has a unique EcoRI site which is located in the replicon part of the plasmid. The Tn917 part of pTV32 is 8 kb. From 8 out of the 12 TV32 integrants a single signal was detected with pLTV1 as the probe (FIG. 3A) whereas no signal was seen with the pTV-replicon specific probe (FIG. 3B). These 8 integrants were Em$^r$ and Cm$^s$ as would be expected if TV32 had transposed to the chromosome and pTV32 was lost. From the remaining four integrants (number 27, 33, 36 and 39) two signals were detected with pLTV1 as the probe (FIG. 3A). The same two bands hybridized with the replicon specific probe and no signal of the size expected for freely replicating pTV32 was observed (FIG. 3B). Accordingly, these four strains had DNA from the replicon part of pTV32 integrated into the chromosome together with the transposon TV32. In each of the four integrants, the DNA from the replicon part included the cat gene, since all four were Cm$^r$.

EXAMPLE 3

Demonstration of quasi-randomness of Tn917 insertion into the *Lactococcus lactis* ssp. *lactis* MG1614 chromosome In order for Tn917 to be used as an efficient mutagenesis tool in *L. lactis* ssp. *lactis*, insertions of the transposon should be random. An analysis of transposition randomness was carried out by determination of the physical location of TV32 on chromosomal SmaI fragments of 61 independent MG1614 TV32 integrants which were prepared according to the method as described in Example 2. The preparation and SmaI in situ restriction enzyme digestion of genomic DNA was done as described by Tanskanen et al. (reference 52). Of these integrants, tegrants, 10 expressed β-galactosidase as shown by plating on GM agar supplemented with 160 µg/ml of X-gal.

The SmaI restriction fragments were separated by pulsed-field gel electrophoresis (PFGE) using a model CHEF-DR II apparatus (Bio Rad Laboratories, Richmond, Calif.). The gels were 1.5% agarose gels in 0.5×TBE (1×TBE in 89 mM boric acid, 2 mM EDTA and 89 mM Tris borate [pH 8.3]. The electrophoresis parameters were as follows: 175V for 20 hours at 14° C. with ramped pulse times for 1 to 70 seconds. The gels were stained with an ethidium bromide solution (1 mg/ml) in 0.5×TBE for 30 minutes, destained for 4 hours in 0.5×TBE and photographed using a UV transilluminator.

The MG1614 chromosome digested with SmaI generated the following ten fragments larger than 45 kb (FIG. 4, lane 3): 600, 310, 280, 200, 175, 175, 140, 120, 105 and 65 kb. TV32 contains a unique SmaI site. The insertion of TV32 into any of the ten large SmaI fragments was therefore detectable on pulsed-field gel electrophoresis (PFGE) gels unless the insertion was located close to the fragment end.

The TV32 locations on the SmaI fragments of the 61 integrants are given in Table 1.

TABLE 1

Random *Lactococcus lactis* ssp. *lactis* TV32 integrants divided into groups on the basis of the physical location of TV32 on chromosomal SmaI fragments

| Group | TV32 target: chromosomal SmaI fragment (kb) | Fragment lengths (kb) of SmaI-digested target fragments with inserted TV32$^a$ | Group members (integrant No.)$^b$ |
|---|---|---|---|
| 1 | 600 | 540 + 70 (= 610) | 70b |
| 2 | 600 | 535 + 75 (= 610) | 21, 44 |
| 3 | 600 | 530 + 80 (= 610) | 4, 27, 31 |
| 4 | 600 | 525 + 85 (= 610) | 39, 49 |
| 5 | 600 | 505 + 105 (= 610) | 22 |
| 6 | 600 | 485 + 125 (= 610) | 3, 30 |
| 7 | 600 | 470 + 140 (= 610) | 34 |
| 8 | 600 | 460 + 145 (= 605) | 35, 40, 54 |
| 9 | 600 | 450 + 160 (= 610) | 41, 42 |
| 10 | 600 | 445 + 165 (= 610) | 61b, 62b, 68b |
| 11 | 600 | 440 + 170 (= 615) | 33 |
| 12 | 600 | 405 + 200 (= 605) | 1, 20 |
| 13 | 600 | 390 + 205 (= 605) | 6 |
| 14 | 600 | 380 + 225 (= 605) | 12 |
| 15 | 600 | 375 + 230 (= 605) | 10, 43 |
| 16 | 600 | 360 + 235 (= 595) | 11, 23, 65b |
| 17 | 600 | 355 + 240 (= 595) | 50 |
| 18 | 600 | 350 + 245 (= 595) | 16, 64b |
| 19 | 600 | 325 + 280 (= 605) | 66b |
| 20 | 600 | 310 + 300 (= 610) | 25, 38 |
| 21 | 310 | 245 + 65 (= 310) | 45 |
| 22 | 310 | 185 + 135 (= 320) | 60 |
| 23 | 310 | 180 + 140 (= 320) | 8 |
| 24 | 200 | 150 + x | 19$^c$ |
|  | 600 | 420 + 210 (= 630) |  |
| 25 | 175 | 155 + x | 29 |
| 26 | 175 | 140 + x | 47 |
| 27 | 175 | 105 + 75 (= 180) | 24 |
| 28 | 140 | 115 + x | 13, 15 |
| 29 | 140 | 110 + x | 2, 26, 63b |
| 30 | 140 | 105 + x | 18, 32, 51, 59 |
| 31 | 140 | 100 + x | 14 |
| 32 | 140 | 90 + x | 7 |
| 33 | 140 | 85 + x | 5, 36 |
| 34 | 120 | 115 + x | 69b |
| 35 | 120 | 110 + x | 48 |
| 36 | 120 | 105 + x | 55 |
| 37 | 120 | 90 + x | 67b |
| 38 | ND$^d$ |  | 46 |

$^a$x indicates a fragment that could not be detected on PFGE gels.
$^b$Clones whose designations end with b are blue on plates containing 5-bromo-4-chloro-3-indolyl-β-D-galactopyranoside.
$^c$Double integrant.
$^d$ND, not determined.

Figure 4A:
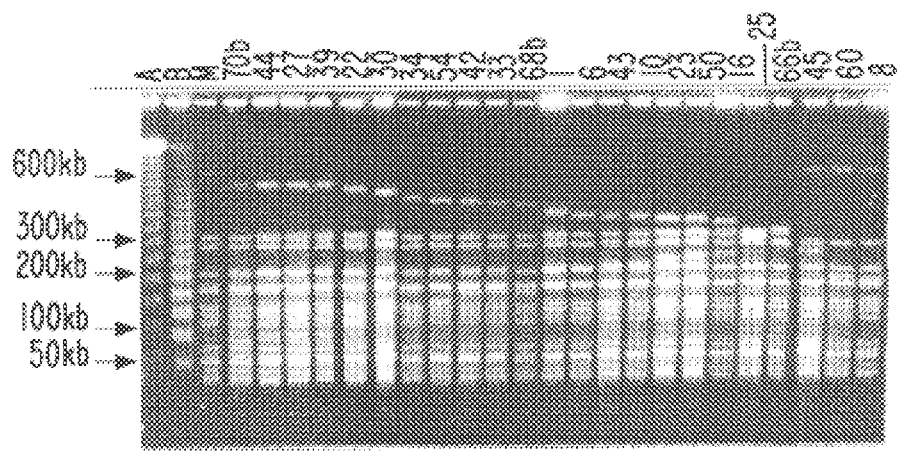
FIG. 4A–4B show pulsed-field gel electrophoresis (PFGE) of SmaI-digested DNA from L. lactis ssp. lactis TV32 integrants. Integrant numbers are indicated on top of the lanes. A: lambda ladder (Promega, Madison, U.S.A.) starting from the bottom with 48.5 kb, 97.0 kb, 145.5 kb etc. B: delta 39 lambda ladder (Promega) starting from the bottom with 39.0 kb, 78.0 kb, 117 kb etc. M is SmaI-digested DNA from L. lactis ssp. lactis MG1614.
Figure 4B:
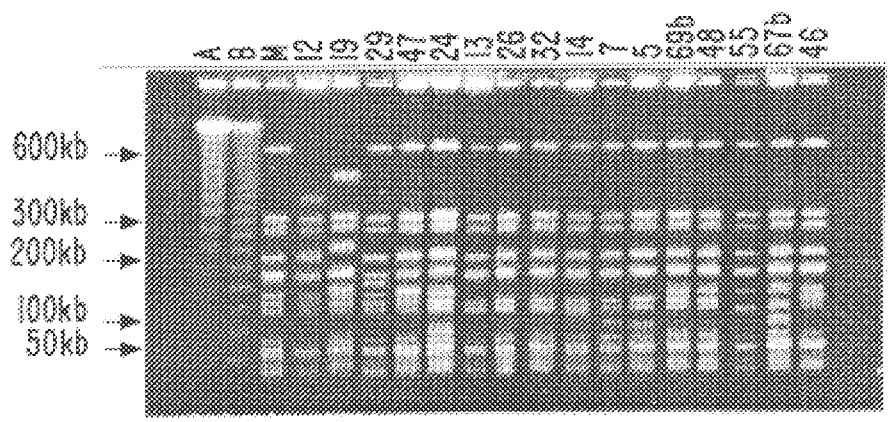

Based on the physical location of TV32 on the SmaI fragments, the 61 integrants could be divided into 38 groups. FIG. 4 shows PFGE of integrants representing each of the groups listed in Table 1. One group (No. 30) contained four integrants, five groups (Nos. 3, 8, 10, 16 and 29) contained three integrants and ten groups (Nos. 2, 4, 6, 9, 12, 15, 18, 120, 28 and 33) contained two integrants. However, members of the same integrant group do not necessarily carry the TV32 at the same position on the fragment. Insertions located symmetrically on a fragment are indistinguishable on PFGE gels and the limit of resolution varies from two to ten kb depending on the fragment length.

The 600, 310, 200, 175, 140 and 120 kb chromosomal SmaI fragments had all been targeted by TV32 (Table 1 and FIG. 4). Apparently none of the integrants carried insertions in the 280, 105 and 65 kb fragments. However, it could not be established from the PFGE data if the TV32 in integrant 46 resided at the end of a fragment larger than 45 kb or in any position on a fragment smaller than 65 kb in size. Integrant 19 contained a double insertion (FIG. 4). Two TV32 copies are carried on the 200 kb and the 600 kb fragments, respectively. These double insertions make the total number of insertion events in this study 62.

The 62 TV32 insertions in the *Lactococcus lactis* ssp. *lactis* chromosome were not evenly distributed along the chromosome. This was revealed by a chi-square analysis whereby it was tested whether the probability of insertion into a SmaI fragment was dependent only on the length of the fragment (Table 2).

Table 2 gives the number of integrants obtained in each fragment, together with the expected number of integrants assuming that the probability of integration into a fragment is dependent only on the length of the fragment. A chi-square test was used to test this assumption. The chi-square test showed ($P<0.005$) that the insertions obtained were not absolutely randomly distributed on the chromosome. The major contribution to this unevenness came from a 2.5-fold overrepresentation of insertions into the 600 kb fragment and an absence of insertions into 280 kb fragment. The 37 insertions into the 600 kb fragment were located at least 21 different positions with no more than 3 insertions at the same position. These results indicate that the above overrepresentation cannot not be due to a single dominating hot spot. The 280 kb fragment is not totally refractory to TV32 insertions, since such integrants were obtained in parallel experiments. Accordingly, in the present context the TV32 insertion distribution pattern as obtained in *Lactococcus lactis* ssp. *lactis* strain MG1614 is designated as "quasi-random".

The following factors may have contributed to the observed uneven distribution of insertions: (1) fragments near the chromosomal origin of replication have higher copy numbers than fragments near the terminus; (2) essential genes may have been unevenly distributed; and (3) Tn917 might become preferentially inserted into regions with particular features.

TABLE 2

Distribution of TV32 on chromosomal *Lactococcus lactis* ssp. *lactis* SmaI fragments

| TV32 target: chromosomal SmaI fragment (kb)[a] | No. of insertions observed[b] | No. of insertions expected[c] | No. of insertions observed/ No. of insertions expected | Chi-square test[d] |
|---|---|---|---|---|
| 600 | 37 | 14.9 | 2.5 | 32.8 |
| 175[e] | 3 | 8.7 | 0.3 | 3.7 |
| 310 | 3 | 7.7 | 0.4 | 2.9 |
| 280 | 0 | 6.9 | 0.0 | 6.0 |
| 200 | 1 | 5.0 | 0.2 | 3.2 |
| 140 | 13 | 3.5 | 3.7 | |
| 120 | 4 | 3.0 | 1.3 | |
| 105 | 0 | 2.6 | 0.0 | 0.0 |
| 65 | 0 | 1.6 | 0.0 | |
| <45 | 1 | 8.2 | 0.1 | |

[a]The total for the chromosomal SmaI fragment sizes was 2500 kb
[b]The total number of insertions observed was 62
[c]The probability of insertion was assumed to equal fragment size relative to chromosome size. The total number of insertions expected was 62.1.
[d]Values were calculated as follows: (number of insertions observed − number of insertions expected)[2]/number of insertions expected. The chi-square test requires the expected number for each class to exceed or equal 5; therefore, insertions in fragments smaller than 205 kb were treated as one. The total chi-square value was 49.5. In a qui-square test with 5 degrees of freedom, the probability of exceeding 16.7 is 0.005 (0.5%) if the hypothesis is correct.
[e]Strain MG1614 had two 175 kb fragments which could not be differentiated on PFGE gels. Accordingly, insertions into these fragments were treated as one class.

Despite the somewhat uneven distribution of TV32 insertions into the *Lactococcus lactis* ssp. *lactis* MG1614 chromosome it was concluded that the Tn917 derivatives are very useful tools for the genetic analysis of lactic acid bacteria, since it was also found in further experiments that a large number of insertion sites in addition to those mentioned above, could by found with these transposon derivatives.

The above *Lactococcus lactis* ssp. *lactis* MG1614 clone designated 63b was deposited on 21 Dec. 1992 with the DSM-Deutsche Sammlung von Mikroorganismen und Cellkulturen GmbH, Mascheroder Weg 1b, D-38124 Braunschweig, Germany under the accession number DSM 7361.

EXAMPLE 4

Production of a collection of Tn917 insertions in *Lactococcus lactis*

Figure 5:
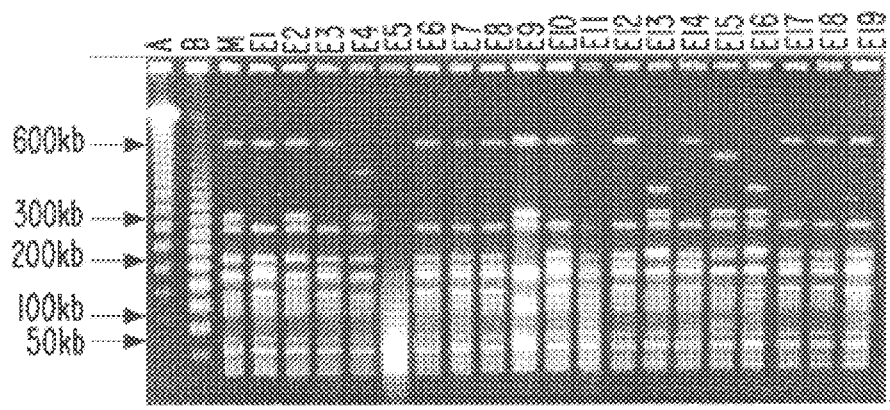
FIG. 5 illustrates pulsed-field gel electrophoresis (PFGE) of 19 clones (E1-E19) picked from a culture of Lactococcus lactis ssp. lactis MG1614 comprising a dominant TV32 integrant. Lanes indicated by A, B and M are as indicated above for FIG. 5. The digestion of clone E5 resulted in fragments which could not be visualized as discrete bands.

In order to prepare a collection of Tn917 insertions in *Lactococcus lactis*, the following procedure was followed:

A single colony of a pTV32-containing *Lactococcus lactis* ssp. *lactis* strain MG1614 was inoculated into GM17 medium and grown for 8 to 10 generations with selection for Cm[r]. One per cent of these cells were grown for 8 to 10 generations in GM17 medium with selection for Em[r]. The temperature was kept at 30° C. The resulting cells were plated onto GM17 agar plates with selection for Em[r]. 19 colonies were randomly picked and preparation and digestion of genomic DNA in situ in agarose blocks were done as described in Example 3. FIG. 5 and table 3 show that 12 out of 18 (digestion one clone resulted in fragments which could be visualized as discrete bands) clones had the transposon inserted at the same location on the chromosome indicating that the culture was dominated by a single integrant.

TABLE 3

L. lactis ssp. lactis MG1614 TV32 integrants from a culture containing a dominant integrant

| Group | TV32 target: chromosomal SmaI fragment (kb) | Fragment length (kb) of SmaI-digested target fragments with inserted TV32[a)] | Group member (integrant No.) |
|---|---|---|---|
| 1 | 600 | 540 + 70 (= 610) | E15 |
| 2 | 600 | 475 + x | E4 |
| 3 | 600 | 400 + 210 (= 610) | E13, E16 |
| 4 | 310 | 190 + 140 (= 330) | E1, E3, E6, E7, E8, E10, E11, E12, E14, E17, E18, E19 |
| 5 | 200 | x + x | E9[b)] |
|  | 140 | x + x |  |
| 6 | 175 | 160 + x | E2 |

Figure 6:
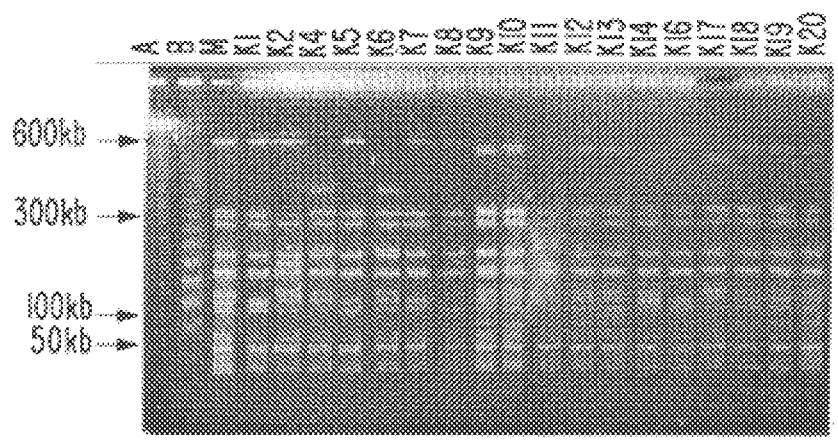
FIG. 6 illustrates pulsed-field gel electrophoresis (PFGE) of 18 clones (K1-K2, K4-K14, K16-K20) picked randomly from a pooled culture of Lactococcus lactis ssp. lactis MG1614 TV32 integrants. Lanes indicated by A, B and M are as indicated above for FIG. 5.

[a)]indicates a fragment that could not be detected on PFGE gels
[b)]Double integrant To circumvent a dominant integrant in a culture, the following procedure was selected:

Strain MG1614 was transformed with pTV32 as described in Example 1. The transformed cells were plated onto SGM17 agar plates containing 1 μg/ml of erythromycin. Following incubation at 30° C. for 48 hours, 20 plates each with about 100 colonies were replica-plated onto plates of GM17 agar with selection for Em[r]. The replicated plates were incubated at 30° C. for 30 hours. The replication step was repeated and the colonies were washed off and pooled. From the pooled culture, 18 integrants were randomly selected and analyzed by PFGE as defined above. On the basis of the location of the Tn917 insertions on chromosomal SmaI fragments, the 18 integrants were divided into 13 groups of which none contained more than 2 insertions (FIG. 6 and table 4). It was therefore concluded that the pooled culture contained a collection of quasi-randomly transposon TV32-insertions in strain MG1614.

TABLE 4

Lactococcus lactis ssp. lactis MG1614 TV32 integrants from a culture containing quasi-random TV32 insertions

| Group | TV32 target: chromosomal SmaI fragment (kb) | Fragment length (kb) of SmaI-digested target fragments with inserted TV32[a)] | Group member (integrant No.) |
|---|---|---|---|
| 1 | 600 | 540 + 70 (= 610) | K10, K20 |
| 2 | 600 | 530 + 80 (= 610) | K3, K12 |
| 3 | 600 | 520 + 90 (= 610) | K9, K18 |
| 4 | 600 | 510 + 100 (= 610) | K13 |
| 5 | 600 | 470 + 120 (= 590) | K14 |
| 6 | 600 | 460 + 140 (= 600) | K17 |
| 7 | 600 | 375 + 220 (= 595) | K4, K6 |
| 8 | 310 | 185 + 140 (= 325) | K2 |
| 9 | 200 | 175 + x | K11 |
| 10 | 140 | 110 + x | K1 |
| 11 | 140 | 105 + x | K5, K16 |
| 12 | 140 | x + x | K7 |
| 13 | 120 | x + x | k8 |

[a)]indicates a fragment that could not be detected on PFGE gels

Sterile glycerol was added to the pooled culture at a concentration of up till 25% and this mixture stored −80° C.

A pooled culture containing a collection of quasi-random LTV1 insertions in Lactococcus lactis ssp. lactis MG1363 was prepared essentially as described above. However, before the washing off and pooling of the colonies the following was carried out:

320 μg/ml of X-gal was added to the plates used for the second replication. 242 colonies with varying blue intensities were seen on the second replication plate. In contrast less than 5% of these colonies were blue on GM17 agar plates containing 40 μg/ml of X-gal incubated for more than 48 hours. (40 μg/ml of X-gal is the standard concentration for identification of lacZ expression in E. coli). Each of the 242 blue colonies appearing on the plate containing 320 μg/ml of X-gal were restreaked to obtain single colonies on GM17 containing 1 μg/ml of erythromycin and 320 μg/ml of X-gal followed by restreaking once on the same medium. A single colony from each of these subcultures was inoculated into liquid GM17 medium supplemented with 1 μg/ml of erythromycin and incubated overnight at 30° C. and sterile glycerol added at a concentration of 25% to each of these subcultures for storage at −80° C. These 242 clones are referred to in the following as promoter fusion collection no. 1 (PFC-1).

One of the Lactococcus lactis ssp. lactis MG1363 PFC-1 clones with the designation P139-170 was deposited with the DSM-Deutsche Sammlung von Mikroorganismen und Cellkulturen GmbH, Mascheroder Weg 1b, D-38124 Braunschweig, Germany on 21 Dec., 1992 under the accession number DSM 7360.

EXAMPLE 5

Identification and cloning of regulatable promoters from the Lactococcus lactis ssp. lactis chromosome The collection of quasi-random Tn917 insertions in the Lactococcus lactis ssp. lactis MG1363 chromosome prepared as described in Example 4 (PFC-1) was used in this experiment which was designed as a screening for the presence of regulatable promoters in these fragments.

Temperature/growth phase regulated lacZ expression

Figure 7:
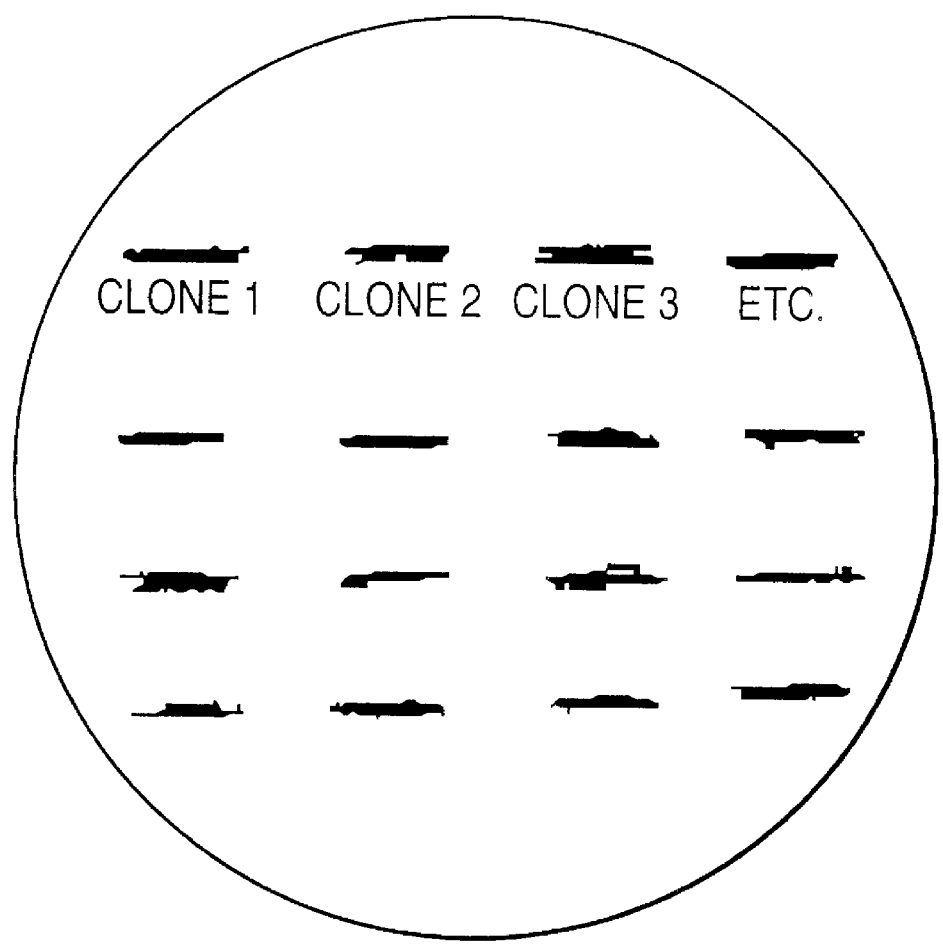
FIG. 7 shows the streak pattern for investigation of regulated lacZ expression in promoter fusion clone collection no. 1. Each clone was streaked onto a plate containing 1 μg/ml erythromycin and 320 μg/ml of X-gal in a straight line of about 0.5 cm.

Each clone from PFC-1 was streaked onto a duplicate set of GM17 plates containing 1 μg/ml of erythromycin and 320 μg/ml of X-gal. The streak pattern is shown in FIG. 7. On one set of plates, the clones were streaked and incubated at 15° C. on day 1. On the second set of plates, the clones were streaked and incubated at 30° C. on day 4. On day 5, both sets of plates were inspected. Three main types of lacZ expression were observed for the PFC-1 clones:

(i) Type 1T showing high lacZ expression (dark blue streak) at 30° C. and low or no lacZ expression (light blue or white streak) at 15° C.

(ii) Type 2T showing similar level of lacZ expression at the two temperatures (iii) Type 3T showing low or no lacZ expression at 30° C. and high lacZ expression at 15° C.

Out of a total of 242 clones tested, 23 were of the 1T type, 215 of the 2T type and 4 clones were of the 3T type. Due to the prolonged growth period at 15° C., it is not possible to determine whether the regulated lacZ expression is a function of the growth phase/-rate and/or of the temperature.

Arginine/pH-regulated lacZ expression

Each clone of PFC-1 was streaked onto a set of M17 plates containing 0.1% of glucose, 0.5% of arginine, 1 μg/ml of erythromycin and 320 μg/ml of X-gal and onto a set of GM17 plates containing 1 μg/ml of erythromycin and 320 μg/ml of X-gal using the same streak pattern as described above. Both sets of plates were incubated at 30° C. for about 30 hours. Three main types of lacZ expression were observed on the incubated plates:

(i) Type 1A showing high lacZ expression on plates without supplementation with arginine and low or no lacZ expression on plates supplemented with arginine (ii) Type 2A showing similar lacZ expression irrespective of arginine supplementation (iii) Type 3A showing low or no lacZ expression on plates without arginine and high lacZ expression on the plates supplemented with arginine Out of 242 clones tested, 21 were of type 1A, 219 were the 2A type and 2 clones of the 3A type. The pH of sterile GM17 is about 6.8. The pH in GM17 medium inoculated with *Lactococcus lactis* ssp. *lactis* and incubated overnight is about 5.0. However, the pH in M17 supplemented with 0.1% glucose and 0.5% arginine inoculated with *Lactococcus lactis* ssp. *lactis* and grown overnight exceeds 9.0. Accordingly, the regulated lacZ expression observed is a function of arginine concentration and/or pH in the medium.

NaCl/ion strength regulation of lacZ expression

Each clone of the PFC-1 collection was streaked onto a set of GM17 plates supplemented with 1 µg/ml of erythromycin, 320 µg/ml of X-gal and 2% of NaCl and on a set of plates with the same medium but without NaCl using the same streaking pattern as defined above. Both set of plates were incubated at 30° C. for about 30 hours. Two main types of lacZ expression were observed:

(i) Type 1S showing high lacZ expression on plates without NaCl and low or no lacZ expression on plates supplemented with NaCl (ii) Type 2S showing similar lacZ expression on both types of plates Out of 242 clones tested, 87 were of the 1S type and 155 of the 2S type.

When a clone from PFC-1 has been shown to have regulatable lacZ expression, an insertion point or a range on the Lactococcus chromosome is defined where an inserted gen will be regulatably expressed in Lactococcus. For example, the clone designated P139-170 of PFC-1 is of type 3T, type 1A and type 2S which indicates that the lacZ gene resides at a position where expression of an inserted gene is suppressed partly or totally at 30° C. and on M17 plates supplemented with arginine. However, the gene expression at this position is high at 15° C. on GM17 plates. The gene expression level on GM17 plates is unaffected by the tested concentration of NaCl.

Physiological investigation of the regulatable lacZ expression of P139-170 clone P139-170 was shown to be of the type 1A. The following pre-experiment was carried out to study the pH dependence of lacZ expression in this clone.

Six fermenters each containing 1 liter of GM17 medium supplemented with 1 µg/ml of erythromycin were set to operate at 30° C. The fermenters in duplicate were set to operate at pH 5.5, 6.5 and 7.5, respectively using 5M sulphuric acid or 5M sodium hydroxide. One of the duplicate fermenters was inoculated with 1% overnight culture of H25A (strain MG1614 containing an LTV1 insertion on the chromosome and capable of expressing β-galactosidase on GM17 agar regardless of added arginine or NaCl) and the other duplicate fermenters were inoculated with 1% of an overnight culture of P139-170.

The growth of the clones in the fermenters were followed by measuring OD$_{600}$ and plating onto GM17 plates ±1 µg/ml of erythromycin. The growth curve [log(OD$_{600}$) versus time] were almost similar for the clones in all of the six fermenters. At an OD$_{600}$ of 2.0, 40 ml of culture from each fermenter was concentrated 10 times and treated twice in a French press. The lysed solutions were subjected to the β-galactosidase activity measurement procedure as described by Miller, 1972, Experiments in Molecular Genetics, Cold Spring Harbor Laboratory, Cold Spring Harbor, N.Y. Unfortunately, a procedure for storing solutions without loosing β-galactosidase activity failed.

Therefore, only results from visual inspections of colour development in the β-galactosidase activity measurement were available:

| pH | H25A | p139–170 |
|-----|------|----------|
| 5.5 | +    | +        |
| 6.5 | +    | −        |
| 7.5 | +    | −        |

+: β-galactosidase activity present
−: β-galactosidase activity absent

Based on this experiment it was concluded that lacZ expression in P139-170 was a function of pH in the growth medium. However, it cannot be excluded that the content of arginine in the medium might also have a regulatory effect on the promoter function.

From selected integrant PFC-1 clones where regulated β-galactosidase expression was identified, DNA adjacent to the erm (or lacZ) proximal end was cloned using the following procedure:

Total DNA was extracted from a clone according to the method as defined in Example 2. About 1 µg DNA was digested with 50 units EcoRI and incubated for two hours at 37° C. Phenol and chloroform extraction and ligation in 200 µl of ligation buffer containing 50 units of ligase was carried out as described by Maniatis (reference 34). The DNA was precipitated by adding three volumes of ice cold ethanol and 1/10 volume sodium acetate, followed by centrifugation at 10.000×g for 30 minutes. The DNA was resuspended in 20 µl of TE (1 mM EDTA, 10 mM Tris hydrochloride [pH 8.0]). 10 µl ligated DNA solution was used for CaCl$_2$ transformation as described in reference 17, of *E. coli* DH5α (F-, endA1, hsdR17(r$_k$-,m$_k$+), supE44, thi-1, lacΔU169, recA1, gyrA96, relA1, Φ80 dlacZΔM15). About 1.5×10$^3$ transformants per µg DNA were obtained.

EXAMPLE 6

The construction of a promoter-probe vector for lactic acid bacteria

A useful tool for analysing the conditions that turn on a gene and measuring the level of expression, is a promoter probe. For Lactococcus, pGKV210, a promoter-probe vector based on chloramphenicol acetyl transferase and driven by the pWVO1 replicon has been constructed (van der Vossen et al., 1985). Unfortunately, this vector only provides slightly enhanced chloramphenicol-resistance when promoters are cloned into it (van der Vossen et al., 1987). Translation of mRNA containing the cat-86 gene is activated by chloramphenicol (Alexieva et al., 1988) so that the level of enzyme measured is dependent on two factors, the promoter strength and activation efficiency. In addition, the pWVO1 replicon replicates by rolling-circle replication, and is therefore susceptible to size-dependent segregational instability (Kiewiet et al. 1993).

A promoter-probe vector for Lactococcus and assumingly other lactic acid bacteria was constructed based on the βgalactosidase genes of *Leuconostoc mesenteroides* subsp. *cremoris*, the *Lactococcus lactis* subsp. *lactis* biovar diacetylactis citrate plasmid replicon and an erythromycin-resistance marker. This vector is named pAK80. Cloning of the promoter for the tRNA cluster adjacent to the tma gene of CHCC285 showed that this vector functions. The resulting construction, pAK90, produces extremely high levels of β-galactosidase in MG1363.

The β-galactosidase genes from *Leuconostoc mesenteroides* subsp. *cremoris* was cloned and found to be nearly identical to the β-galactosidase gene from *Leuconostoc lactis* (David et al., 1992). Both genes have been shown to be expressed in *Escherichia coli* and in *Lactococcus lactis* strain MG1363. The promoter of the β-galactosidase gene was deleted by polymerase chain reaction (PCR) and replaced with a polylinker, allowing cloning of various DNA fragments and testing for promoter activity. This construction was cloned into a shuttle vector containing the *L. lactis* subsp. *lactis* biovar diacetylactis citrate plasmid replicon, the pACYC184 replicon for *E. coli* and a selectable marker (erythromycin-resistance) for both organisms. Cloning of a tRNA promoter into the polylinker gave high levels of β-galactosidase in MG1363, proving that the vector works as planned.

A. Materials and methods

1. Bacterial strains, plasmids and media

MG1363 which is a plasmid-free *Lactococcus lactis* strain (Gasson, 1983). *Escherichia coli* DH5α [supE44 lacΔU169 hsdR17 recA1 endA1 gyrA96 thi-1 relA1 Φ801acZΔM15] (Hanahan, 1983) was used for cloning.

The cloning vectors and relevant markers which were used were: pVA891 [erythromycin resistance; Em$^R$] (Macrina et al., 1983), and pIC19H [ampicillin resistance; Amp$^R$] (Marsh et al., 1983). The various plasmids constructed during the construction of the promoter-probe vector are described in the following.

Lactococcus strains were grown at 30° C. in GM17 medium. *E. coli* strains were grown in LB medium at 37° C. Antibiotics were used at the following concentrations: for *E. coli*; erythromycin, 250 μg/ml; and ampicillin 50 μg/ml; for Lactococcus; erythromycin, 1 μg/ml.

2. Plasmid preparations and transformations

Plasmid DNA for sequencing and electroporations was prepared with the Qiagen plasmid kit (Diagen, Dusseldorf, Germany).

Small scale plasmid preparations from Lactococcus were done essentially according to Israelsen et al. 1993.

Plasmids were introduced into MG1363 by electroporation of glycine-grown competent cells essentially according to Holo and Nes, 1989.

3. β-galactosidase assays

Promoter activity was determined by carrying out β-galactosidase assays on overnight cultures grown in G1.5M17 medium. 1 ml of culture was centrifuged at 10,000×g for 10 min. The pellet was resuspended in 500 μl Z buffer (Miller, 1972). 100 μl of cell suspension was mixed with 400 μl of Z buffer, 12.5 μl 0.1% SDS and 25 μl CHCl$_3$ on a Vortex mixer for 10 seconds.

After Vortex mixing the suspension was treated as described in Example 7. The results are shown in Table 7.

The assay results are stated as Miller units. One Miller unit==$(1000 \times A_{420})/(time \times volume \times A_{600})$ (where time is in minutes and volume is in ml).

B. Construction of pAK66

Two PCR primers were obtained which allowed amplification of the entire replication region of the citrate plasmid. These had the following sequences:

Primer 1 (SEQ ID NO:1) 5'TGAATTCAGAGGTTTGAT-GACTTTGACC 3'

Primer 4 (SEQ ID NO:2) 5'GGAATTCCTAACAAAA-GACTATTAACGC 3'

Primer 1 corresponds to nucleotides 610–621 and Primer 4 is complementary to nucleotides 2340–2361 of the citrate plasmid replication region (Jahns et al., 1991). Both contain EcoRI sites at their 5' end to facilitate cloning. The 1.7 kb amplification product was cloned as an EcoRI fragment into pIC19H to produce pKR41. This EcoRI fragment was then moved into the unique EcoRI site of pVA891 to produce the shuttle vector pAK66 which replicates in *E. coli* and *L. lactis* MG1363. The construction of pKR41 has been described in a manuscript submitted for publication (Pedersen et al., 1993).

C. Cloning of the *Leuconostoc mesenteroides* subsp. *cremoris* β-galactosidase gene During the course of cloning and sequencing IS1165 from *Leuconostoc mesenteroides* subsp. *cremoris* strain DB1165 we obtained a clone called pSB1 (Johansen and Kibenich, 1992). This clone contained a 5.8 kb insert in the polylinker of pIC19H. Normally, cloning in pIC19H destroys β-galactosacase activity and colonies with inserts are white on X-gal. PSB1 was strange in that it gave blue colonies on X-gal. DNA sequence analysis revealed that the insert in pSB1 contained the β-galactosidase gene of *Leuconostoc mesenteroides* subsp. *cremoris* and that it was nearly identical to that of *Leuconostoc lactis* (David et al., 1992). Only 3 differences were detected in 830 bp sequenced.

D. Construction of pAK67.7

Figure 8:
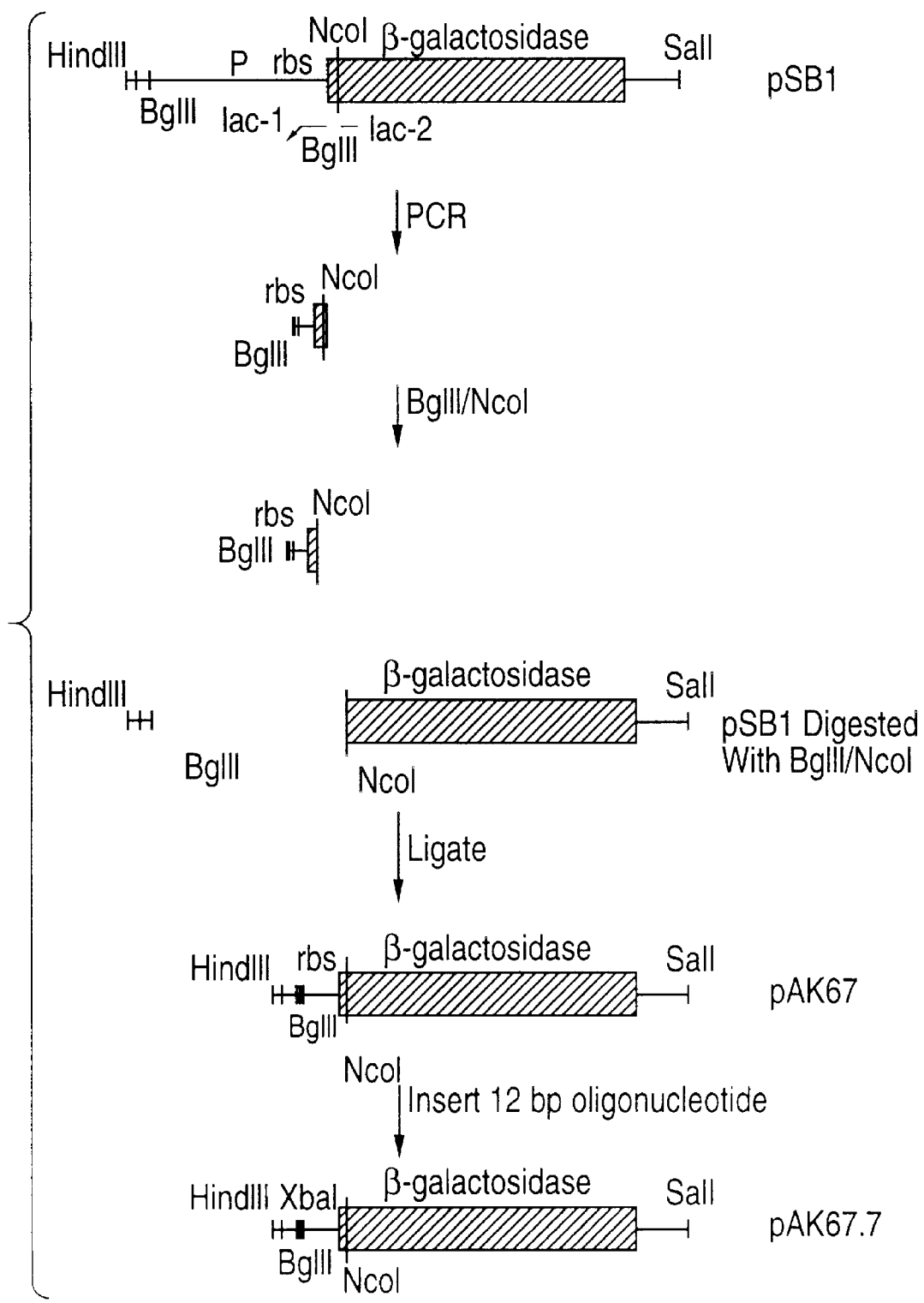
FIG. 8 illustrates the construction of pAK67.7 as described in Example 6. P represents the β-galactosidase promoter of Leuconostoc mesenteroides subsp. cremoris, and rbs the ribosome binding site. The sites of homology to the primers lac-1 and lac-2 are indicated by small arrows. The ribosome binding site is also present in pAK67.7.

This construction involved the replacement of the β-galactosidase promoter with a polylinker and insertion of stop codons in all 3 forward reading frames and is illustrated in FIG. 8. The promoter was removed by PCR using two primers:

lac-1 (SEQ ID NO:3) ATAGATCTGCAGGATCCCGG GTAACTTTGAAAGGATATTCCTC lac-2 (SEQ ID NO:4) ATTGAGGGTATACGGTGGGCG The underlined part of lac-1 is identical to the beginning of the β-galactosidase gene and contains the ribosome binding site. The remaining sequence contains a variety of restriction sites including BglII. The lac-2 primer anneals to the β-galactosidase gene, 20 bp downstream of the unique NcoI site. PCR amplification with these primers will amplify from the ribosome binding site to just beyond the NcoI site and produce a 360 bp fragment containing several restriction sites at one end, an NcoI site at the other end and no promoter or other regulatory sequences from the β-galactosidase gene. This 360 bp fragment was purified, digested with BglII and NcoI and cloned into BglII/NcoI digested pSB1. The resulting plasmid was named pAK67 and had the following polylinker preceding the β-galactosidase gene (SEQ ID NO:5):

```
               H
               i
               n              B        B
               d       X      g        Pa       S
               I       h      l        s m      m
               I       o      I        t H      a
               I       I      I        I I      I
               AAGCTTTCGCGAGCTCGAGATCTGCAGGATCCCGGGTAACTTTGAAAGGATATTCCTCATG
a (SEQ ID NO: 34) K  L  S  R  A  R  D  L  Q  D  P  G  *
b (SEQ ID NO: 35)    S  F  R  E  L  E  I  C  R  I  P  G  N  F  E  R  I  F  L  M  —
c (SEQ ID NO: 36)       A  F  A  S  S  R  S  A  G  S  R  V  T  L  K  G  Y  S  S     —
```

DNA sequence analysis revealed that this polylinker was present and that no alterations had been introduced in the β-galactosidase gene by errors during PCR.

As can be seen above, there are two open reading frames that go across the polylinker into the β-galactosidase gene. Since these could potentially interfere with expression of βgalactosidase from promoters inserted into the polylinker, it was decided to introduce stop codons in all three forward reading frames. This was done by obtaining two oligonucleotides with the following sequence:

Stop-1 (SEQ ID NO:6) GGGTCTAGATTA
Stop-2 (SEQ ID NO:7) TAATCTAGACCC

These oligonucleotides are complementary and will anneal to give a 12 bp piece of double stranded DNA containing an XbaI restriction site. This small fragment was cloned into the SmaI site of pAK67. These oligonucleotides were designed in such a way that the SmaI site would be retained, a new XbaI site would be present in plasmids with this tiny insert and stop codons would be introduced into the two open reading frames. The cloning was done by digesting pAK67 with SmaI, phosphatase treating and ligating with a mixture of the two oligonucleotides that had been treated with kinase and allowed to anneal to each other. Transformants were purified and those in which the plasmid had gained an XbaI site were further analyzed. DNA sequence analysis revealed that one clone, pAK67.7 had the desired structure (SEQ ID NO:8):

E. Construction of pAK80

The final step in the production of the promoter-probe vector was the combining of the manipulated β-galactosidase gene with a replicon and selectable marker for Lactococcus. This was accomplished by digesting pAK67.7 with HindIII and SalI and ligating into pAK66, also digested with HindIII and SalI. Among the plasmids produced, was pAK80 which was the promoter-probe vector exactly as originally designed.

The plasmid pAK80 harboured by *Lactococcus lactis* ssp. *lactis* MG1363 was deposited with the DSM-Deutsche Sammlung von Mikroorganismen und Cellkulturen GmbH, Mascheroder Weg 1b, D-38124 Braunschweig, Germany on 27 Aug. 1993 under the accession number DSM 8496.

F. Testing of pAK80 using two regulatable tRNA promoters

Figure 11:
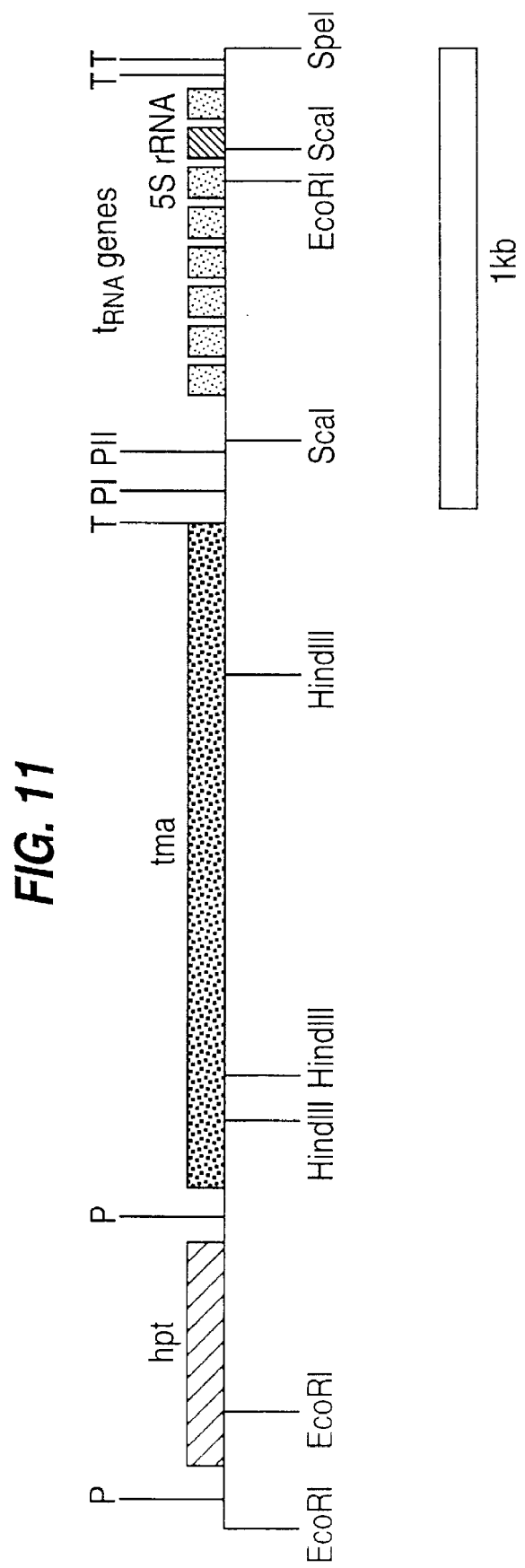
FIGS. 11 illustrates a DNA fragment from Lactococcus lactis subsp. lactis strain CHCC285 containing seven tRNA genes and a 5S rRNA gene arranged in a single operon including two promoters and two putative transcription terminators.

A DNA fragment from *Lactococcus lactis* subsp *lactis* adjacent to the tma gene of CHCC285 has been isolated and found to contain a cluster of tRNA genes preceded by a promoter region (FIGS. 11 and 12 and SEQ ID NOS:20 and 21 ) comprising two potential promoters (PI, nucleotides 107–134; PII, nucleotides 215–242). The PI and PII promoters, contained on a 501 bp HindIII-ScaI fragment isolated from the clone pLN39 was cloned by inserting it into pAK80 digested with HindIII and SmaI, in front of the promo- terless *Leuconostoc mesenteroides* subsp *cremoris* β-galactosidase gene. Following ligation, MG1363 was electroporated and the cells were plated on regeneration medium (Holo and Nes, 1989) containing erythromycin and X-gal. A total of seven blue colonies were obtained. Plasmid analysis revealed that all seven had identical plasmids and that each contained the desired insertion in pAK80. One plasmid was isolated and designated pAK90. β-galactosidase assays revealed that MG-1363/pAK90 produced 5000 Miller units of enzyme, while MG-1363/pAK80 produced 1 Miller units. Thus, the region preceding the tRNA genes contains a very strong promoter.

Searching for sequences with similarity to the sequence of the above promoter region (FIG. 13 and SEQ ID NOS:22–31) revealed a consensus sequence of promoters preceding rRNA operons and tRNA operons from Lactococcus species including a previously undescribed conserved sequence (motif), AGTT. This sequence ends 5 bp upstream of the –35 region and is not conserved in tRNA and rRNA promoters of *Escherichia coli* or *Bacillus subtilis*. In all Lactococcus species where this AGTT motif was found to precede potential rRNA or tRNA promoters, these promoters had all been isolated from plasmids where the promoters were inserted in front of the cat-86 gene coding for chloramphenicol acetyltransferase. Since this enzyme is expressed poorly in *Lactococcus lactis* resistance to

```
                H
                i
                n              B        B
                d       X      g        Pa       S        X
                I       h      l        s m      m        b
                I       o      I        t H      a        a
                I       I      I        I I      I        I
                AAGCTTTCGCGAGCTCGAGATCTGCAGGATCCCGGGTCTAGATTAGGGTAACTTTGAAAGGATATTCCTCATG
             1  ---------+---------+---------+---------+---------+---------+---------+---  73
                TTCGAAAGCGCTCGAGCTCTAGACGTCCTAGGGCCCAGATCTAATCCCATTGAAACTTTCCTATAAGGAGTAC
a (SEQ ID NO: 37) K  L  S  R  A  R  D  L  Q  D  P  G  S  R  L  G  *
b (SEQ ID NO: 38)    S  F  R  E  L  E  I  C  R  I  P  G  L  D  *              β-galactosidase M -->
c (SEQ ID NO: 39)       A  F  A  S  S  R  S  A  G  S  R  V  *
``` chloramphenicol can only be obtained in this organism by cloning strong promoters in front of the cat-86 gene. Therefore it appears that the motif AGTT is found only in strong promoters of *Lactococcus lactis*.

The above promoters PI and PII both contain conserved sequences assumingly involved in stringent control (FIG. 13) and accordingly, these promoters appear to be regulatable promoters.

A 1.0 kb HindIII-EcoRI fragment from pLN39 was inserted into the plasmid pCI3340 digested with HindIII and EcoRI and the resulting plasmid pLN40 was introduced into Lactococcus lactis MG1363. pLN40/MG1363 was deposited with the DSM-Deutsche Sammlung von Mikroorganismen und Cellkulturen GmbH, Mascheroder Weg 1b, D-38124 Braunschweig, Germany on 22 Dec. 1993 under the accession numbers DSM 8858.

G. Conclusions

This Example describes the construction of a novel promoter-probe vector for Lactococcus and assumingly other lactic acid bacteria. This vector has several advantages over previously described vectors. It is based on the *Lactococcus lactis* subsp. *lactis* biovar diacetylactis citrate plasmid replicon, a theta-replicating plasmid, and so is more stable. The reporter gene chosen is not subject to post-transcriptional control so the enzyme levels can be measured without the presence of any inducers. This is in contrast to plasmids based on the cat-86 gene where chloramphenicol actually activates the translation of the mRNA (Alexieva et al., 1988). Enzyme assays and plate assays for the reporter gene are simple and standard procedures in most laboratories.

EXAMPLE 7

Measurements of β-galactosidase expression in PFC-1 integrants grown in liquid medium under controlled conditions

*Lactoccus lactis* ssp. *lactis* MG1363 PFC-1 clones (LTV1 integrants) as defined in Example 4 are usually designated P139- followed by a number indication, e.g. P139-170. In the following, however, PFC-1 integrants are termed only by their number, e.g. 170. In this study was also included the LTV1 integrant in *Lactoccus lactis* ssp. *lactis* MG1614, mentioned in Example 5 under the designation H25A. However, in the following, this integrant has been designated as SB.

The following experiment was carried out with the aims of studying the pH dependence of lacZ expression of the two integrants 170 and SB.

Integrant 170 was shown to be of type 1A whilst integrant SB apparently did not belong to this group. Both integrants are of type 2S which means that the expression of β-galactosidase on GM17 plates is not affected by 2% NaCl.

Four fermenters each containing 1 liter of G1.5M17 medium, i.e. 1.5×M17 broth (Sigma Chemical Co.) containing 0.5% glucose and supplemented with 1 mg/l erythromycin were set to operate at 30° C. Stirring was kept at 150 rpm without active supply of air/$O_2$. The fermenters in duplicate were set to operate at pH 5.2 and 7.0, respectively using 5M hydrochloride and 5M sodium hydroxide. One of the fermenter duplicates was inoculated with 1% of an overnight culture of integrant SB and the other duplicate was inoculated with 1% of an overnight culture of integrant 170.

The fermentations were run for 45 hrs and the growth was followed by measuring $OD_{600}$. At selected $OD_{600}$ values and time intervals β-galactosidase activity was measured as follows: 10 ml aliquots from each fermenter were centrifuged at 10,000× g at 4° C. for 5 minutes. The pellet was resuspended in 1 ml Z buffer (Miller, 1972) and 0.4 ml of the bacterial suspension and 0.1 ml Z buffer was mixed with 12.5 μl 0.1% SDS and 25 μl $CHCl_3$ by means of a Vortex mixer for 10 seconds. The vortexed suspension was placed in a 30° C. water bath for 5 minutes and 100 μl of a solution containing 4 mg/ml of o-nitrophenyl-β-D-galactopyranoside (ONPG) in A-medium (Miller, 1972) was added. The suspension was vortexed for 2 seconds and placed in a 30° C. water bath.

The time was noted at ONPG addition and again when the enzymatic reaction was stopped by the addition of 250 μl 1M $Na_2CO_3$ followed by Vortex mixing and placing of the suspension on ice. After centrifugation at 10,000×g at 4° C. for ten minutes $OD_{420}$ and $OD_{550}$ of the supernatant were measured. If $OD_{550}$ values exceeded 0.050 the suspension was centrifuged again and $OD_{420}$ and $OD_{550}$ of this supernatant were measured. The β-galactosidase activity was estimated by using the following formula:

$$\beta\text{-galactosidase activity} = \frac{522 \times OD_{420}}{\text{time (min)} \times \text{cell vol (ml)} \times OD_{600}}$$

Figure 9:
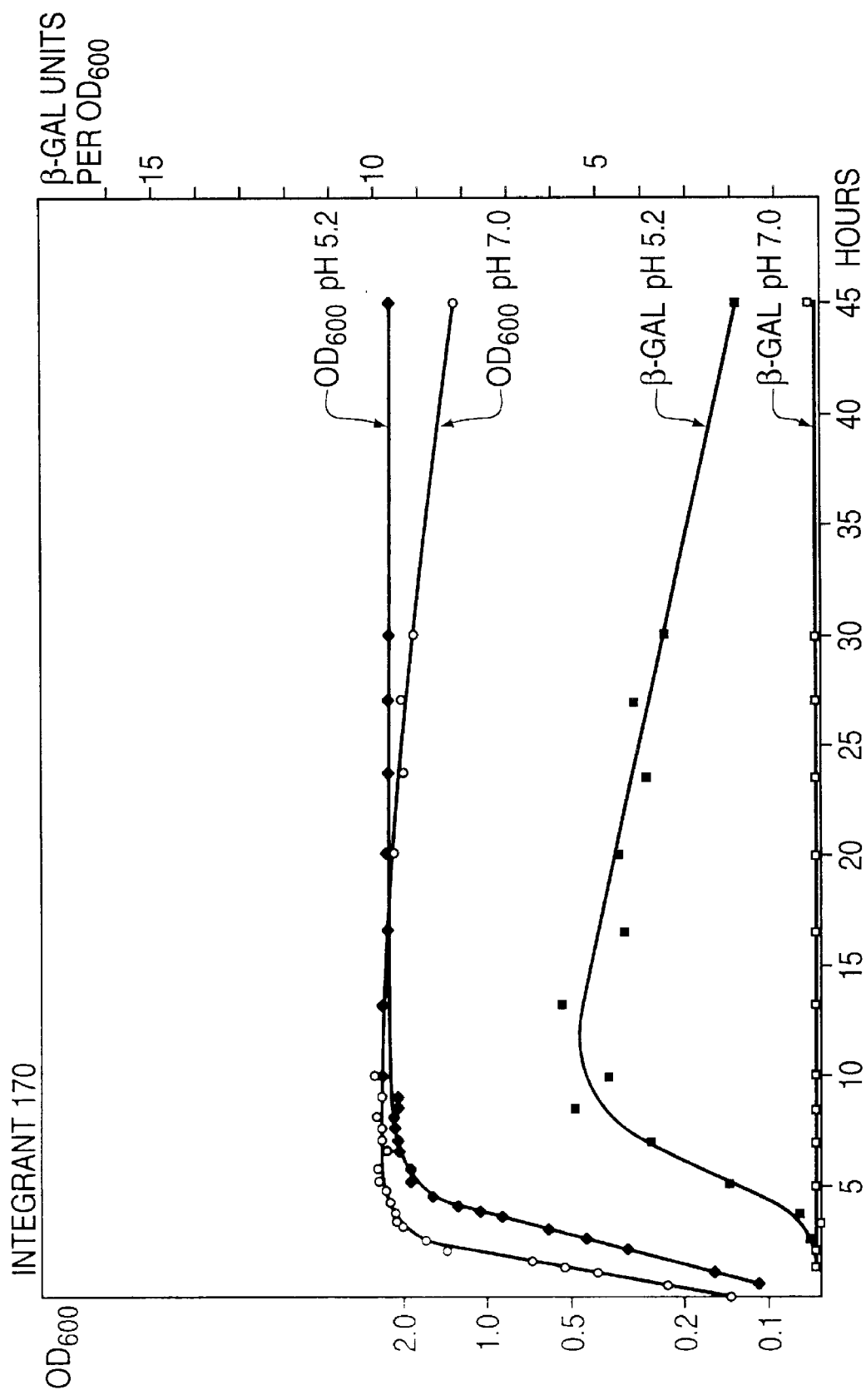
FIG. 9 illustrates the growth and β-galactosidase activity of the LTV1 integrant 170 grown at pH 5.5 and 7.0.
Figure 10:
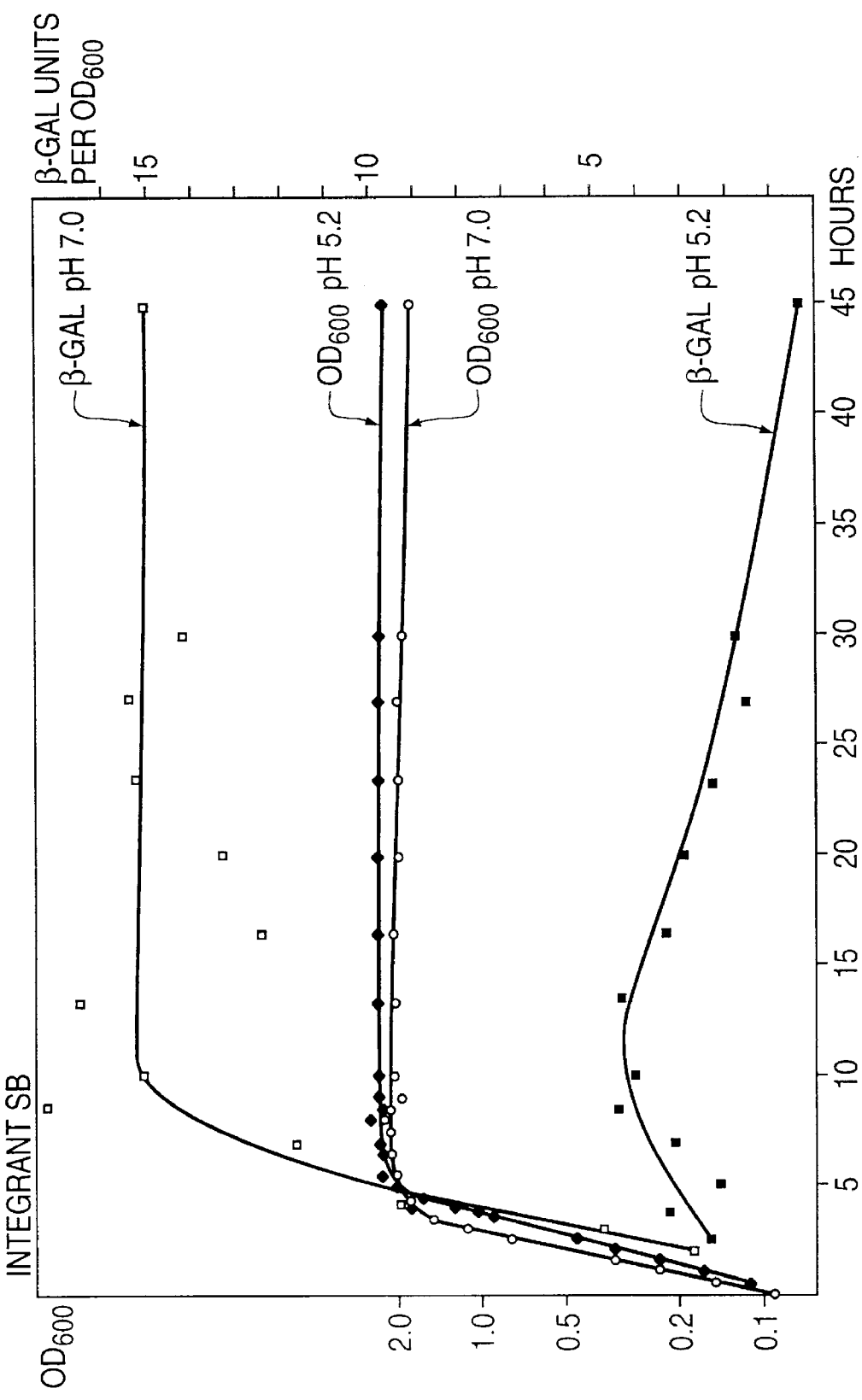
FIG. 10 illustrates the growth and β-galactosidase activity of the LTV1 integrant SB grown at pH 5.5 and 7.0.

In FIG. 9 the $OD_{600}$ and β-galactosidase activity versus time are shown for integrant 170 at pH 5.2 and pH 7.0. In FIG. 10 the corresponding data are shown for integrant SB. It is clearly demonstrated by the data in these two figures that the expression of β-galactosidase of integrants 170 and SB are oppositely regulated by pH. Integrant 170 turns off the β-galactosidase expression at pH 7.0. In both integrants, β-galactosidase expression is also influenced by the growth phase. This experiment does not exclude that the concentration of arginine in the medium may also have a regulatory effect on the β-galactosidase expression in the two integrants studied.

EXAMPLE 8

Cloning of DNA fragments containing a lactic acid bacterial promoter and assessment of promoter activity in *Lactococcus lactis*

A. Cloning in *E. coli* of EcoRI fragments containing *Lactococcus lactis* DNA and the ColE1 replicon from Tn917-LTV1 integrants Chromosomal EcoRI fragments containing lactococcal DNA, lacZ, cat, bla and the ColE1 replicon, were prepared according to the method described in Example 5 from the Tn917-LTV1 integrants listed in Table 5 below. The fragments were subsequently religated and introduced into *E. coli* DH5α by transformation as described in Maniatis 1982.

The resulting Tn917-LTV1 integrant fragment plasmids were termed p[integrant No], e.g. p86, p143 and pSB. All Tn917LTV1 integrants from which the fragments were isolated are in *Lactococcus lactis* MG1363 except SB which is Tn917-LTV1 in *Lactococcus lactis* MG1614.

TABLE 5

Regulation parameters for β-galactosidase expression in selected integrants. The parameters are deduced from plate assays.

| Integrant No. | Parameter |
|---|---|
| 86 | arg./pH |
| 143 | temp./growth rate |
| 159 | temp./growth rate |
| 162 | arg./pH |
| 163 | arg./pH ; $pO_2$ |
| 170 | temp./growth rate; arg./pH |
| 172 | temp./growth rate |
| 179 | arg./pH; NaCl/ion strength |
| 187 | temp./growth rate |
| 188 | temp./growth rate |

TABLE 5-continued

Regulation parameters for β-galactosidase expression in selected integrants. The parameters are deduced from plate assays.

| Integrant No. | Parameter |
|---|---|
| 189 | NaCl/ion strength |
| 192 | temp./growth rate; arg./pH |
| 199 | NaCl/ion strength; arg./pH |
| 201 | temp./growth rate |
| 202 | temp./growth rate |
| 222 | arg./pH |
| 224 | arg./pH |
| 241 | NaCl/ion strength |
| 242 | arg./pH |
| SB | temp./growth rate; arg./pH |

B. Subcloning of Tn917-LTV1 integrant fragment plasmids into the promoter selection vector DGKV210 pGKV210 is a promoter selection vector which contains an erm gene as a selection marker and a promoterless cat-86 gene preceded by a polylinker (van der Vossen et al, 1987). The cat-86 gene is expressed if a DNA fragment carrying a promoter is inserted in the right orientation into the polylinker. The level of chloramphenicol resistance conferred to the host depends on the strength of the promoter.

The integrant fragment plasmids all have a ClaI site located in the DNA originating from the lacZ part of Tn917-LTV1. In order to clone the EcoRI-ClaI fragments from the plasmids, a ClaI site was first introduced into the polylinker of pGKV210 in the following manner: The synthetic DNA linker (SEQ ID NO:9 and 10)

5'GATCGCCATCGATGGC 3'
3' CGGTAGCTACCGCTAG 5' containing a ClaI site was cloned into the unique BamHI site of pGKV210 as described by Maniatis, 1982. The obtained plasmid was termed pGKV210(ClaI). 50 ng of pGKV210 (ClaI) digested with ClaI and EcoRI was mixed and ligated with 200 ng of purified ClaI-EcoRI fragment as defined above. This was done with ClaI-EcoRI fragments from the following integrant fragment plasmids: p143, p162, p163, p170, p172, p224, p237, p242 and pSB.

p162 contains an additional ClaI site located in the lactococcal DNA. The fragment from the EcoRI site of this plasmid to the additional ClaI site was inserted into pGKV210(ClaI) All of the DNA recombination work in this Example was carried out according to Maniatis, 1982.

The resulting pGKV210 derivative constructs were termed pGKV210:[integrant No], e.g. pGKV210:143, pGKV210:162 and pGKV210:SB. The pGKV210 derivatives were introduced into *E. coli* MC1000 (F-, araD139 (Δara-leu)7679, galU, galK(Δlac)X74, npsL(Strr), thi) according to the method as described in Example 5. The pGKV210 derivatives were extracted as described in Maniatis, 1982 from the transformed host strain. For each extracted pGKV derivative, 1 µg of DNA was introduced into *Lactococcus lactis* MG1363 according to the method as described in Example 1. The resulting transformants (pGKV/MG1363 derivatives) were designated pGKV210:[integrant No]/MG1363, e.g. pGKV210:143/MG1363.

The promoter activity of the above cloned fragments and of previously published pGKV210 derivatives in *Lactococcus lactis* IL1403 (van der Vossen et al., 1987) were determined by plating overnight culture of the pGKV/MG1363 derivatives onto GM17 plates supplemented with 5 mg/l erythromycin and increasing concentrations of chloramphenicol. The concentrations of chloramphenicol were 4, 6, 8, 12, 16, and 20 mg/l, respectively. 50 µl of a $10^4$ times diluted culture in a 0.9% NaCl aqueous suspension were plated on plates with 4–8 mg/l of chloramphenicol. 100 µl of a $10^4$ times diluted culture in 0.9% NaCl were plated on plates containing 12–20 mg/l of chloramphenicol. The plates were incubated at 30° C. for about 80 hrs and the maximum concentration of chloramphenicol still allowing growth was determined. Results are shown in Table 6 below.

Only two pGKV/MG1363 derivatives were resistant to more than 4 mg/l chloramphenicol. However, difficulties in the interpretation of the results were encountered e.g. due to the appearance of small colonies and this assay seems to be inadequate for promoters of medium or weak strength. The pGKV244/IL1403 and pGKV259/IL1403 produce 0,2 and 5.1 units, respectively, when assayed for chloramphenicol acetyltransferase activity (van der Vossen et al, 1987).

TABLE 6

Maximum chloramphenicol (Cm) levels allowing growth of strain MG1363 harbouring pGKV210 and pGKV210 derivatives.

| Plasmid harboured by MG1363 | Concentration of Cm (g/ml) |
|---|---|
| pGKV210 | <4 |
| pGKV244 | 8 |
| pGKV259 | 16 |
| pGKV210:143 | 4 |
| pGKV210:162 | 4 |
| pGKV210:163 | <4 |
| pGKV210:170 | <4 |
| pGKV210:172 | 8 |
| pGKV210:224 | <4 |
| pGKV210:237 | 4 |
| pGKV210:242 | <4 |
| pGKV210:SB | 12 |

C. Subcloning of Tn917-LTV1 integrant fragment plasmids into the promoter selection vector pAK80 pAK80 is a promoter selection vector which contains an erm gene as a selection marker and a promoterless β-galactosidase gene preceded by a polylinker. The construction of pAK80 is described in Example 6.

The following DNA operations and transformations were carried out according to Maniatis, 1982. The integrant fragment plasmids as described above were first subcloned into the cloning vector pGEM-7Zf(+) (Promega) due to the lack of appropriate restriction sites in pAK80. 50 ng of pGEM-7Zf(+) digested with ClaI and EcoRI was mixed under ligation conditions with 200 ng of purified ClaI-EcoRI fragments containing lactococcal DNA from an integrant fragment plasmid. This was done with ClaI-EcoRI fragments from the following plasmids: p143, p162, p163, p224, p242 and pSB, respectively.

p170 contains a SalI site located in the lactococcal DNA. The fragment from the ClaI site to this SalI site was inserted into the cloning vector pBluescript II KS (Strategene) which was digested with ClaI and SalI. This construct was termed pBluescript:170. Extracted plasmid DNA from this construction was digested with XhoI and ClaI and ligated to pGEM-7Zf(+) digested with XhoI and ClaI. The pGEM-7Zf (+) constructions were termed pGEM:[integrant No], e.g. pGEM:143 and pGEM:170 and collectively designated pGEM derivatives. The pGEM derivatives were introduced into *E. coli* strain DH5α as described in Example 5. The DH5α transformants were termed pGEM/DH5α derivatives.

Plasmid DNA from the pGEM/DH5α derivatives were extracted, digested with XhoI and BamHI and ligated to pAK80 digested with XhoI and BamHI. The resulting constructions were termed pAK80:[integrant No], e.g.

pAK80:143 and pAK80:170 and collectively designated pAK80 derivatives. The pAK80 derivatives were introduced into *E. coli* MC1000 as described in Example 5.

The MC1000 transformants were designated pAK80/MC1000 derivatives. The pAK80 derivatives were extracted from the pAK80/MC1000 derivatives. For each extracted pAK80 derivative 1 µg DNA was introduced into *Lactococcus lactis* MG1363 as described in Example 5. The resulting transformants were termed pAK80:[integrant No]/MG1363, e.g. pAK80:143/MG1363 and pAK80:170/MG1363 and collectively designated pAK80/MG1363 derivatives.

The promoter activity of the cloned fragments were determined by carrying out β-galactosidase assays on overnight cultures of the pAK80/MG1363 derivatives grown in G1.5M17 medium. 1 ml of culture was centrifuged at 10,000×g for 10 min. The pellet was resuspended in 500 µl Z buffer (Miller, 1972). 100 µl of cell suspension was mixed with 400 µl of Z buffer, 12.5 µl 0.1% SDS and 25 µl CHCl₃ on a Vortex mixer for 10 seconds. After Vortex mixing the suspension was treated as described in Example 7. The results are shown in Table 7.

TABLE 7

β-galactosidase activity of strain MG1363 harbouring pAK80 and pAK80 derivatives.

| Plasmid harboured by MG1363 | β-galactosidase activity (Miller units) |
|---|---|
| pAK80 | 1 |
| pAK80:SB | 820 |
| pAK80:143 | 240 |
| pAK80:162 | 80 |
| pAK80:163 | 1 |
| pAK80:170 | 30 |
| pAK80:224 | 1 |
| pAK80:242 | 1 |

It is clearly demonstrated from the above results that the promoter selection vector pAK80 is capable of discriminating even weak promoters, since pAK80:163/MG1363, pAK80:170/MG1363, pAK80:224/MG1363 and pAK80:242/MG1363 appear to be without promoter activity when assayed for chloramphenicol resistance, but when assayed for β-galactosidase activity it is evident that pAK80:170/MG1363 in contrast to the three other pAK80/MG1363 derivatives, has promoter activity.

The following pAK80/MG1363 derivatives: pAK80:SB/MG1363, pAK80:143/MG1363, pAK80:162/MG1363, pAK80:163/MG1363, pAK80:170/MG1363, respectively were deposited with the DSM-Deutsche Sammlung von Mikroorganismen und Cellkulturen GmbH, Mascheroder Weg 1b, D-38124 Braunschweig, Germany on 27 Aug. 1993 under the accession numbers DSM 8495, DSM 8497, DSM 8498, DSM 8499 and DSM 8500, respectively.

The ClaI-EcoRI fragments from p172 and p215, respectively, containing the lactococcal DNA, were cloned into pGEM-7Zf(+). The pGEM-7Zf(+) constructions were termed as described above in this Example.

The pGEM-7Zf(+) constructions were digested with BamHI and XhoI and ligated to pAK80, also digested with BamHI and XhoI. The details of the cloning experiments were as described above. pGEM:172 was digested with XbaI and BamHI. The ligation mixture was introduced into *E. coli* DH5α, and the resulting plasmid, pAK80:172, was introduced into *Lactococcus lactis* MG1363. pAK80:172/MG1363 is blue on GM17 containing X-gal which demonstrates the presence of a promoter on the 4.5 kb ClaI-EcoRI fragment of p172.

The lactococcal DNA segment of pGEM:215 contains an internal BamHI site. The distal BamHI-XhoI fragment of pGEM:215 was ligated to pAK80 digested with BamHI and XhoI and the lactococcal BamHI-BamHI fragment was ligated to pAK80 digested with BamHI. Each ligation mixture was introduced into *E. coli* DH5α. The resulting plasmids were designated pAK80:215A and pAK80:215B, respectively. The correct orientation of the BamHI fragment in pAK80:215B was verified by restriction map analysis. A subsequent introduction of pAK80:215A and pAK80:215B, respectively, into *Lactococcus lactis* revealed that none of the plasmids harboured a promoter. This result suggests that a potential promoter on ClaI-EcoRI fragments from p215 had been inactivated during cloning of the two subfragments or that the promoter responsible for β-galactosidase expression in Integrant 215 is located upstream of the EcoRI site.

Measurements on overnight cultures of *Lactococcus lactis* MG1363 containing the plasmids pAK80:SB, pAK80:143, pAKBO:162, pAK80:170 and pAK80:172, respectively, are described in Example 13 below. However, in Example 13 these plasmids are designated pSMA332, pSMA337, pSMA338, pSMA339 and pSMA345, respectively.

EXAMPLE 9

Characterization of a *Lactococcus lactis* promoter regulated by external purine compounds The de novo synthesis of purine nucleotides from small precursors requires in general 10 enzymatic reactions leading to inosine monophosphate (IMP). IMP is used in synthesis of both AMP and GMP. Purine bases and nucleosides, originating intracellularly or from exogenous sources, are converted to nucleotides via salvage pathways, which have been shown to be distinct among different organisms (for review see: Nygaard 1983). Virtually nothing is known about the purine metabolism in the anaerobic Gram-positive bacterium *Lactococcus lactis* other than described (Nilsson and Lauridsen, 1992).

The media used for growth of lactic acid bacteria may contain urine compounds. Such media repress the synthesis of enzymes used in the formation of purine nucleotides. When the dairies inoculate the cultures in the purine-free milk, this repression is relieved. This regulation pattern of the synthesis of enzymes used in the purine de novo pathway can be used commercially. There may be several genes encoding enzymes that is desirable to have expressed highly in milk, but is unwanted during the manufacturing of dairy starter cultures comprising such genes primarily because of growth inhibiting secondary effects caused by the high expression. Therefore, a purine regulated promoter was searched for in *Lactococcus lactis* and the promoter region, from which the expression of purD is initiated was isolated. The purD gene encodes an enzyme of the purine de novo pathway.

Bacterial strains and growth media

The *Lactococcus lactis* strain MG1363 was grown in M17 medium (Oxoid) or in defined medium, DN-medium. This medium is composed as follows (per liter): 100 ml of a 10% salt buffer with the following composition: $(NH_4)_2SO_4$ 10 g, $Na_2HPO_4$, $2H_2O$ 33.2 g, $KH_2PO_4$ 15 g, NaCl 5 g, NaAcetate,$3H_2O$ 10 g, ion exchanged water ad 500 ml; 900 ml of basis medium containing 1.0M $MgCl_2$ 10 ml, 0.5M $CaCl_2$ 1.0 ml, 0.01M $FeCl_3$ 1.5 ml, ion exchanged water ad 4500 ml, 15 g of agar per liter; 25 ml of 20% carbon source; 25 ml of casamino acids, 20% (Difco); 10 ml of vitamin solution and 10 ml of a 0.8% aspargine solution.

Glucose was used as carbon source in M17 medium and DN medium. Antibiotics used for *Lactococcus lactis* :

Erythromycin, 1 mg/l. Purine compounds as supplements were added, when necessary, per 1: Adenine and hypoxanthine, 15 mg; -guanosine, 30 mg).

DNA manipulation

Lactococcus lactis plasmid DNA was isolated according to Johansen and Kibenich (1992). Lactococcus lactis was transformed by electroporation as recommended by Holo and Nes (1989). The use of the Lactococcus lactis promoter-probe plasmid pAK80 is described in Example 6.

Results

A 846 bp DNA fragment (FIG. 14) contains the entire purD promoter region as well as an adjacent promoter initiating transcription in the opposite direction. This region was fused to the reporter gene (encoding β-galactosidase) in the promoter probe plasmid pAK80 giving pLN71 (purD promoter expression) and pLN72 (promoter expression opposite direction). Transforming pLN71 into Lactococcus lactis strain MG1363 gives us the possibility to measure the expression of the reporter gene initiated from the purD promoter. The results are shown in Table 8.

The plasmid pLN71 in Lactococcus lactis strain MG1363 was deposited on 22 Dec. 1993 with the DSM-Deutsche Sammlung von Mikroorganismen und Cellkulturen GmbH, Mascheroder Weg 1b, D-38124 Braunschweig, Germany under the accession number DSM 8859.

TABLE 8

Expression of β-galactosidase in pLN71

| Strain | act.[a] in DN-medium | act.[b] in DN-medium + A,Hx,GR[c] |
|---|---|---|
| MG1363/pLN71 | 310 | 5 |
| MG1363/pLN72 | 23 | 6 |
| MG1363/pAK80 | <2 | <2 |

[a]Cells were grown exponentially at 30° C. in DN-medium containing purines, harvested, washed, and resuspended in purine-free DN-medium, and incubated further 1.5 hour. The β-galactosidase activity expressed from the respective promoter was measured.
[b]Cells were grown exponentially in defined medium containing purines. The β-galactosidase activity expressed from the respective promoter was measured.
[c]A, adenine; Hx, hypoxanthine; GR, guanosine These results show that the expression of the reporter gene encoding the β-galactosidase is regulated by purine compounds in the media, and that the difference is as large as 60 fold in this experiment.

EXAMPLE 10

Measurement of β-galactosidase gene expression in pSMA344/MG-1363 grown in liquid medium under controlled conditions The plasmid pSMA344 consists of the 9.7 kb EcoRI-ClaI fragment from p170 (see Example 8) inserted into the promoter cloning vector pAK80. In Integrant 170, expression of the inserted β-galactosidase gene has been demonstrated to be regulated by pH and growth phase (Example 7). The following experiment was performed to investigate if the cloned DNA fragment contains the sequences that are necessary for pH regulated expression of downstream genes.

Figure 15:
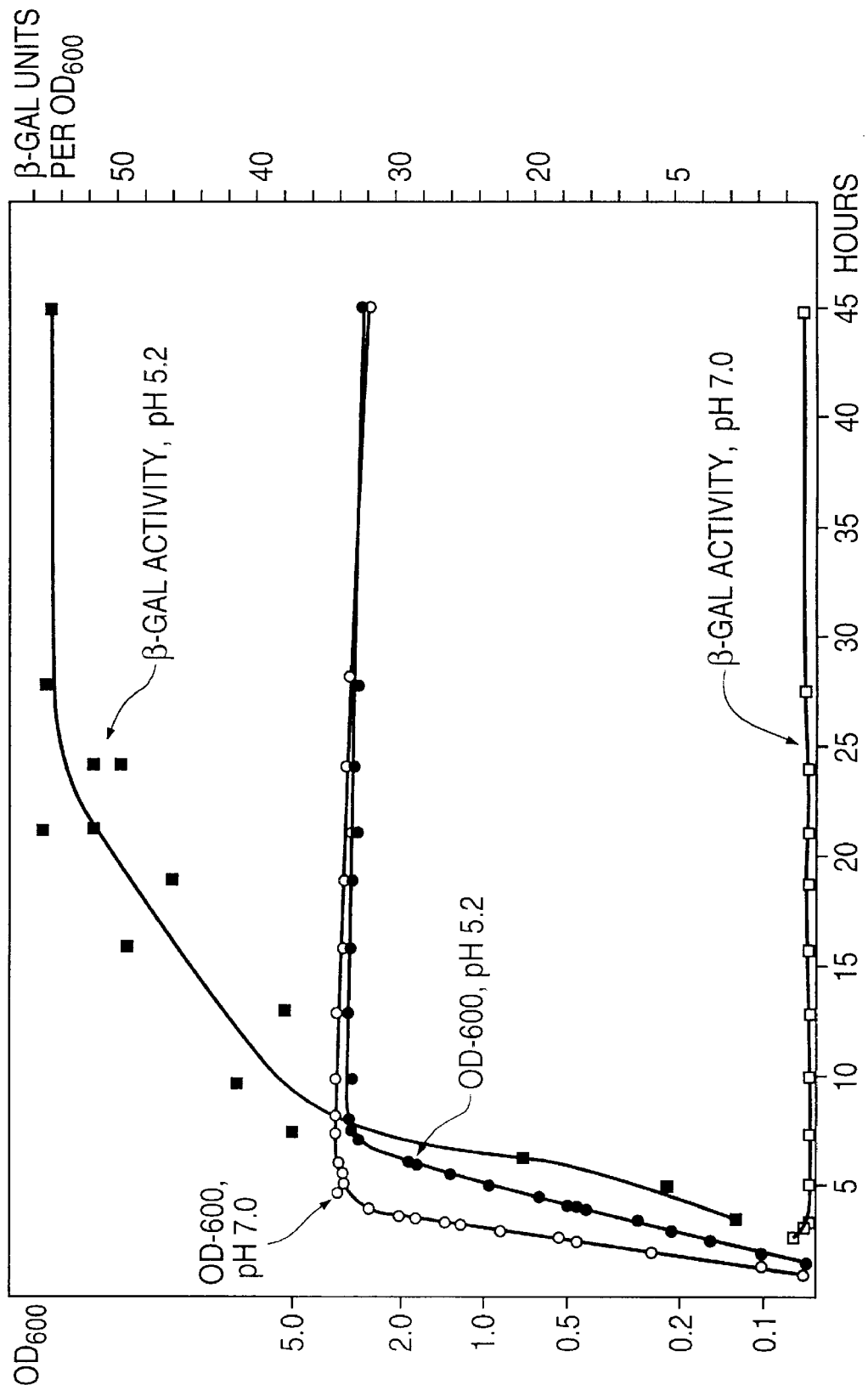
FIG. 15 illustrates the OD$_{600}$ and the β-galactosidase activity versus time during fermenter growth of pSMA344/MG-1363 in liquid medium under controlled conditions.

Lactococcus lactis MG1363 harbouring the plasmid pSMA344 was cultivated in two fermenters each containing 1 liter of medium. The fermenters were set to operate at pH 7.0 and 5.2, respectively, by automatic addition of 5M sodium hydroxide and 5M hydrochloric acid. Any other parameter (medium composition, inoculum size, stirring rate, temperature etc.) was as described in Example 7. The fermentations were run for 45 hours and the growth was followed by measuring $OD_{600}$ in culture samples. Sampling and harvesting of culture aliquots as well as measurement of β-galactosidase activity were performed as described in Example 5, except that the culture volume harvested and the cell suspension volume added to the assay were varied according to cell density and expected β-galactosidase activity. FIG. 15 shows the $OD_{600}$ and the β-galactosidase activity versus time during the fermentation. It is clear from the results that expression from the promoter harboured on pSMA344 is controlled in the same manner as that observed in Integrant 170. In the culture grown at pH 7.0 the β-galactosidase activity per $OD_{600}$ was less than 1.0 Miller unit throughout the fermentation except in the first sample where some activity will be expected to remain from the preculture. In the culture grown at pH 5.2, β-galactosidase activity per $OD_{600}$ increased during logarithmic growth and continued to increase during the first 14–20 hours of the stationary phase. Both the induced and the repressed levels were 5 to 10 times higher than the values obtained in Integrant 170 under the same culture conditions. This was expected, as the gene carried by the plasmid is present in a higher copy number, and as the two β-galactosidase enzymes encoded by the lacZ gene (in Tn917-LTV1) and by the lacL-lacM genes (in pAK80) may have different specific activities.

EXAMPLE 11

Measurements of β-galactosidase activity in selected PFC-1 integrants grown in liquid medium by a standardized procedure As described in Example 5, a number of integrants were found to show regulated expression of β-galactosidase when grown on plates under varying growth conditions and medium compositions.

The experiments described below were performed to analyze the regulation of β-galactosidase gene expression in 25 selected integrants grown overnight in liquid culture. The regulation parameters analyzed included pH and/or arginine concentration, sodium chloride concentration, and growth temperature.

Growth media and methods

The media used for liquid cultures are listed in the table below. The basic medium for all experiments was 1.5×M17 broth (Oxoid, Unipath Ltd., UK) containing 1 mg/l erythromycin.

TABLE 9

Media used for liquid cultures of integrants

| Medium | Composition | Final culture pH |
|---|---|---|
| G1.5M17 | 1.5 × M17 broth containing 0.5% glucose and 1 mg/l erythromycin | 5.5–5.8 |
| ArgG1.5M17 | 1.5 × M17 broth containing 0.1% glucose, 0.1% L-Arginine, and 1 mg/l erythromycin | 6.6–6.8 |
| 5ArgG1.5M17 | 1.5 × M17 broth containing 0.1% glucose, 0.5% L-Arginine, and 1 mg/l erythromycin | 7.7–7.8 |
| G1.5M17-NaCl | G1.5M17 containing 1% NaCl | 5.5–5.6 |
| G1.5M17-2NaCl | G1.5M17 containing 2% NaCl | 5.4–5.5 |

All cultures were incubated at 30° C. except in the experiment for investigation of temperature effect on β-galactosidase expression, where a set of cultures were incubated at 15° C. In the latter case incubation was prolonged to compensate for the lower growth rate.

To secure uniform starting conditions in all cultures, a 5–10 ml preculture of each integrant in liquid G1.5M17 was inoculated with a single colony from GM17 agar (see Example 15 below) and grown to stationary phase by incubation for 12–18 hours at 30° C. From the precultures 10 μl of each strain was inoculated into 10 ml of each medium, and the cultures were incubated at 30° C. for 20 hours or at 15° C. for 165 hours. A sample for measurement of $OD_{600}$ was taken from each culture immediately before harvest. The cells were harvested by centrifugation (10 minutes at 10,000×g, 4° C.) and washed once in 1 ml ice-cold 0.15M NaCl. pH was measured in the medium supernatant. In the case of the duplicate cultures grown at different temperatures where the cultures were harvested on separate days, the cell pellets were frozen at −20° C. and thawed later for the β-galactosidase activity assay. The cells were resuspended in 1.0 ml Z-buffer (Miller, 1972), and the cell suspension was subsequently used for assays of β-galactosidase activity as described in Example 7, except that the proportion between cell suspension and Z-buffer used in the assay was adjusted in accordance with the enzyme activity to keep the reaction rate within reasonable limits.

Results of β-galactosidase assays on selected integrants grown in liquid culture The activity found in the same strain on different days varied to some extent. In ten independent G1.5M17 cultures of Integrant SB the measured activities were between 3.9 and 8.0 with a mean of 6.3 and a standard deviation of 1.4. Five independent cultures of 170 in the same medium gave results between 0.9 and 2.8 with a mean of 1.7 and a standard deviation of 0.7. The observed variation may be caused by some influence on the gene expression or the enzyme stability of undetected differences between medium batches. In each of these cases, however, the difference between activities at low and high pH was obviously significant (Table 10). Activities below 0.1 were not determined accurately by the method used.

Table 10 shows β-galactosidase activities measured in cultures of 17 different integrant strains in media with and without arginine. Most of the integrants showing pH and/or arginine regulated β-galactosidase expression had been identified by plate assays. In Integrants 237, 241 and SB such control of expression had not been clearly observed by inspection of plates. A possible reason is that above a certain activity level it is difficult to distinguish between different activities by the plate assay.

TABLE 10

Expression of β-galactosidase controlled by arginine and/or medium pH as activity in cells from liquid cultures of selected PFC-1 integrants, grown for 20 hours at 30° C. from a 1:1000 inoculum

| Integrant No. | G1.5M17 (final pH 5.6 . 5.8) | ArgG1.5M17 (final pH 6.6–6.8) | 5ArgG1.5M17 (final pH 7.7–7.8) |
|---|---|---|---|
| 86 | 0.8 | 18 | |
| 142 | 1 | 2–3 | 2.7 |
| 159 | 1 | 3 | |
| 162 | 18 | 50 | 140 |
| 163 | 8.5 | 0.3 | |
| 168 | 0.3 | 0.6 | |
| 170 | 1.7 | 0.05 | 0.08 |
| 179 | 4 | 1 | |
| 193 | 7 | 18 | |
| 203 | 0.7 | 0.2 | |
| 222 | 9 | 5 | |
| 224 | 0.4 | 0.6 | 5 |
| 229 | 2.0 | ≦0.1 | |
| 237 | 7 | 15 | |
| 241 | 2 | 5 | |

TABLE 10-continued

Expression of β-galactosidase controlled by arginine and/or medium pH as activity in cells from liquid cultures of selected PFC-1 integrants, grown for 20 hours at 30° C. from a 1:1000 inoculum

| Integrant No. | G1.5M17 (final pH 5.6 . 5.8) | ArgG1.5M17 (final pH 6.6–6.8) | 5ArgG1.5M17 (final pH 7.7–7.8) |
|---|---|---|---|
| 242 | 2 | 0.01 | |
| SB | 6 | 18 | 36 |

A blank space indicates that this particular combination of and medium has not been tested.

Ten strains in which β-galactosidase activity during growth on GM17-agar plates varied with temperature were grown to the stationary phase in duplicate cultures in G1.5M17 at 30° C. and at 15° C. The activities measured in the cells are shown in 11.

TABLE 11

Dependence on temperature of β-galactosidase activity expressed in selected PFC1-integrants grown in liquid cultures, measured after growth at 30° C. for 20 hours and at 15° C. for 165 hours, respectively, in G1.5M17 from 1:1000 inocula

| INTEGRANT NO. | 30° C., 20 hrs. | 15° C., 165 hrs. |
|---|---|---|
| 143 | 0.8 | 1.5 |
| 159 | 0.6 | 1.4 |
| 170 | 1.8 | 11 |
| 172 | 1.4 | 0.9 |
| 187 | 1.3 | 1.0 |
| 188 | 1.3 | 0.9 |
| 192 | 0.14 | 1.7 |
| 201 | 1.0 | 0.8 |
| SB | 3.9 | 8.5 |

Integrants 170 and 192 exhibited the regulation of β-galactosidase gene expression also found in the plate, both giving higher activity at low temperature. For the Integrants SB, 143 and 159, the effect of temperature on β-galactosidase gene expression was opposite to that expected from the results of plate assays, and for Integrant 172, 187, 188, and 201 the effect was weaker than anticipated. It must be taken into account that the cells from the liquid cultures were harvested in stationary phase, whereas the β-galactosidase activity detected in the plate assay is accumulated from both the growth phase and the stationary phase.

Plate assays of PFC-1 integrants had revealed either decreasing β-galactosidase gene expression or no change in response to addition of NaCl to the growth medium. The results of activity measurement in cultures grown in liquid medium containing 1% or 2 2% NaCl are shown in Table 12. For the integrants 179, 199, 230, and 241 it was expected from plate assays that NaCl would reduce β-galactosidase activity. Several integrants that had not shown any influence of NaCl on β-galactosidase activity in plate assays were included in these experiment, and results from three of these, namely 224, 229 and SB, are also presented in the Table.

In all strains tested activities had decreased by a factor of 3–30 in media containing extra NaCl, and apparently the strongest effect was on activity in SB. As mentioned earlier, the final pH of the cultures in NaCl-containing media was slightly lower than in cultures grown without additional NaCl. However, this pH difference may not be large enough to account for the clear effect on SB gene expression, nor is it likely to explain the similarity of the effect on all strains tested. More controlled experiments are needed to elucidate the apparent contradiction between the results of the plate assay and the activity measured in liquid overnight cultures.

TABLE 12

Effect of NaCl in medium on β-galactosidase activity in cultures of selected PFC-1 integrants, grown for 20 hours at 30° C. from a 1:1000 inoculum. A blank space indicates that this particular combination of strain and medium has not been tested.

| Integrant No. | G1.5M17 (final pH 5.6–5.7) | G1.5M17-NaCl (final pH 5.5) | G1.5M17-2 NaCl (final pH 5.4) |
|---|---|---|---|
| 179 | 3 | | 0.4 |
| | 2 | 0.7 | 0.09 |
| 199 | 0.12 | 0.04 | 0.02 |
| 230 | 0.15 | | 0.01 |
| | 0.3 | 0.1 | 0.01 |
| 241 | 2 | | 0.3 |
| 224 | 0.5 | | 0.04 |
| 229 | 2 | | 0.14 |
| SB | 6 | 0.6 | 0.3 |

The following integrants (host organism: *Lactococcus lactis* MG1363): SB, P139-86, P139-142, P139-143, P139-159, P139-162, P139-163, P139-168, P139-172, P139-179, P139-187, P139-188, P139-192, P139-193, P139-199, P139-201, P139-203, P139-222, P139-224, P139-229, P139-230, P139-237, P139-241, and P139-242 were deposited with the DSM-Deutsche Sammlung von Mikroorganismen und Cellkulturen GmbH, Mascheroder Weg 1b, D-38124 Braunschweig, Germany on 22 Dec. 1993 under the accession numbers DSM 8834, DSM 8835, DSM 8836, DSM 8837, DSM 8838, DSM 8839, DSM 8840, DSM 8841, DSM 8842, DSM 8843, DSM 8844, DSM 8845, DSM 8846, DSM 8847, DSM 8848, DSM 8849, DSM 8850, DSM 8851, DSM 8852, DSM 8853, DSM 8854, DSM 8855, DSM 8856 and DSM 8857, respectively.

EXAMPLE 12

Sequencing of *Lactococcus lactis* chromosomal DNA upstream and downstream of Tn917 insertion in selected Tn917-LTV1 promoter fusion integrants The chromosomal sequence of about 200 bp to 1500 bp upstream of Tn917 insertion was determined in six selected Tn917-LTV1 *Lactococcus lactis* promoter fusion integrants. In one of the selected integrants, the sequence downstream of the transposon insertion was also determined. The sequencing was done to present examples of sites and regions on the chromosome of *Lactococcus lactis* showing regulated expression of inserted promoterless gene(s). Sequencing was performed on both strands essentially as described in the manual for Sequenase Version 2.0 DNA Sequencing Kit from USB, Cleveland, Ohio, U.S.A., using the integrant fragment plasmids (see Example 8) pSB, pl70, pl43, p242, p224, and pl63, as templates and primers as described below. We defined Lactococcus DNA located next to the lacZ proximal end of Tn917-LTV1 to be upstream of transposon insertion. Regardless of which strand being mentioned, to move away from the lacZ end is to move upstream on the Lactococcus DNA. The strategy for sequencing upstream on each template was as follows:

1. The first sequence reaction was performed using the primer pp1 (5' GTTAAATGTACAAAATAACAGCG'3SEQ ID NO:11) (DNA Technology, Århus, Denmark). pp1 is homologous to a sequence in the lacZ proximal end of Tn917-LTV1. If the first bp upstream of Tn917-LTV1 is designated No. 1, the complementary sequence to pp1 is located at bp No. −58 to No. −80. The obtained sequence, designated pp1-sequence, consisted of about 20 bp of the lacZ proximal end of Tn917-LTV1 followed by 200 to 300 bp of adjacent, upstream *Lactococcus lactis* DNA sequence.

2. Based on the pp1-sequence the primer p1 was synthesized (DNA Technology). p1 is homologous to a 20 to 24 bp sequence located about 60 bp from the 3' end of the pp1-sequence. The second sequence reaction was performed using the primer p1. The obtained sequence, designated pp1-sequence, was an overlap of about 20 bp of the 3' end of the pp1-sequence and extended 200 to 300 bp further upstream on the *Lactococcus lactis* DNA.

3. Based on the pp1-sequence two primers, p2 and p1r, were synthesized (DNA Technology). p2 is homologous to a 20 to 24 bp sequence located about 60 bp from the 3' end of the p1-sequence and p1r is homologous to the complementary *Lactococcus lactis* DNA sequence located about 250 bp upstream of transposon insertion. The third and fourth sequence reaction was performed using the primers p2 and p1r, respectively. Using the primer p2 the obtained sequence, designated p2-sequence, was an overlap of about 20 bp of the 3' end of the p1-sequence and 200 to 300 bp further upstream on the *Lactococcus lactis* DNA. Using the primer p1r the obtained sequence, designated p1r-sequence, was complementary to the pp1 -sequence.

4. Additional sequence reactions were performed using the primers p3, p4, etc., each primer homologous to a sequence located about 300 bp upstream of the previously used primer.

Also, sequence reactions were performed using the primers p2r, p3r, etc., each of which are homologous to a sequence located about 300 bp upstream of the previously used primer.

5. Cloning of the sequence located downstream from the Tn917-LTV1 insertion in Integrant SB: When the Tn917 derivative, Tn917-LTV1 is used for transposon mutagenesis, the DNA located upstream of the insertion point can easily be cloned in *E. coli* as described in Example 5. However, this cloning method can not be used for cloning DNA located downstream of the Tn917-LTV1 insertion. However, using the Inverse Polymerase Chain Reaction strategy (Ochman et al. 1988) the DNA located downstream of the transposon in Integrant SB was amplified and cloned in *E. coli* in the following manner:

60 ng of chromosomal *Lactococcus lactis* MG1614 DNA was completely digested with EcoRI. The digested DNA was phenol/chloroform extracted and precipitated with NaAc and EtOH. The DNA was subsequently ligated in a total volume of 20 μl. This diluted concentration favours the formation of monomeric circles. From this ligation mixture a 5 μl sample was taken and a PCR amplification was performed in a total volume of 100 μl. The two primers BA24:(5° CCAGTCAACTTTAAAACATAACC3', SEQ ID NO:12) and BA21:(5° CTCACTGGTCACCTTTATCC 3', SEQ ID NO:13) were used for the PCR amplification. A GeneAmp DNA Amplification Reagent Kit from Perkin Elmer Cetus, 761 Main Ave., Norwalk, Conn. 06859 was used. The concentration of reaction buffer, dNTPs and Taq polymerase was as described in the protocol from the manufacturer. The final concentration of the primers in the reaction mixture was 10 ng/μl. The following temperature profile was used: Denaturation at 94° C., 1 min.; annealing at 53° C., 1 min.; extension at 72° C., 2 min. The total number of PCR cycles were 40.

When 10 μl PCR reaction product was analyzed on an agarose gel, one specific band of about 1400 bp was observed, indicating the cloning of about 1100 bp downstream of the Tn917 insertion in Integrant SB.

The 1400 bp fragment from the PCR reaction was ligated to the pT7Blue(R) vector (Novagen, Madison, Wis., U.S.A.) under standard ligation conditions as described by Maniatis et al. 1982. The ligation mixture was introduced into *E. coli* DH5α The resulting plasmid was designated pSBC1.

The subsequent sequence reactions were performed using the same strategy mentioned above in paragraphs 2, 3 and 4.

In the following, DNA sequences upstream of Tn917-LTV1 insertion in Integrants SB, 170, 143, 242, 224, and 163, respectively, are shown [(i)–(vi)]. For Integrant SB a DNA sequence downstream of Tn917-LTV1 insertion in Integrant SB is also given. The site of transposon insertion and orientation of Tn917-LTV1 is shown by [lacZ--Tn917-LTV1-] inserted into the sequences.

(i) The DNA sequence of 117 nucleotides upstream of the lacZ proximal end of Tn917-LTV1 and a DNA sequence of 1.083 nucleotides downstream from the lacZ distal end of Tn917-LTV1 in Integrant SB (SEQ ID NO:14).

A putative transcription terminator is indicated with lower case letters and the −35 and −10 consensus sequences of the promoter, PSB is underlined.

1(5')CTGGTCACCT TATCCATTG AAAATTGATA ACAAAGGATT ACAAGTagaa −31
51 gaatctgtat tttaatacag gttcttttG TTGATTATTT TATAGATAAA −10
101 ATGATATAAT CATTAAA [lacZ---------Tn917-LTV1----------------------------] GCA AAAAAGAATG TAAAG-TAGTT CACTAACTTT
151 CGTTTTATTT GTCAGAATAA GGTTTTTGAT TTATCATTTT TTTAAAGTTA
201 AAAGTAATGA ATTATTAAAT TTCTTCTAAT GACAAAAAAT GTGATTTAAA
251 TGAGAAACCA CGATTGCCCT ACTGTCCGCT TTTTTAAAGC AAGAGTTTAT
301 AAAGAAAAGG AAACTCAAAT GACTCAAACA AAAAAGGCAA AAGTCAGAAA
351 TCTGATTATT GCTGCGATGC TTACTGCACT TGGAATTTTA ATTCCAATGA
401 TGATGCCGGT TAAACTCATT ATTGGCCCAG CCTCATTCAC GCTTGCTGCA
451 CATGTTCCGG TAATGGCTGC CATGTTTTTC AGTCCACTTA TGACTGCTTT
501 TGTTGCTCTG GGAACAACTC TCGGATTCAT GATTAGTATT CCGGTGCCAA
551 CAATTTGGTT GCGCGCGCTG ATGCACCTTC CTGTAATGAC TGTTGGTGCC
601 TATGTCTTGA AAAAATATCC AGAATTTGTT CAT-CAAAAAG TTAAAATCCA
651 AATCTTTAAT TTTATTCTCG GTATTTTTCA TGCTGGTTTG GAAACTTTAG
701 TTGTTTATGC TTTTTATTCT CTAGGATTTG CGAATATTGA GCAAGGTGCT
751 TTATTGAACT TCCTCTTATT GATTGCTCTT GGAGGACTTG TCCATAGCAT
801 GATTGACTTC AACTTAGCGC TTGGTTTGGG TAATGTTTTG AGTAAAGCCT
851 TTCCTATTGA CATCTTTGAT AAAGCTAAAA ATCTTGTGAA TAAAAAGAAA
901 GTTAAAGCCG AAATTTAAGA CAAAATTGTC ATCTTTAATA GAAAATGATA
951 AAATAAGGTT ATGATAAAAG AAACTGATCT TGAAAATATC CCAGATTTAC
1001 TGATTAAATT TAATGAACCC CTATCAAATT ATACTTACAC AAAAGTAGGA
1051 GGACCAGCTG ATATTCTGGC TTTTCCGGCT ACAATAGAAG CATTGACAGA
1101 ACTGTCAGCA AAAGCGAACA GACTGATACA CCGGTTACAG TTCTTGGAAA
1151 TGCCTCAAAT TTGATTGTTC GTGATGGTGG AATTC(3')

(ii) The DNA sequence of 1.430 nucleotides upstream of the lacZ proximal end of Tn917-LTV1 in Integrant 143 (SEQ ID NO:15)

1(5')CATCATTTAT TTCAAAGTAT AAAAAAAATC AATGGAAAAG TTGTATGGAT
51 TAATATCAGT TTTCTTTTCG TATTATCACT AAT-TCCTATT TTTTCAAACT
101 GGGTATCAAT ATATCCCAAT TCATTTATTC CAGAACTAGG TTATGTCATT
151 ATCTTTTTCT TTGGAAACTT CATCTACTTT CTATTAACAA GGGAATTATT
200 AAAAATTAAT GGTCACCGTA AAACTTCTGA ATCAACTGTA AGAAAAAATA
251 TCATCAGTGT TGGACTTAAT GTCATTAGCA TTATTCTTGG ATATTTTATT
301 GCACCGGTGA TTATGCTCAT TGCTTCGGCG TTGATTTTTT CAATGTGGGT
351 CATTCCAGAT AAGAACATTG AAAAAATGTT TAAATAAGTA TTTTATAAAA
401 ATAGAATTTG TATCAAGAAA AATTTGGAAA AACTGACTAA ATTGTCTGTC
451 AGTAAATTAA ATATAAATTG AGGAGAAAAT AATGATTAAA GCATACATTA
501 AATATTGGAA AAAAGCAGGC GATTTCAAAA CATATTCAAG TCGTTCAGAT
551 TACTGGTGGG TTTTCTTGGC GAATTTCATT ATCTTTGCTA TTCTAAGCTT
601 TTTTAATTTT ATGATTATGA TACCAAGAGC TGC-CAAAATC ATGAATCAAG
651 CAGGTGACTC ATCTCAAACA GAAATCATTC GACAAGTCAC GGATTTATAC
701 ACAAATCCTA CAGGTGGAGC ATTAGTGATT ATTATCATTA CAGCTATTGC
751 TGGTTTGGCT ATTCTTATTC CAAGCGTTAG TCT-GACAGCC CGTCGTTTGC
801 GAGATGCACG TCTTCCTTGG TGGATTTCTC TTATCTTTGG TTTAGCAGCC
851 ATTTATGGTT TACTTACAAT GTTTATTCAT CAA-GAAATGC TTCAACAGTT
901 AGGATTCATT TTTAACTTAA TCACTTTCAT TGTCTATATC CTCTGTCTTT
951 TCCCAACAAA ATATGGAGTT GAGGAAGAAG ATGACTCAAG ATCTTATGAA
1001 TAGTACAAAA AAGAAAGGTA AAATATGATA CAAGCTTATA AAAAATATTG
1051 GCAAGGGACT TTTGTTTCA ATAAAAGAAC AAGTCGTAAG GATTTTTGGA
1101 TGGCTTTATT CACCCATCTG ATTATTTTTG TGGTTTTACT AAAGGGCTAT
1151 AATTTTTTTA ACGGATTGGG TTATTTCCCA CTGTCAGTTT TATGGCAATC
1201 AATCGGTTCA TTTTTACTTT GGCTTTTGTG GATATATTTT TTAGGAAGTT
1251 TACTAGCCTT CTTGGCCATA ACAGTTCGAC GATTAAATGA TACTGATTTG
1301 CCTTGGGGAT TAGTATTTCT AAATCTTGTT TTTGGCTTAG GAACTCTTGT

1351 ACTATTGGTT CTCAATTTAT TTCCAAGTTC TCCTAAAAGA GACAAGTTTA
1401 AAGAGTTTGA ATTAAAAAAT AGTTCTAATT [lacZ-Tn917-LTV1](3')

(iii) The DNA sequence of 994 nucleotides upstream of the lacZ proximal end of Tn917-LTV1 in Integrant 163 (SEQ ID NO:16)

1(5')TTTTCATTGC CTACATTGGG ATTAAAAACG CTGGAATTTT GCGCTTCATC
51 GCTGACCCAG GAACTTATGT GAACAATCAC GGAACAATTA CAGCAAATTC
101 ATCAATTGTT CCAGAGCTTG TAACTTTTAA TAACCCAGGA GTGTTGGTAG
151 CACTTGTTGG GATTGTCGTG ACAATGTTCT TTGTCATTCG TAAATGGCGG
201 GCAGGGATTT TGCTTTCAAT CTTGGTAACA ACTATCTTGG CTCTTTTGAC
251 TGGCGTGGTT AAAGTTGATG TGAATACTTT ATTTGCTGAA AATAATTTGG
301 GGACTGCAAT CAATCAAATG GGAACAACCT TTGGTGCAGC ATTTGGTCCA
351 AAAGGATTTG GTTCTTTATT CTCTGATTCA TCACGTTATA TTGAAGTATT
401 AATGACAGTT CTTGCTTTCT CATTGACTTC AATCTTTGAC CCAATCGGAA
451 CTTTCATCGG AACTGGTCGC GCGACAGGAA TCTTTACTGA TGAAGATTTG
501 AAAGACATGG AAACAAGCCA TGGTTTCTCA TCAAAAATGG ACAAAGCTTT
551 GTTTGCTGAC ATGATTGCTA CTCCAATCGG AGCAATTTTC GGAACATCAA
601 ATACAACCGT TTATGTTGAG TCTGCTGCCG GAATCGGTGC AGGAGGACGT
651 ACTGGTCTTG CATCAGTTGT AACAGCAATT ATGTTTGCTA TCTCAAGCTT
701 GTTCTTACCA CTTCTTGCGA TTGTTCCAAC ACAAGCAACA GCACCAATTT
751 TGATTATCGT TGGGATGATG ATGCTTGGTT CATTTAAAGA AATTAAATGG
801 GGTGATTTGA CAGAAGCGAT TCCTGCTTTC TTCGCCTCAG TATTCATGGG
851 ACTTGCTTAT TCAATCTCTT ACGGGATTGC AGCTGGATTT ATCACTTATA
901 TCCTTGTCAA ATTATTCACC GGAAAAGTGA AAGAAATTAA ACCTGTAATT
951 TGGGTCGTTG CTCTCTTGTT CTTAATTAAC TTTGGGGTCC CGAG [lacZ--Tn917-LTV1-](3')

(iv) The DNA sequence of 1.120 nucleotides upstream of the lacZ proximal end of Tn917-LTV1 in Integrant 170 (SEQ ID NO: 17)

1 (5')TGTCGTTTTT TCTTCCAAAT AAACGACAAT ATGATTGTAC TGCGCTCGAT
51 TAGGAAAGAC AAATGGAAAA AGAATCCAGC AAAAATGGAA TAAGCACTCC
101 AAACCAACTC AGAATAGCCA CCAATGTTTG AAATATTTTA CTCCCATAAT
151 TCCCTTTTTC AAAATACGGG TCATAAACTA AAGATTTTTT CGCCTCTTCA
200 CGGCTCAAGT TTTGTTTCAT TTCCGACCTT TCTGAACTTT TCAACCTTT
251 ATAGTTATAG TCAATACAAT ACATTTTCTT TAAT-TATCTC ATTTTTTGTT
301 CACAAAAGCC ATTTTATGAG TCTATTTTTA ATTACAAAAA ACAGTCAGAC
351 ACTCTATCAA ACTGCTTTAT ATTTATTATT TATAATGATA ACAGTCGATT
401 CTCCTTTTTT ATCAACTTTT GCTTTATGCT ATAATTTACA GATAAGAACG
451 ATCTACCTAA AAAGGTTAAA GGAGTATTAT GATAAAAATT TTAAAAATGA
501 CTCAAGATGG CTTTGACCAT TATATGTTGT CCGCTATTAA AAATTATGCT
551 AATGAGAAAG TAAATAATGG AACATGGGAG TCTAAAGATG CCCTTTCAAA
601 TTCAAAGAAA CAGTATGCAC TCCTGCTTCC CGACGGCTTC AAACTGCTAA
651 TCATTATTTT TACTCAATTT TTAATAAAGA AGAAAAAATC GGATATATCT
701 GAAATTTATG AAGAATTTCA AAATCTAGGA TTTGGCTCAA AAACCCTTGA
751 TTTAGTTGCC GATAAAGCAA AAGAACTTGG ATTCTCTTTT TTGGGACTCC
801 ACGTTTTTGG AAGTAATTCT AGAGCTTTGC ATGTCTATAA AAAAATGGGA
851 TTCCAAATTA CCGATATCAA TATGCGAAAA GAACTATGAA TATCCACTCC
901 ATTTTTGGTT GCCATTTGTT AACGCTGCCT CCTCTCCCTA GTGCTATAAT
951 AAAAATGGCC AAAAAAAAAC CATTTTATTG ACTATATTTG CAATTTATTT
1001 ACACATTATC TTTTCAGAAC CAAAATCTGG CCCATTTTGG AACAGACTTC
1051 TACTATTTTG TTGTCTAGTA [lacZ-Tn917-LTV1-](3')

(v) The DNA sequence of 480 nucleotides upstream of the lacZ proximal end of Tn917-LTV1 in Integrant 224 (SEQ ID NO:18)

1(5')GAATTCTTGA TTCAATGAGA GCTATTATGC TTATCGTCGA ATTAGAAGGT
51 GCATTTGATA TTAGTCTTCC ACCATCAGAA ATG-GACCGTG AAGATTGGAA
101 TACAGCAAAT AAAATAGCAG CACGCGTTCA GGAAAAAACG GATGAAAATT
151 AAAATTTTTA GAGCAATTGG CCCACTAATT GCAGCTTTAG TTCTCGTTGC
200 TTTATTAATA TTTCTCCCTT TTAACGTTG GAATGAAATA TTCTAAAGAC
251 CAACTCGTTA AGTTTGCACA GTCACCCTTA AATACACCTA CTTTTACAGG
301 ATATTCAATT AAGAAACAAG CCTATTCAGA TCCTGAATTT TTACCAGTTC
351 TCGGTTCGTC AGAAATGGAA CACGTTGATT CATTTCACCC AAGTGCTTAT
401 TTCAGCAAAT ATAATTCAGG TTTCATACCA TTTTTAGTAG GACAACCCGG
451 AACAACGACA TTAACTCACT TTTTCTATAT [lacZ-Tn917-LTV1-](3')

(vi) The DNA sequence of 853 nucleotides upstream of the lacZ proximal end of Tn917-LTV1 in Integrant 242 (SEQ ID NO:19)

1(5')TTAGAACGTC AATGAGATAG AAAAACAAAA TATTTAAGAA TAAAATGATA
51 CTGTTTTCCT TAACTTAATG ACATTGGGGT ATACCCTGTT GTCCATCAAA
101 AAAAATCTTC TAAAATTATT TTACTCAAAT TGATAGATTA TTTTTATGAA
151 ATGTGTTAAC ATTTATTACT ATCTAAATAG CCA-GAAAATT CTACAATAGA
200 GTTATAAATT AATGGAGACT CTATATGAGA AAAAATAAAA CCAAGTTTAT
251 TGCTTTTGCA CTTGCTTAAG CAGTTATTGC AGTAGGTTAC TCAACTGCAG
301 CTTCTGCTGA TTCTGTTACT TCCTCAGATA AAGATACAGT CTCAAATCCA
351 ATTCTGACAA TTACACCTCG TATGAATGTT GAGTTTCAAG GTGGTGGATA

401 TTGGACAAAT ACTTCGCACC TGACCTACAT TCAAAATACA GGTTCTGGAG
451 TACTGTATTA TGACCGAGTA AATCATAAAT ATGTATTTTC ACAAACAAGA
501 GGTGCAATGG GTGCAGCTAT TTATGTTTTT AACGCTCAGG GTGTAAACTG
551 GTATAGAGGA GTACTTTATG TTTAAGAGTA AAAAAAATGA TGAGAAGAAG
601 GTTGAAATAC TCAATTCTAT TGATAAACTT CTTCATCAAG ATGTTGAATT
651 AACAATAGAC GAAAAAGAAA TACTGTTAAA ATATAAAGAG CGGATTCAAA
701 ATTCAAAAAA TATTGAATTT GAACTGATTC ATCTTAGAAA TGCTCTTCTT
751 CCATTTGTTA TAAGTTCGAA ACTTTCCGAA CCTACATTAA ATTTCTATAA
801 AAAAATACGA GCAGATAGAA AAATTAGATG GGGAGAAGGT AGCTCTCTAA
851 TTA [lacZ-Tn917-LTV1-](3')

EXAMPLE 13
Mapping af the promoter. P170 on the 9.7 kb EcoRI-ClaI DNA fragment from p170

The following experiments were carried out to map the location of the pH/growth phase regulated promoter, P170 on the 9.7 kb ClaI-EcoRI fragment of p170.

Figure 16:
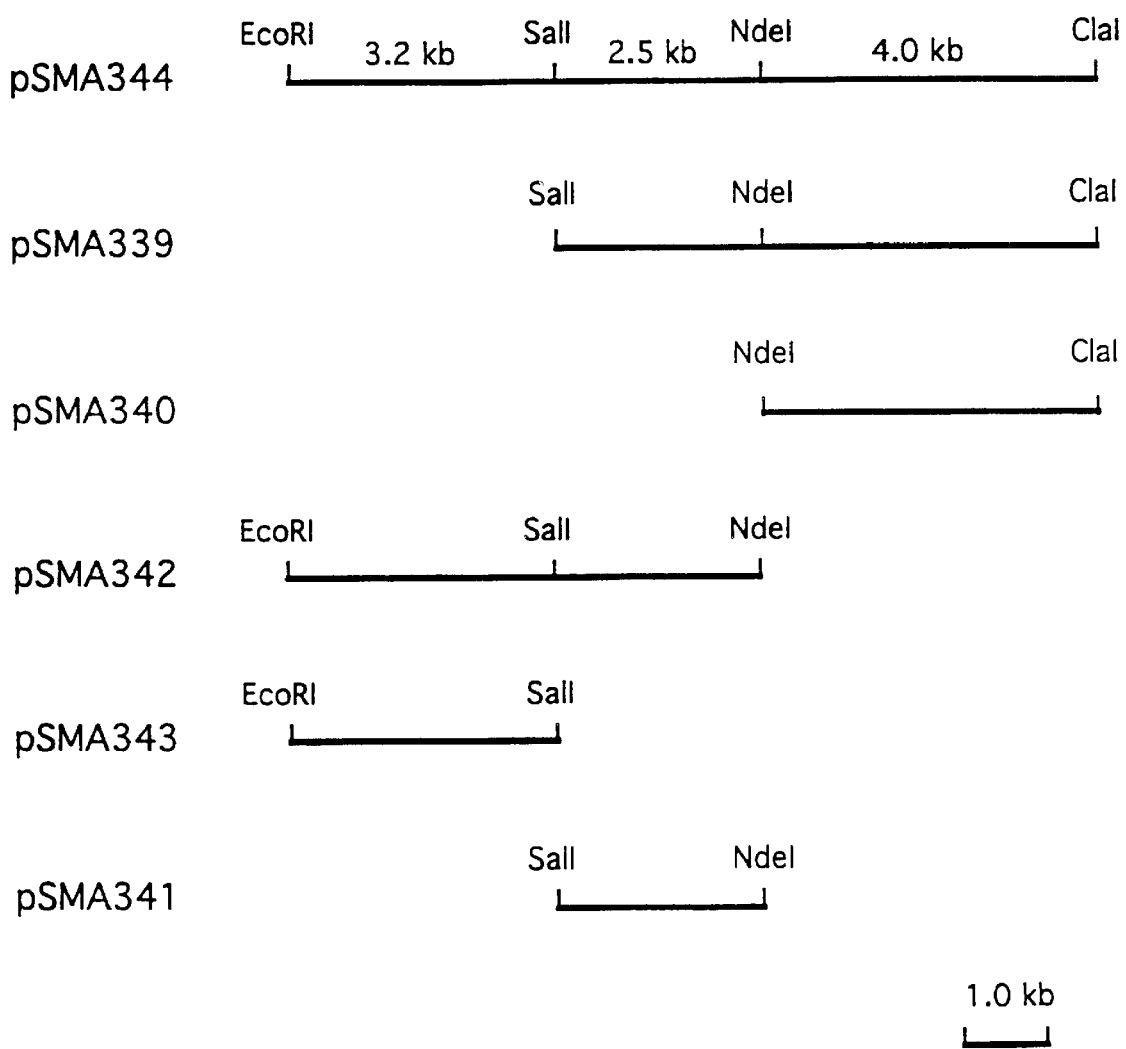
FIG. 16 is a restriction map of a 9.7 kb lactococcal EcoRI-ClaI fragment from p170 and of deletion derivatives.

The 9.7 kb ClaI-EcoRI fragment of p170 was cleaved into subfragments and a restriction map was created (see FIG. 16). Appropriate subfragments were subsequently cloned into the promoter probe vector pAK80. However, it was necessary first to create compatible restriction sites on the subfragments and pAK80.

(i) Construction of pSMA344

Cloning of the large 9.7 kb ClaI-EcoRI fragment from p170 into pGEM-7Zf(+) was done by digesting p170 with ClaI and EcoRI followed by ligation of the 9.7 kb fragment to pGEM-7Zf(+) digested with ClaI and EcoRI. The ligation mixture was introduced into E. coli DH5α and the resulting plasmid was termed pSMA212. pSMA212 was digested with XhoI and BamHI and ligated to pAK80 also digested with XhoI and BamHI. The ligation mixture was introduced into E. coli DH5α. The resulting plasmid, pSMA344, was subsequently introduced into Lactococcus lactis MG1363.

(ii) Construction and cloning of deletion derivatives of the 9.7 kb ClaI-EcoRI fragment from p170

Plasmid pSMA342 was constructed in the following manner: pSMA212 was digested with ClaI and NdeI, the sticky ends were filled in by use of Klenow polymerase as described by Maniatis et al. 1982. The large 8.7 kb fragment [3kb from pGEM-7Zf(+) and 5.7 kb from the Lactococcus chromosome] was purified, religated, and introduced into E. coli DH5α. The resulting plasmid, pSMA213, was digested with XhoI and BamHI and the purified 5.7 kb fragment was ligated to pAK80 also digested with XhoI and BamHI. The ligation mixture was introduced into E. coli DH5α and the resulting plasmid, pSMA342, was subsequently introduced into Lactococcus lactis MG1363.

The plasmid pSMA343 was constructed in the following manner: pSMA212 was digested with ClaI and SalI, the sticky ends were filled in by Klenow polymerase. The 6.2 kb fragment [3kb from pGEM-7Zf(+) and 3.2 kb from the Lactococcus chromosome] was purified, religated and introduced into E. coli DH5α. The resulting plasmid, pSMA214, was digested with XhoI and BamHI and the 3.2 kb lactococcal fragment was ligated to PAK80 digested with XhoI and BamHI. The resulting plasmid, pSMA343, was introduced into E. coli DH5α and subsequently into Lactococcus lactis MG1363.

The plasmid pAK80:170 (DSM 8500) as described in Example 8 is in the following designated pSMA339.

Plasmid pSMA340 was constructed in the following manner: The cloning of the 6.5 kb ClaI-SalI lactococcal fragment from p170 into the cloning vector pBluescript II KS is described in Example 8. This construct being termed pBluescript:170 in Example 8 is designated pSMA201 in the following. pSMA201 was digested with NdeI and SalI and treated with Klenow polymerase to fill in the sticky ends. The large 7 kb fragment [3 kb from pGEM-7Zf(+) and 4 kb from the lactococcus chromosome] was purified, religated and introduced into E. coli DH5α. The resulting plasmid was termed pSMA202.

pSMA-202 was digested with XboI and BamHI, and the 4 kb lactococcal fragment was purified and ligated to pAK80, also digested with XhoI and BamHI. The ligation mixture was introduced into E. coli DH5α and the resulting plasmid, pSMA340, was subsequently introduced into Lactococcus lactis MG1363.

pSMA341 was constructed in the following manner: pSMA202 was digested with NdeI and EcoRI and treated with Klenow polymerase to fill in the sticky ends. The large 5.5 kb fragment [3 kb from pGEM-7Zf(+) and 2.5 kb from the lactococcus chromosome] was purified, religated and introduced into E. coli DH5α. The resulting plasmid, pSMA208 was digested with XhoI and BamHI and the 2.5 kb lactococcal fragment was ligated to pAK80, also digested with XhoI and BamHI. The resulting plasmid, pSMA341, was introduced into E. coli DH5α and subsequently into Lactococcus lactis MG1363.

(iii) Assessment in Lactococcus lactis of promoter activity on the subfragments of the 9.7 kb fragment from p170

A plate assay for determination of promoter activity of the cloned lactococcal fragments was performed by plating over-night cultures of Lactococcus lactis containing the plasmids pSMA339, pSMA340, pSMA341, pSMA342, pSMA343 and pSMA344, respectively, on GM17 supplemented with 1 µg/ml Em and 160 µg/ml X-gal. Surprisingly, all cultures appeared blue on these plates, showing the existence of at least one functional promoter on all plasmids. From these results it is evident that at least three promoters are located within the lactococcal 9.7 kb fragment from p170.

The Lactococcus lactis MG1363 strains containing pSMA339, pSMA340, pSMA341, pSMA342, pSMA343 and pSMA344, respectively, were streaked on GM17 plates and on ArgMl7 plates, respectively. Both type of plates contained 1 µg/ml Em and 160 µg/ml X-gal. The platings were done to identify the pH regulated promoter(s) among the three promoters. Based on these assays the β-galactosidase expression arising from pSMA339, pSMA340 and pSMA344, respectively, was found to be regulated by pH/arginine. The β-galactosidase expression arising from pSMA342 was weakly regulated by pH/arginine, whereas the expression from pSMA341 and pSMA343 were unaffected by these factors.

The results demonstrate that the promoter located on the 4 kb ClaI-NdeI fragment proximal to the β-galactosidase reporter gene, is pH regulated. This promoter is in the following referred to as P170. The plasmid pSMA342, which contains the 5.7 kb lactococcal fragment extending from the NdeI site to the EcoRI site, most likely contains two promoters, of which the one located proximally to the reporter gene also appears to be pH regulated. However, this regulation seems to be dependent on the 3.2kb EcoRI-SalI fragment located upstream. This conclusion is based on the observation that the promoter harboured on pSMA341 which lacks the 3.2 kb EcoRI-SalI fragment, is not regulated by pH/arginine.

Measurements of β-galactosidase expression in overnight cultures of strain MG1363 containing pSMA339, pSMA340, pSMA341, pSMA342, pSMA343, and pSMA344, respectively, were performed as described in Example 7. All cultures were grown in GM17 medium and ArgMl7 medium, respectively. Both media were supplemented with 1 μg/ml Em. As a control of regulated β-galactosidase expression, Integrant 170 was included in the experiment. The results are shown in Table 13:

TABLE 13

β-galactosidase expression in deletion derivatives of the 9.7 kb ClaI-EcoRI fragment of p170

| | Miller units in GM17 (final pH 5.6–5.8) | Miller units in ArgM17 (final pH 6.6–6.8) | Miller Units in GM17 vs ArgM17 |
|---|---|---|---|
| Integrant 170 L. lactis MG1363 containing plasmid | 1.7 | 0.1 | 17 |
| pSMA339 | 15 | 1 | 15 |
| pSMA340 | 16 | 1 | 16 |
| pSMA341 | 7 | 7 | 1.0 |
| pSMA342 | 2.1 | 1.5 | 1.4 |
| pSMA343 | 22 | 8 | 2.8 |
| pSMA344 | 14 | 1 | 14 |

*Lactococcus lactis* containing pSMA339, pSMA340 or pSMA344, show the same regulated expression of β-galactosidase as Integrant 170. This shows that the promoter P170 is regulated also when located on the a multi-copy plasmid like pAK80. In contrast, the promoter carried on pSMA342 does not show a regulated expression. The promoter harboured on pSMA343 is regulated by pH or arginine. This regulation was not detected in the plate assay. This might be due to differences in the growth on plates and in liquid medium. The regulation observed on the promoter harboured on pSMA343 is not as tight as the regulation of P170.

Fine mapping of the promoter P170 located on the 4 kb ClaI-NdeI fragment of p170.

Figure 17:
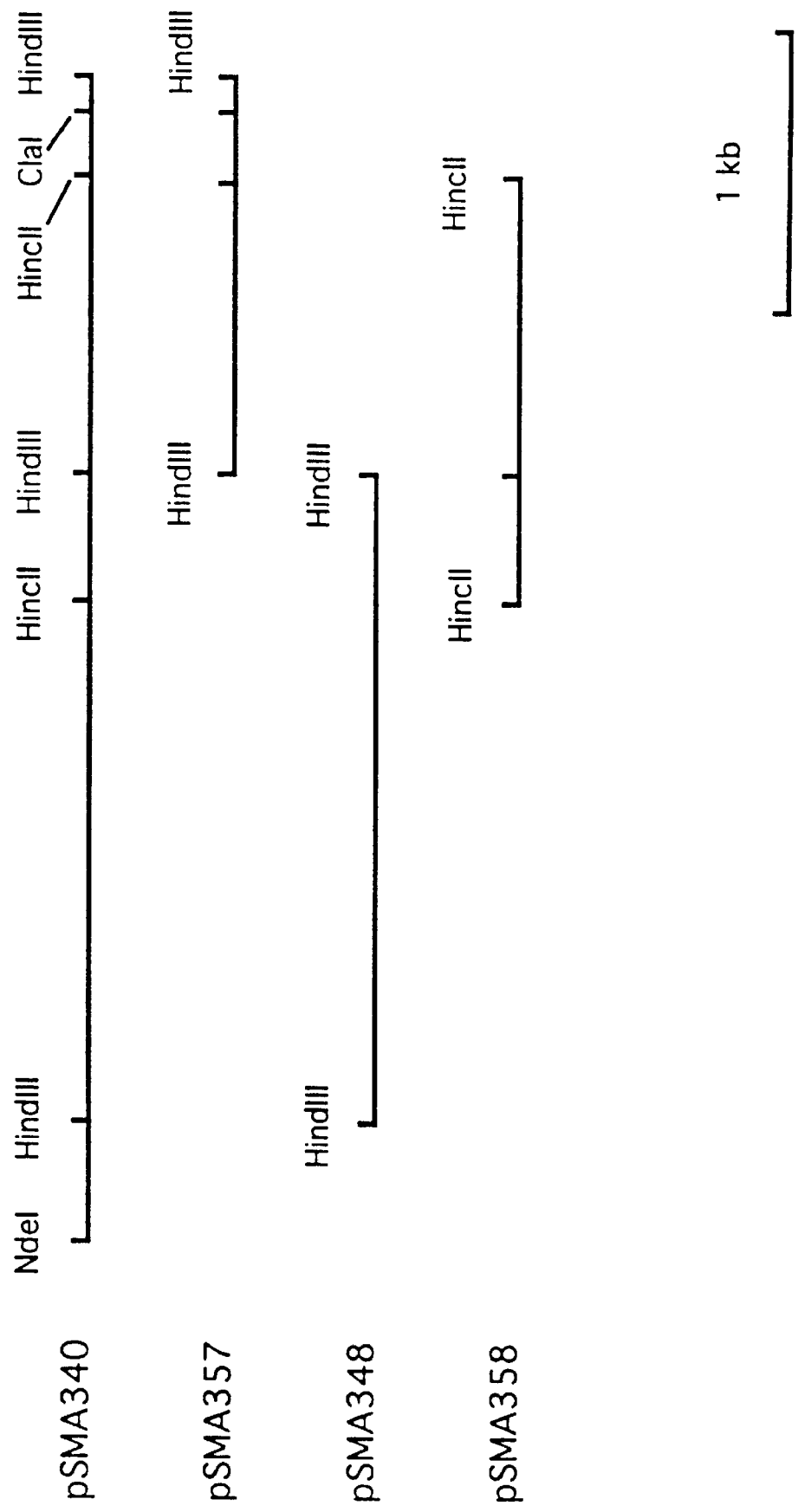
FIG. 17 is a restriction map of a 4.0 kb lactococcal NdeI-ClaI fragment of p170 and of deletion derivatives.

Prior to fine mapping of P170 located on the 4 kb ClaI-NdeI fragment of p170, a more detailed restriction map of the 4 kb ClaI-NdeI fragment was produced (FIG. 17).

The 4 kb ClaI-NdeI lactococcal fragment of p170 is harboured on pSMA202. pSMA202 contains three HindIII sites, of which two are located within the lactococcal DNA and one in the polylinker region. Insertion into pAK80 of the 1.3 kb HindIII fragment, extending from the HindIII site in the polylinker to the HindIII site in the Lactococcus DNA resulted in the plasmid, pSMA357. The insert in pSMA357 contained no promoter activity when introduced into *Lactococcus lactis* MG1363.

The 2.3 kb. HindIII fragment on the 4 kb ClaI-NdeI fragment was cloned into pAK80 digested with HindIII. The resulting plasmid, pSMA348, was introduced into *Lactococcus lactis* MG1363. From this plasmid β-galactosidase was expressed, which demonstrates the existence of a functional promoter within this HindIII fragment. A 1.5 kb HincII fragment was inserted into the SmaI site of pAK80 and the resulting plasmid, pSMA358, was introduced into *Lactococcus lactis* MG1363. β-galactosidase was expressed from pSMA358. The 1.5 kb HincII fragment covers most of the 1.3 kb HindIII fragment and has a 400 bp overlap with the adjacent 2.3 kb HindIII fragment. Based on promoter activity assessments on the inserts in the plasmids pSMA348, pSMA357 and pSMA358, the promoter P170 was mapped to a 400 bp HincII-HindIII fragment located about 1.3 kb upstream of Tn917-LTV1 insertion in Integrant 170.

(iv) Mapping of the promoter PSB

From the sequencing of the upstream located DNA of SB a consensus promoter was identified [see Example 12 (i)] within a 190 bp HpaI-ClaI fragment. pSB was digested with HpaI and ClaI and the fragment was ligated to pNZ336 (Simons et al. 1990) digested with HpaI and ClaI. The resulting plasmid, pNZ336:SB, was digested with SalI and BamHI. The 190 bp fragment was ligated to pAK80, digested with XhoI and BamHI. The ligation mixture was introduced into *E. coli* DH5α, and the resulting plasmid, pSMA347 was subsequently introduced into *Lactococcus lactis* MG1363. Strain MG1363/pSMA347 expresses β-galactosidase, which demonstrate the existence of a functional promoter on the 190 bp fragment.

(v) Measurements on induced and non-induced overnight cultures of *Lactococcus lactis* MG1363 containing promoter harbouring PAK80 derivatives.

In Table 14, β-galactosidase activities on overnight cultures grown under induced and non-induced conditions, respectively, are given. The different growth conditions are temperature variations and variation of pH/concentration of arginine in the growth medium, respectively. The strains analyzed include both pAK80 derivatives containing EcoRI-ClaI fragments from the rescue plasmids and, based on the above mapping analyses, pAK80 derivatives containing deletions of the EcoRI-ClaI fragments. The growth of cultures as well as the βgalactosidase assay were performed as described in Example 11. In this example 5Argl.5M17 is designated as 5ArgM17.

TABLE 14a

β-Galactosidase activities in overnight cultures grown at induced and non-induced conditions. Expression controlled by arginine and/or medium pH (30° C.)

| | MEDIUM | | |
|---|---|---|---|
| L. lactis containing plasmid | GM17 (final pH 5.6–5.8) | ArgM17 (final pH 6.6 . 6.8) | 5ArgM17 (final pH 7.7–7.8) |
| pSMA332 | 680 | 560 | |
| pSMA347 | 720 | 620 | |
| Integrant SB: | 6 | 18 | |
| pSMA338 | 70 | 100 | 260 |
| Integrant 162 | 18 | 51 | 140 |
| pSMA339 | 15 | 1 | 0.4 |
| pSMA340 | 16 | 1 | 0.7 |
| pSMA344 | 14 | 1 | 0.5 |
| Integrant 170 | 1.7 | 0.05 | 0.08 |

TABLE 14b

β-Galactosidase activities in overnight cultures grown at induced and non-induced conditions. Expression controlled by temperature (G1.5M17 medium)

| PLASMID | 30° C., 20 hrs | 15° C., 165 hrs |
|---|---|---|
| pSMA337 | 190 | 35 |
| Integrant 143 | 0.8 | 1.5 |
| pSMA339 | 27 | 67 |
| pSMA344 | 21 | 75 |
| Integrant 170 | 1.7 | 14 |
| pSMA347 | 650 | 120 |
| Integrant SB | 6 | 18 |

TABLE 14b-continued

β-Galactosidase activities in overnight cultures
grown at induced and non-induced conditions. Expression
controlled by temperature (G1.5M17 medium)

| PLASMID | 30° C., 20 hrs | 15° C., 165 hrs |
|---|---|---|
| pSMA345 | 36 | 1.4 |
| Integrant 172 | 1.4 | 0.9 |

The results show that the promoter from pSB is not pH regulated when harboured on pAK80. This result is seen with both pSMA332 and pSMA347. The temperature regulation of the promoter from pSB is reversed when located on pAK80. The promoter from p162 is still regulated when located on pAK80. However, the total expression of β-galactosidase from the plasmid harboured promoter is not as high as expected from the high copy number of pAK80. The pH regulation of P170 is described above. The temperature regulation of P170 is conserved, although to a lesser extent, when located on pAK80. The promoter from p143 is regulated when located on pAK80. However, this regulation is opposite to the regulation observed when the promoter is chromosomally located. The strength of the promoter on p143 is increased dramatically when plasmid located. β-galactosidase expression from the promoter on p172 is slightly influenced by temperature when located on the chromosome. This regulation becomes much more pronounced when the promoter is plasmid located.

The results clearly demonstrate that regulation of a chromosomal promoter is in general dependent on the location, i.e. whether it is chromosomally or multicopy extrachromosomally located. It is contemplated that had a conventional promoter cloning strategy including shotgun cloning in a promoter cloning vector been used, the results concerning regulation would in most cases have been quite different from those obtained using the above strategy which included studies on regulation directly on chromosomally located promoters.

EXAMPLE 14
The construction of a vector, pSMA500 that does not replicate in Lactococcus lactis For several microorganisms including Lactococcus it has been shown that a non-replicating vector can integrate into the chromosome, if the vector carries homologous DNA (Leenhouts et al. 1989). The integration mechanism involved is a single cross-over event (Campbell-like integration) between the homologous DNA contained on the vector and on the chromosome. The result of this Campbell-like integration is a duplicate set of the homologous DNA on the chromosome and in between the duplicate set of homologous DNA, the non-replicating vector is located.

In contrast to Tn917 insertion this Campbell-like integration results in a non destructive insertion, if an appropriate integratable vector is used.

A non-replicating vector, pSMA500, was constructed based on the E. coli plasmid pVA891 (Macrina et al. 1983) carrying an erythromycin resistance marker, and, as a reporter gene, the promoterless β-galactosidase genes derived from Leuconostoc mesenteroides subsp. cremoris.

The polylinker and the promoterless β-galactosidase genes from the plasmid pAK80 was cloned into the plasmid pVA891, which is unable to replicate in lactic acid bacteria. pAK80 was digested with HindIII and SalI. The 4.1 kb fragment containing the polylinker and the β-galactosidase genes was purified and ligated to pVA891 also digested with HindIII and SalI. This ligation mixture was introduced into E. coli MC1000, selecting for erythromycin resistance (Em$^r$) (250 µg/ml). The resulting plasmid was designated pSMA500. This vector is not able to replicate in lactic acid bacteria. However, if the plasmid is inserted into the bacterial chromosome, the erythromycin resistance gene is expressed in most lactic acid bacteria. When a functional promoter is cloned into the polylinker of pSMA500 the host bacterium will additionally express the β-galactosidase genes.

EXAMPLE 15
Insertion of a regulated promoter into oSMA500 and integration into the Lactococcus chromosome
(i) Insertion of promoters into pSMA500

The regulation of the promoters from p170 and pSB has been described in Example 8. In the present Example Lactococcus DNA from p170 containing the regulated promoter, P170 was inserted into pSMA500 and this construct subsequently integrated into the chromosome of Lactococcus lactis MG1363. In parallel, Lactococcus DNA from pSB, containing the regulatable promoter PSB, was inserted into pSMA500 and this construct subsequently integrated into the chromosome of Lactococcus lactis MG1614.

This experiment was performed to examine if a regulatable promoter and the β-galactosidase gene inserted into the chromosome via Campbell-like integration still would exhibit regulated expression of β-galactosidase.

(ii) Construction of the integrable vectors PSMA501 and pSMA502 pSMA212 as described in Example 13, contains a 9.7 kb XhoI-Ba HI fragment. This fragment is essentially the same as the 9.7 kb Lactococcus DNA segment of p170, which harbours the regulated promoter P170. The 9.7 kb fragment from pSMA212 was cloned into pSMA500 also digested with XhoI and BamHI. The resulting plasmid, pSMA501, was introduced into E. coli MC1000 and transformants selected for Em$^r$ (250 µg/ml).

In parallel, the 1.8 kb XhoI-BamHI Lactococcus DNA fragment from PGEM:SB (see Example 8), which harbours the regulated promoter PSB, was cloned into pSMA500. The resulting plasmid, pSMA502 was introduced into E. coli MC1000 and transformants selected for Em$^r$ (250 µg/ml). Standard DNA manipulations and transformations were according to Maniatis et al. 1982.

(iii) Integration of pSMA501 and pSMA502 into the Lactococcus chromosome

Figure 18:
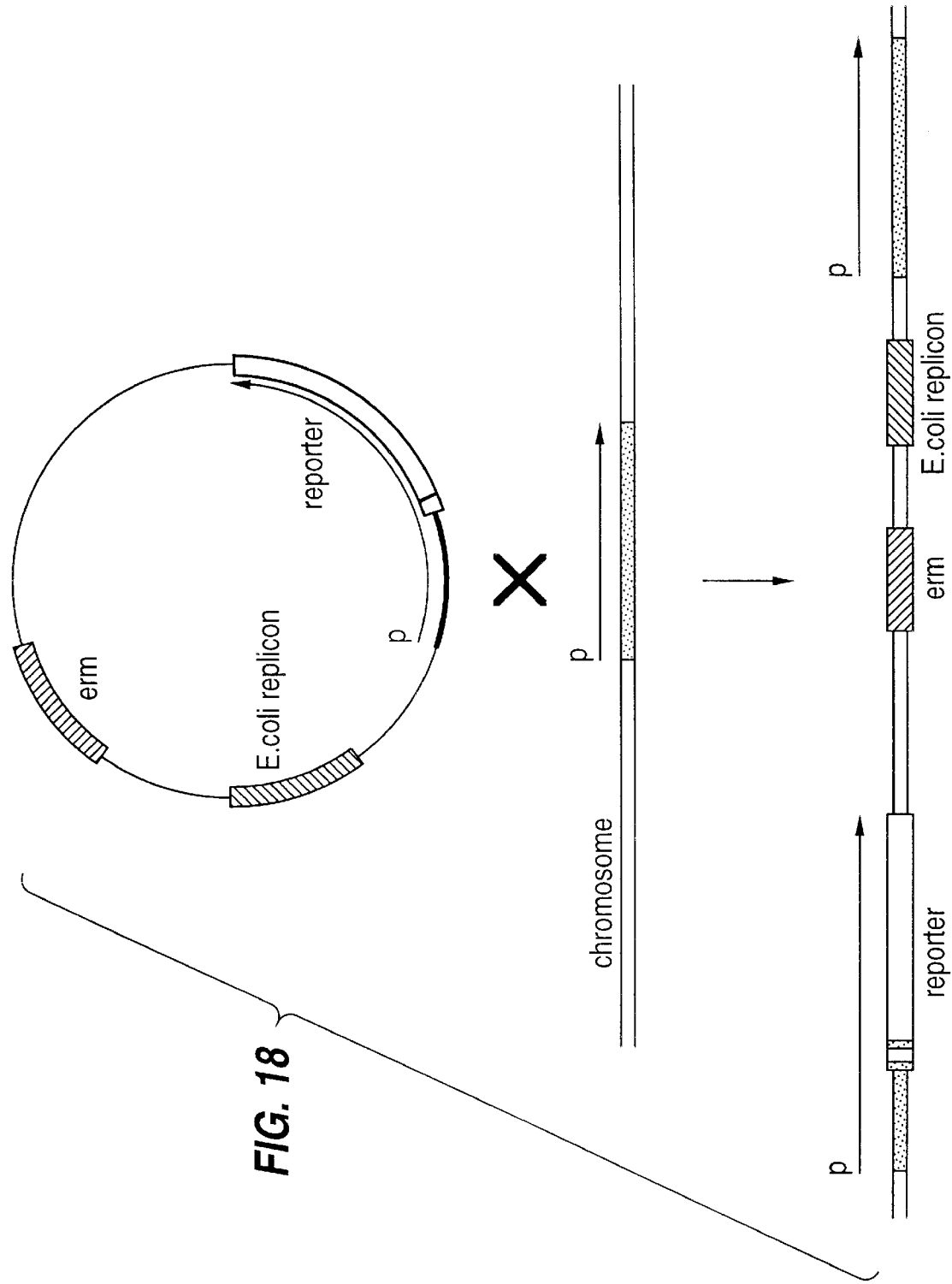
FIG. 18 illustrates the Campbell-like integration of a non-replicating plasmid into the lactic acid bacterial chromosome where P represents a promoter, Erm represent an erythromycin resistance gene, reporter gene is the β-galactosidase gene from *Leuconostoc mesenteroides* and the *E. coli* replicon is the pACYC replicon from pVA891 and where black areas illustrate the region of DNA homology between the plasmid and the chromosome and arrows indicate the direction of transcription from the promoter P.

About 2 µg Qiagen (Qiagen Plasmid Kit, Diagen, Düsseldorf, Germany) purified DNA of pSMA501 was introduced into Lactococcus lactis MG1363. In parallel, about 2 µg Qiagen purified DNA of pSMA502 was introduced into Lactococcus lactis MG1614. Transformation of Lactococcus lactis was as described in Example 1. The transformants were plated on SGM17 plates containing 1 µg/ml Em and 160 µg/ml X-gal. After growth at 30° C. for 48 hours, only blue transformants appeared on both parallel set of plates. These results indicated that pSMA501 had integrated into the chromosome of strain MG1363 and that pSMA502 has integrated into the chromosome of strain MG1614. Also, the results showed that the promoters on pSMA501 and pSMA502, respectively, were functional when integrated into the chromosome. About 5000 colony forming units/µg DNA was obtained using the pSMA501 construction and about 500 CFU/µg DNA was obtained using pSMA502. Using the replicating plasmid pAK80 the transformation efficiency was 1×10EE7 CFU/µg in both strains. Transformation of strain MG1363 and strain MG1614 with pSMA500 showed less than 5 CFU/µg DNA, which clearly demonstrated that the integration of pSMA501 and pSMA502 was mediated by the chromosomal Lactococcus insert on these vectors. Ten primary, randomly picked transformants from each parallel set of plates were streaked on GM17 plates containing 1 µg/ml Em and 160 µg/ml X-gal. All colonies appearing after this streaking were homogeneous and blue. Plasmid DNA extractions from transformants revealed no detectable extrachromosomally plasmid DNA in the bacterial cell. This strongly indicated that the plasmids pSMA501 and pSMA502 had become integrated into the chromosome of the recipient strains. In FIG. 18 is illustrated the Campbell-like integration of the non-replicating plasmids.

In order to study the stability of the integrated plasmids, both types of integrants were grown in the absence of Em selection for about 20 generations. Suitable dilutions of the resulting culture were plated on GM17 plates with X-gal and subsequently replicated to selective plates, GM17 +X-gal+1 µg/ml Em. In this plate assay no loss of β-galactosidase activity and Em resistance was detected.

(iv) Analysis of regulated β-galactosidase expression on Lactococcus strains harbouring integrable vectors on the chromosome The following experiments was performed to analyze if the expression of β-galactosidase is regulated in strain MG1363 harbouring chromosomally integrated pSMA501 (strain MG1363::pSMA501) and strain MG1614 harbouring chromosomally integrated pSMA502 (strain MG1614::pSMA502).

Six randomly picked reisolates of strain MG1363::pSMA501 were streaked on GM17 plates (1.2× M17-agar and 0.5 % glucose) and on ArgM17 plates (1.2× M17-agar, 0.1% glucose and 0.1% arginine). Both types of plates contained 1 µg/ml Em and 160 µg/ml X-gal. Isolates No. 6, 9, 10, 14 and 21 were all blue on GM17 plates and white on ArgM17 plates. This result shows that the β-galactosidase expression in these isolates, like in Integrant 170 (see Example 7), are still regulated in a pH dependent manner. Isolate No. 3 was blue on GM17 plates and pale blue on ArgM17 plates. The higher level of β-galactosidase expression of this isolate on both types of plates is possibly a consequence of the integration of several copies of the integrable vector into the chromosome or of an amplification of the non-tandem repeated chromosomal DNA sequence.

Eight randomly picked reisolates of strain MG1614::pSMA502 were streaked on GM17 plates and on ArgM17 plates. Both types of plates contained 1 µg/ml Em and 160 µg/ml X-gal. All isolates of strain MG1614::pSMA502, i.e. isolates no. 7, 8, 10, 13, 14, 17, 18, and 22 were blue on GM17 plates and slightly more blue on ArgM17 plates. This result indicated at least a certain level of pH dependent β-galactosidase expression in the strain MG1614::pSMA502. However, in this plate assay it was not possible to compare the levels of β-galactosidase expression and hence the tightness of regulation in strain MG1614::pSMA502 and Integrant SB.

In Examples 7 and 11, the media consisting of 1.5×M17 supplemented with 0.5% glucose and 1.5×M17 supplemented with 0.1%glucose and 0.1% arginine were referred to as G1.5M17 and Arg1.5M17, respectively. In the following these media are designated GM17 and ArgM17, respectively.

The activity of β-galactosidase were measured in cultures grown for 17–18 hrs at 30° C. in GM17 medium (pH 5.6 after growth) and in ArgM17 medium (pH 6.7 after growth), respectpectively. Both GM17 medium and ArgM17medium contained 1 µg/ml erythromycin. Three reisolates of strain MG1363::pSMA501 and two reisolates of strain MG1614::pSMA502 were each assayed for β-galactosidase activity. As a control of regulated β-galactosidase expression, the Integrants 170 and SB, respectively were included in the experiment. The results are shown in Tables 15a and 15b below:

TABLE 15a

β-galactosidase activity of MG1363::pSMA501

| Strain | Miller units in GM17 medium | Miller units in ArgM17 medium | Ratio of Miller units in GM17 vs ArgM17 |
|---|---|---|---|
| Integrant 170 | 1.9 | 0.1 | 19 |
| MG1363::pSMA501, Isolate No. 3 | 23.0 | 1.2 | 19 |
| MG1363::pSMA501, Isolate No. 6 | 7.0 | 0.3 | 23 |
| MG1363::pSMA501, Isolate No. 21 | 2.6 | 0.2 | 13 |

TABLE 15b

β-galactosidase activity of MG1614::pSMA502

| Strain | Miller units in GM17 medium | Miller units in ArgM17 medium | Ratio of Miller units in ArgM17 vs GM17 |
|---|---|---|---|
| Integrant SB | 6.4 | 20.0 | 3.1 |
| MG1614::pSMA502, Isolate No. 8 | 77.0 | 120.0 | 1.6 |
| MG1614::pSMA502, Isolate No. 14 | 64.0 | 99.0 | 1.5 |

It is clearly demonstrated that the expression of the β-galactosidase gene is regulated in all three isolates of strain MG1363::pSMA501. The regulation in each isolate is similar to the regulation observed in Integrant 170. The differences in β-galactosidase activity levels is possibly due to differences in the copy number of pSMA501 on the chromosome. It is, however, difficult to conclude from the results shown in Table 15b, whether there is a regulated or non-regulated β-galactosidase expression in the two isolates of MG1614::pSMA502.

EXAMPLE 16

Transformation of *Lactobacillus helveticus* with pTV32 AND pLTV1

Each of the transposition vectors, pTV32 and pLTV1, was electroporated into *Lactobacillus helveticus* CNRZ32 according to the method described by Bhowmik et al. 1993. The vector pNZ18 (NIZO, BA Ede, The Netherlands), conferring Cm resistance to the host, was also introduced into strain CNZR32 as control of transformation efficiency.

After electroporation, the transformed cells were plated on MRS agar (Oxoid) containing 10 mM CaCl2 and an antibiotic depending on the vector used for transformation. The antibiotic and the concentration used for selection of transformants are given in Table 16 below. Also given in Table 16 are the results from the transformations. A blank space in the Table indicates that this experiment was not performed.

TABLE 16

Transformation of pTV32 and pLTV1 into *Lactobacillus helveticus* CNRZ 32

| | Transformants per µg plasmid | | | |
|---|---|---|---|---|
| | pTV32 | pLTV1 | pNZ18 | no plasmid |
| Antibiotic, concentration | | | | |
| Tetracycline, 20 µg/ml | | 0 | | 0 |
| Chloramphenicol, 10 µg/ml | 0 | 0 | 0 | 0 |
| Erythromycin, 10 µg/ml | 130 | 140 | | 0 |

10 pTV32 transformants and 10 pLTV1 transformants were streaked on MRS agar containing 10 µg/ml Em. A reisolated colony from each of the 20 transformants was inoculated in MRS broth (Oxoid) containing 5 µg/ml Em and plasmid extraction was performed according to O'Sullivan et al. 1993. The plasmid extraction preparations were digested with EcoRI and then subjected to an agarose gel electrophoresis analysis.

No plasmid DNA was detected in any of these plasmid extractions. As it appears from the above Table, 130 and 140 transformants, respectively were obtained per µg of plasmid DNA in which transformants erythromycin resistance was expressed the only conclusion which can be drawn from the fact that plasmid DNA was not detected in any of the tested transformants expressing the erythromycin resistance is that the DNA introduced into the transformants had become integrated in the *Lactobacillus helveticus* chromosome.

The above results therefore provides a strong indication that the above Tn917 derivatives can be used in accordance with the invention also in Lactobacillus spp.

REFERENCES

1. Alexieva, Z., E. J. Duvall, N. P. Ambulos, Jr., U. J. Kim, and P. S. Lovett. 1988. Chloramphenicol induction of cat-86 requires ribosome stalling at a specific site in the regulatory leader. Proc. Nat. Acad. Sci. U.S.A. 85:3057–3061.
2. Beresford, T. and S. Condon. 1993. Physiological and genetic regulation rRNA synthesis in Lactococcus. J. Gen. Microbiol. 139:2009–2017.
3. Berg, C. M., and D. E. Berg. 1987. Uses of transposable elements and maps of known insertions, p. 1071–1109. In F. C. Neidhardt, J. L. Ingraham, K. B. Low, B. Magasanik, M. Schaechter, and H. E. Umbarger (ed.), *Escherichia coli* and *Salmonella typhimurium* cellular and molecular biology. American Society for Microbiology, Washington, D.C.
4. Berg, C. M., D. E. Berg, and E. A. Groisman. 1989. Transposable elements and the genetic engineering of bacteria, p. 879–925. In D. E. Berg and M. M. Howe (ed.), Mobile DNA. American Society for Microbiology, Washington, D.C.
5. Bhowmik, T. and J. L. Steele. 1993. Development of an electroporation procedure for gene disruption in *Lactobacillus helveticus* CNRZ 32. J. Gen. Microbiol 139:1433–1439]
6. Birnboim, H. C., and J. Doly. 1979. A rapid alkaline extraction procedure for screening recombinant plasmid DNA. Nucleic Acids Res. 7:1513–1523.
7. Boe, L., T. T. Nielsen, S. M. Madsen, L. Andrup, and G. Bolander. 1991. Cloning and characterization of two plasmids from *Bacillus thuringiensis* in *Bacillus subtilis*. Plasmid 25:190–197.
8. Bohall, Jr., N. A., and P. S. Vary. 1986. Transposition of Tn917 in *Bacillus megaterium*. J. Bacteriol. 167:716–718.
9. Bojovic, B., G. Djordjevic, and L. Topisirovic. 1991. Improved vector for promoter screening in Lactococci. Appl. Environ. Microbiol. 57:385–388.
10. Camilli, A., D. A. Portnoy, and P. Youngman. 1990. Insertional mutagenesis of Listeria monocytogenes with a novel Tn917 derivative that allows direct cloning of DNA flanking transposon insertions. J. Bacteriol. 172:3738–3744.
11. Chiaruttini, C. and M. Milet. 1993. Gene organization, primary structure and RNA processing analysis of a ribosomal RNA operon in *Lactococcus lactis*. J. Mol. Biol. 230:57–76.
12. Chopin M.-C., A. Chopin, A. Rouault, and N. Galleron. 1989. Insertion and amplification of foreign genes in the *Lactococcus lactis* subsp. *lactis* chromosome. Appl. Environ. Microbiol. 55:1769–1774.
13. David, S., H. Stevens, M. van Riel, G. Simons and W. M. de Vos. 1992. Leuconostoc lactis β-galactosidase is encoded by two overlapping genes. J. Bacteriol. 174:4475–4481.
14. De Vos, W. M., and G. Simons. 1988. Molecular cloning of lactose genes in dairy lactic streptococci: the phospho-β-galactosidase and β-galactosidase genes and their expression products. Biochimie 70:461–473.
15. Froseth, B. R., and L. L. McKay. 1991. Molecular characterization of the nisin resistance region of *Lactococcus lactis* subsp. *lactis* biovar diacetylactis DRC3. Appl. Environ. Microbiol. 57:804–811.
16. Gasson, M. J. 1983. Plasmid complements of *Streptococcus lactis* NCDO 712 and other lactic streptococci after protoplast-induced curing. J. Bacteriol. 154:1–9.
17. Gasson, M. J., and F. L. Davies. 1984. The genetics of dairy lactic acid bacteria, p.99–126. In F. L. Davies and B. A. Law (ed.), Advances in the microbiology and biochemistry of cheese and fermented milk. Elsevier Applied Science Publishers Ltd., London.
18. Hanahan, D. 1983. Studies on transformation of *Escherichia coli* with plasmids. J. Molec. Biol. 166:557–580.
19. Henkin, T. M., C. E. Donnelly, and A. L. Sonenshein. 1988. Mutations in the spacer region of a *Bacillus subtilis* promoter. In Genetics and Biotechnology of bacilli Vol. 2 (Ganesan, A. T. & Hoch, J. A., eds.), pp. 63–67, Academic Press, San Diego.
20. Holo H., and I. F. Nes. 1989. High-frequency transformation, by electroporation, of *Lactococcus lactis* subsp. *cremoris* grown with glycine in osmotically stabilized media. Appl. Environ. Microbiol. 55:3119–3123.
21. Israelsen, H. and E. B. Hansen. 1993. Insertion of transposon Tn917 derivatives into the *Lactococcus lactis* subsp. *lactis* chromosome. Appl. Environ. Microbiol. 59: 21–26.
22. Jahns, A., A. Schafer, A. Geiss and M. Teuber. 1991. Identification, cloning and sequencing of the replication region of *Lactococcus lactis* subsp. *lactis* biovar. diacetylactis Bu2 citrate plasmid pSL2. FEMS Microbiol. Lett. 80:253–258.
23. Jinks-Robertson, S. and M. Nomura. 1987. Ribosomes and tRNA. In *Escherichia coli* and *Salmonella typhimurium*. Cellular and Molecular Biology (Neidhardt, F. C., ed), pp. 1358–1385, American Society for Microbiology, Washington, D.C.
24. Johansen, E., and A. Kibenich. 1992. Characterization of *Leuconostoc isolates* from commercial mixed strain mesophilic starter cultures. J. Dairy Sci. 75:1186–1191.
25. Johansen, E. and A. Kibenich 1992a. Isolation and characterization of IS1165, an insertion sequence of *Leu-*

*conostoc mesenteroides* subsp. *cremoris* and other lactic acid bacteria. Plasmid 27:200–206.

26. Kiewiet, R., J. Kok, J. F. M. L. Seegers, G. Venema and S. Bron. 1993. The mode of replication is a major factor in segregational plasmid instability in *Lactococcus lactis*. Appl. Environ. Microbiol. 59:358–364.
27. Klaenhammer, T. R. 1988. Bacteriocins of lactic acid bacteria. Biochimie 70:337–349.
28. Koivula, T., M. Sibakov, and I. Palva. 1991. Isolation and characterization of *Lactococcus lactis* subsp. *lactis* promoters. Appl. Environ. Microbiol. 57:333–340.
29. Kok, J. 1990. Genetics of the proteolytic system of lactic acid bacteria. FEMS Microbiol. Reviews 87:15–42.
30. Kok, J., M. B. M. van der Vossen, and G. Venema. 1984. Construction of plasmid cloning vectors for lactic streptococci which also replicate in *Bacillus subtilis* and *Escherichia coli*. Appl. Environ. Microbiol. 48:726–731.
31. Le Bourgeois, P., M. Mata, and P. Ritzenthaler. 1989. Genome comparison of Lactococcus strains by pulsed-field gel electrophoresis. FEMS Microbiol. Lett. 59:65–70.
32. Leenhouts K. J., J. Kok and G. Venema. 1989. Campbell-like integration of heterologous plasmid DNA into the chromosome of *Lactococcus lactis* subsp. *lactis*. Appl. Environ. Microbiol. 55:394–400.
33. Macrina, F. L., R. P. Jones, J. A. Tobian, D. L. Hartley, D. B. Clewell and K. R. Jones 1983. Novel shuttle plasmid vehicles for Escherichia-Streptococcus transgeneric cloning. Gene 25:145–150.
34. Maniatis, T., E. F. Fritsch, and J. Sambrook. 1982. Molecular cloning: a laboratory manual. Cold Spring Harbor Laboratory, Cold Spring Harbor, N.Y.
35. Marsh, J. L., M. Erfle and E. J. Wykes. 1984. The pIC plasmid and phage vectors with versatile cloning sites for recombinant selection by insertional inactivation. Gene 32:481–485.
36. Mayo, B., J. Kok, K. Venema, W. Bockelmann, M. Teuber, H. Reinke, and G. Venema. 1991. Molecular cloning and sequence analysis of the X-prolyl dipeptidyl aminopeptidase gene from *Lactococcus lactis* subsp. *cremoris*. Appl. Environ. Microbiol. 57:38–44.
37. Miller, J. H. 1972. Experiments in Molecular Genetics. Cold Spring Harbor Laboratory, Cold Spring Harbor, N.Y.
38. Nardi, M., M.-C. Chopin, A. Chopin, M.-M. Cals, and J.-C. Gripon. 1991. Cloning and DNA sequence analysis of an X-prolyl dipeptidyl aminopeptidase gene from *Lactococcus lactis* subsp. *lactis* NCDO 763. Appl. Environ. Microbiol. 57:45–50.
39. Nilsson, D. and A. A. Lauridsen. 1992. Isolation of purine auxotrophic mutants of *Lactococcus lactis* and characterization of the gene hpt encoding hypoxanthine guanine phosphoribosyltransferase. Mol. Gen. Genet. 235:359–364.
40. Nygaard, P. 1983. Utilization of preformed purine bases and nucleosides. In Munch-Petersen, A. (ed), Metabolism of nucleotides, nucleosides and nucleobases in microorganisms. Academic Press, Inc., New York, pp 27–93.
41. Ochman, H. et al. 1988. Genetics applications of an inverse polymerase chain reaction. Genetics 120:621–625.
42. Ogasawara, N., S. Moriya and H. Yoshikawa. 1983. Structure and organization of rRNA operons in the region of the replication origin of the *Bacillus subtilis* chromosome. Nucleic acids Res. 11:6301–6318.
43. O'Sullivan, D. J. and T. R Klaenhammer. 1993. Rapid Mini-Prep Isolation of high-quality plasmid DNA from Lactococcus and Lactobacillus spp. Appl. Environ. Microbiol. 59:2730–2733.
44. Pedersen, M. L., K. R. Arnved and E. Johansen. 1993. Genetic analysis of the minimal replicon of the *Lactococcus lactis* subsp. *lactis* biovar diacetylactis citrate plasmid. J. Bacteriol: submitted for publication.
45. Perkins, J. B., and P. J. Youngman. 1984. A physical and functional analysis of Tn917, a Streptococcus transposon in the Tn3 family that functions in Bacillus. Plasmid. 12:119–138.
46. Romero, D. A. and T. R. Klaenhammer. 1992. IS946-Mediated integration of heterologous DNA into the genome of *Lactococcus lactis* subsp. *lactis*. Appl. Environ. Microbiol. 58:699–702.
47. Sanders, M. E. 1988. Phage resistance in lactic acid bacteria. Biochimie 70:411–421.
48. Sanders, M. E., and M. A. Nicholson. 1987. A method for genetic transformation of nonprotoplasted *Streptococcus lactis*. Appl. Environ. Microbiol. 53:1730–1736.
49. Shaw, J. H., and D. B. Clewell. 1985. Complete nucleotide sequence of macrolide-lincosamide-streptogramin B-resistance transposon Tn917 in *Streptococcus faecalis*. J. Bacteriol. 164:782–796.
50. Simons, G., H. Buys, E. Koenhen and W. M. De Vos. 1990. Construction of a promoter-probe vector for lactic acid bacteria using the lacG gene of *Lactococcus lactis*. In: Developments in Industrial Microbiology, Supplementum 5, 31:31–39.
51. Tomich, P. K., F. Y. An, and D. B. Clewell. 1980. Properties of erythromycin-inducible transposon Tn917 in *Streptococcus faecalis*. J. Bacteriol. 141:1366–1374.
52. Tanskanen, E. I., D. L. Tulloch, A. J. Hillier, and B. E. Davidson. 1990. Pulsed-field gel electrophoresis of SmaI digests of lactococcal genomic DNA, a novel method of strain identification. Appl. Environ. Microbiol. 56:3105–3111.
53. van Belkum, M. J., B. J. Hayema, R. E. Jeeninga, J. Kok, and G. Venema. 1991. Organization and nucleotide sequences of two lactococcal bacteriocin operons. Appl. Environ. Microbiol. 57:492–498.
54. Vandeyar, M. A., and S. A. Zahler. 1986. Chromosomal insertions of Tn917 in *Bacillus subtilis*. J. Bacteriol. 167:530–534.
55. Youngman, P. J. 1987. Plasmid vectors for recovering and exploiting Tn917 transpositions in Bacillus and other gram-positives, p. 79–103. In K. Hardy (ed.), Plasmids: a practical approach. IRL Press, Oxford.
56. Youngman, P., H. Poth, B. Green, K. York, G. Olmedo, and K. Smith. 1989. Methods for genetic manipulation, cloning and functional analysis of sporulation genes in *Bacillus subtiis*, p. 65–87. In I. Smith, R. A. Slepecky, and P. Setlow (ed.), Regulation of procaryotic development. American Society for Microbiology, Washington, D.C.
57. Youngman, P. J., J. B. Perkins, and R. Losick. 1983. Genetic transposition and insertional mutagenesis in *Bacillus subtilis* with *Streptococcus faecalis* transposon Tn917. Proc. Natl. Acad. Sci. 80:2305–2309.
58. Youngman, P., P. Zuber, J. B. Perkins, K. Sandman, M. Igo, and R. Losick. 1985. New ways to study developmental genes in spore-forming bacteria. Science 228:285–291.
59. van der Vossen, J. M. B. M., D. van der Lelie and G. Venema. 1987. Isolation and characterization of *Lactococcus lactis* subsp. *cremoris* Wg2-specific promoters. Appl. Environ. Microbiol. 53:2452–2457.
60. van der Vossen, J. M. B. M., J. Kok and G. Venema. 1985. Construction of cloning, promoter-screening, and terminator-screening shuttle vectors for *Bacillus subtilis* and *Lactococcus lactis* subsp. *lactis*. Appl. Environ. Microbiol. 50:540–542.

We claim:

1. A method of isolating a lactic acid bacterial DNA fragment comprising a promoter, the method comprising the steps of:

(i) selecting a DNA molecule replicating in a lactic acid bacterium, said molecule comprising (a) a transposable element comprising a promoterless structural gene as a promoter probe gene, (b) a detectable selective marker gene, and (c) an origin of replication which is functional in lactic acid bacteria, (ii) introducing the DNA molecule into a population of a lactic acid bacterium, followed by subjecting the population to conditions allowing transposition of the transposable element to occur, (iii) selecting a cell of the lactic acid bacterial population in which the promoterless gene is expressed, (iv) cloning said cell and isolating from the clone a DNA fragment comprising a lactic acid bacterial promoter being operably linked to the originally promoterless gene.

2. The method according to claim 1 which further comprises isolating from the DNA fragment isolated in step (iv) a lactic acid bacterial DNA subfragment comprising the promoter.

3. The method according to claim 1 wherein the transposable element is one which becomes at least quasi-randomly integrated into a lactic acid bacterial replicon.

4. The method according to claim 3 wherein the lactic acid bacterial replicon is a chromosome.

5. The method according to claim 1 wherein the transposable element is a transposon Tn917.

6. The method according to claim 1 wherein the DNA molecule of step (i) is a pTV plasmid.

7. The method according to claim 6 wherein the DNA molecule is selected from the group consisting of pTV32 and pLTV1.

8. The method according to claim 1 wherein the promoterless structural gene is selected from a gene coding for a gene product conferring antibiotic resistance, a gene coding for a gene product complementing an auxotrophic deficiency and a gene coding for an enzyme having a detectable end product.

9. The method according to claim 8 wherein the promoterless structural gene is a β-galactosidase-encoding gene.

10. The method according to claim 1 wherein the population of lactic acid bacteria into which the DNA molecule is introduced are selected from the group consisting of Lactococcus spp., Streptococcus spp., Lactobacillus spp., Leuconostoc spp., Pediococcus spp., Brevibacterium spp., Propionibacterium spp. and Bifidobacterium spp.

11. The method according to claim 10 wherein the population of lactic acid bacteria is from *Lactococcus lactis*.

12. The method according to claim 11 wherein the population of lactic acid bacterium is a *Lactococcus lactis* subspecies *lactis* strain selected from the group consisting of strain MG1614 and strain MG1363.

13. The method according to claim 1 wherein the promoter is a regulatable promoter.

14. The method according to claim 13 wherein the regulatable promoter is regulatable by a factor selected from pH, growth temperature, a temperature shift eliciting expression of heat shock genes, composition of growth medium including ionic strength/NaCl content and the presence/absence of purine nucleotide precursors, and the growth phase/growth rate of the lactic acid bacterium into which the promoter-comprising DNA molecule is introduced.

15. A method of constructing a recombinant lactic acid bacterium comprising the steps of:

(i) isolating in accordance with the method of claim 1 a DNA fragment comprising a regulatable lactic acid bacterial promoter, (ii) inserting the isolated fragment comprising the promoter into a lactic acid bacterium upstream of a gene coding for a desired gene product, the inserted promoter thereby becoming operably linked to said gene.

16. A method of constructing a recombinant lactic acid bacterium comprising the steps of:

(i) isolating in accordance with the method of claim 1 a DNA fragment comprising a regulatable lactic acid bacterial promoter, (ii) inserting into a lactic acid bacterium a gene coding for a desired gene product, (iii) inserting the isolated fragment comprising the promoter into the lactic acid bacterium resulting from step (ii) upstream of the gene coding for a desired gene product, the inserted promoter thereby becoming operably linked to said gene.

17. The method according to claim 16 wherein the inserted gene coding for a desired gene product is a heterologous gene.

18. The method according to claim 16, wherein the inserted gene is a lactic acid bacterial gene.

19. The method according to claim 16 wherein the gene coding for a desired gene product is inserted on the same DNA fragment as the isolated fragment comprising the promoter.

20. The method according to claim 15 or 16 wherein the isolated fragment comprising the promoter is inserted into a chromosome of a lactic acid bacterial bacterium.

21. The method according to claim 15 or 16 wherein the isolated fragment comprising the promoter is inserted extrachromosomally.

22. The method according to claim 15 or 16 wherein the isolated fragment comprising the promoter comprises a further DNA fragment whereby the isolated promoter becomes regulated by a stochastic event selected from recombinational excision of the promoter, recombinational excision of a gene coding for a product which is positively needed for the promoter function and recombinational excision of a regulatory DNA fragment inhibiting the function of the promoter.

23. The method according to claim 22 wherein the further fragment results in recombinational excision of a regulatory sequence inhibiting the function of the promoter.

24. A method of constructing a recombinant lactic acid bacterium comprising the steps of:
(i) selecting a DNA molecule replicating in a lactic acid bacterium, said molecule comprising a transposable element comprising a promoterless structural gene as a promoter probe gene, (b) a detectable selective marker gene, and (c) an origin of replication which is functional in a lactic acid bacterium,
(ii) introducing under conditions allowing transposition of the transposable element to occur, the DNA molecule of step (i) into a population of a lactic acid bacterium,
(iii) selecting a cell of the lactic acid bacterial population in which the promoterless structural gene is regulatably expressed as a result of being operably linked to a regulatable native promoter of the lactic acid bacterial cell,
(iv) identifying the site(s) in a replicon of the lactic acid bacterial cell of step (iii) into which the transposable element is integratable, and
(v) inserting into a non-integrant cell of the lactic acid bacterial population a gene coding for a desired gene product at a site in a replicon as identified in step (iv) or at a functionally equivalent site, whereby the gene becomes operably linked to said native lactic acid bacterial promoter,
the expression of the inserted gene hereby being altered as compared to the expression of the gene when operably linked to its native promoter.

25. The method according to claim 24 wherein the gene coding for a desired gene product is a heterologous gene.

26. The method according to claim 25 wherein the gene is derived from a lactic acid bacterium.

27. The method according to claim 24 wherein the DNA molecule of step (i) is transposed into the chromosome of the lactic acid bacterial bacterium.

28. The method according to claim 24 wherein the DNA molecule of step (i) is transposed into an extrachromosomal replicon.

29. Recombinant lactic acid bacterium comprising a gene coding for a desired gene product and operably linked thereto a regulated promoter not natively associated with the gene, said promoter being of lactic acid bacterial origin and being regulated by a factor selected from the group consisting of pH, growth temperature, temperature shift eliciting the expression of heat shock genes, the composition of the growth medium including the ionic strength, NaCl content, presence or absence of purine nucleotide precursors, the growth phase and growth rate of the bacteria, and a stochastic event, the presence of said promoter resulting in the expression of the gene being altered as compared to the expression of the gene when operably linked to its native promoter.

30. The bacterium according to claim 29 in which the gene coding for a desired gene product is expressed at a level which is at least 10% different from the level at which the gene is naturally expressed.

31. The lactic acid bacterium according to claim 30 in which the gene coding for a desired gene product is expressed at a level which is at least 25% different from the rate at which the gene is naturally expressed.

32. The bacterium according to claim 29 in which the gene coding for a desired gene product is a chromosomal gene.

33. The bacterium according to claim 32 in which the promoter is isolated from Lactococcus spp., Streptococcus spp., Lactobacillus spp., Leuconostac spp., Pediococcus spp., Brevibacterium spp., Propionibacterium spp. or Bifidobacterium spp.

34. The bacterium according to claim 33 wherein the promoter is isolated from the *Lactococcus lactis.*

35. The bacterium according to claim 34 wherein the promoter is a promoter isolated from strain MG1614 or strain MG1363.

36. The bacterium according to claim 29 in which the gene coding for a desired gene product is an extrachromosomal gene.

37. The bacterium according to claim 29 in which the gene coding for a desired gene product is a native gene.

38. The bacterium according to claim 29 in which the gene coding for a desired gene product is a heterologous gene.

39. The bacterium according to claim 38 in which the heterologous gene is derived from a lactic acid bacterium.

40. The bacterium according to claim 29, in which the isolated sequence comprising the promoter further comprises a sequence whereby the promoter becomes regulated by a stochastic event.

41. The bacterium according to claim 40 in which the further sequence results in recombinational excision of a regulatory sequence inhibiting the function of the promoter.

42. The bacterium according to claim 29 in which the promoter is located on a plasmid having run-away behaviour.

43. The bacterium according to claim 29 which is one selected from the group consisting of Lactococcus spp., Streptococcus spp., Lactobacillus spp., Leuconostoc spp., Pediococcus spp., Brevibacterium spp., Propionibacterium spp. and Bifidobacterium spp.

44. The bacterium according to claim 29 in which a gene coding for a desired gene product is inserted at a site in a replicon where it is under the control of a promoter present in the replicon, which site is identifiable by the insertion of a promoterless structural gene by means of a transposable element comprising the promoterless structural gene whereby the originally promoterless gene becomes expressible by being operably linked to the promoter present in said replicon, the insertion of the gene at said site having resulted in said gene becoming operably linked to the promoter being present in the replicon.

45. The bacterium according to claim 44 wherein the inserted gene is isolated from a lactic acid bacterium.

46. The bacterium according to claim 44 wherein the gene is inserted into a chromosome of the lactic acid bacterium.

47. A bacterium according to claim 44 wherein the gene is inserted into an extrachromosomal replicon.

48. The bacterium according to claim 44 in which the inserted gene is a homologous gene.

49. The bacterium according to claim 44 in which the inserted gene is a heterologous gene.

50. The bacterium according to claim 49 in which the inserted heterologous gene is derived from a lactic acid bacterium.

51. The bacterium according to claim 29 or 44 in which the gene coding for a desired gene product is selected from the group consisting of a gene coding for a lipase, a gene coding for a peptidase, a gene coding for a protease, a gene coding for a gene product involved in carbohydrate metabolism, a gene coding for a gene product involved in citrate metabolism, a gene coding for a gene product involved in purine metabolism, a gene coding for a gene product involved in bacteriophage resistance, a gene coding for a lytic enzyme and a gene coding for a bacteriocin.

52. The bacterium according to claim 51 in which the gene coding for a desired gene product is selected from the group consisting of a lacL gene of a Leuconostoc spp, a lacM gene of a Leuconostoc spp. and a *Lactococcus lactis* ssp *lactis* gene coding for a lysine aminopeptidase.

53. The bacterium according to claim 29 wherein the regulatable promoter is a promoter selected from the group consisting of a lactic acidbacterial tRNA promoter, rRNA promoter, purD promoter and a promoter comprising the motif AGTT.

54. The bacterium according to claim 29 in which the regulatable lactic acid bacterial promoter is inserted into a vector comprising a promoterless gene coding for a desired gene product, a theta-replicating lactic acid bacterial replicon which is functional in the bacterium, an insertion site allowing the DNA sequence to be inserted so that the gene coding for the desired gene product is operably linked to the promoter, whereby the gene is transcribed.

55. The bacterium according to claim 54 in which the vector is the plasmid pAK80 as deposited under the accession number DSM 8496.

56. An isolated DNA fragment, comprising a regulated promoter of lactic acid bacterial origin, which pormoter is functional in lactic acid bacteria and operably linked thereto a gene coding for a desired gene product, said promoter being one which is not naturally associated with the gene and being regulated by a factor selected from the group consisting of pH, growth temperature, temperature shift eliciting expression of heat shock genes, composition of the growth medium including ionic sttength, NaCl content and the presence of absence of puring nucleotide precursors, the grouth phase and rate of the bacteria, and a stochastic event.

57. The DNA fragment according to claim 56 which further comprises at least one transcription terminator.

58. The DNA fragment according to claim 56 which is a DNA fragment having a size which is in the range of 100 to 10000 base pairs.

59. The DNA fragment according to claim 56 which is a fragment having a size which is in the range of 200 to 5000 base pairs.

60. The DNA fragment according to claim 56 which further comprises sequences coding for gene products involved in regulation of the promoter.

61. The DNA fragment according to claim 56 in which the gene coding for a desired gene product is one selected from the group consisting of a gene coding for a lipase, a gene coding for a peptidase, a gene coding for a protease, a gene coding for a gene product involved in carbohydrate metabolism, a gene coding for a gene product involved in citrate metabolism, a gene coding for a gene product involved in purine metabolism, a gene coding for a gene product involved in bacteriophage resistance, a gene coding for a lytic enzyme and a gene coding for a bacteriocin.

62. The DNA fragment according to claim 56 in which the gene coding for a desired gene product is a heterologous gene.

63. The DNA fragment according to claim 56 in which the gene is a gene isolated from a lactic acid bacterium.

64. The DNA fragment according to claim 63 in which the gene coding for a desired gene products is one selected from a lacL gene of a Leuconostoc spp., the lacM gene of a Leuconostoc spp. and a *Lactococcus lactis* spp. *lactis* gene coding for a lysine aminopeptidase.

65. The isolated DNA fragment according to claim 56, wherein said lactic acid regulated promoter is the regulatable promoter contained in the *Lactococcus lactis* ssp. *lactis* MG1363 integrant clone P139-170 deposited under accession number DSM 7360, said DNA fragment having a size in the range of 100 to 10,000 base pairs, and said gene product is selected from the group encoding a lipase, a peptidase and protease, a gene product involved in carbohydrate metabolism, a gene product involved in citrate metabolism, a gene product involved in purine metabolism, a gene product involved in bacteriophage resistance, a lytic enzyme and bacteriocin.

66. The isolated DNA fragment according to claim 56, wherein said lactic acid regulated bacterial promoter is the regulatable promoter contained in the *Lactococcus lactis* ssp. *lactis* MG1614 integrant clone 63b deposited under accession number DSM 7361, said DNA fragment having a size in the range of 100 to 10,000 base pairs, and said gene product is selected from the group encoding a lipase, a peptidase, a protease, a gene product involved in carbohydrate metabolism, a gene product involved in citrate metabolism, a gene product involved in citrate metabolism, a gene product involved in purine metabolism, a gene product involved in bacteriophage resistance, a lytic enzyme, and bacteriocin.

67. A recombinant plasmid comprising (i) a vector comprising a promoterless gene coding for a desired gene product, (ii) a theta-replicating lactic acid bacterial replicon which is functional in a lactic acid bacterium and (iii) an insertion site allowing a DNA sequence to be inserted, and (iv) inserted into said insertion site a DNA sequence comprising a regulatable lactic acid bacterial promoter, the insertion resulting in that the gene coding for the desired gene product is operably linked to the promoter, whereby the gene is transcribed.

68. The plasmid according to claim 67 in which the vector is pAK80.

69. The plasmid according to claim 67 wherein the regulatable promoter being inserted is a strong promoter selected from the group consisting of a lactic acid bacterial tRNA promoter, rRNA promoter, purD promoter and a promoter comprising the motif AGTT.

70. Recombinant lactic acid bacteria, comprising a gene encoding a desired gene product and operably linked to a lactic acid bacterial regulatable promoter not naturally associated with said gene, the presence of said promoter resulting in the expression of the gene being altered as compared to the expression of the gene when operably linked to its natural promoter, wherein said regulatable lactic acid promoter is inserted into the plasmid pAK80 into which is also inserted a promoterless gene encoding said gene product, a theta-replicating lactic acid bacterial replicon, an insertion site allowing the DNA sequence to be inserted so that sad gene encoding a gene product is operably linked to said promoter, whereby the gene is transcribed.

71. A pAK80 recombinant plasmid comprising (1) a vector comprising a promoterless gene coding for a desired gene product, (ii) a theta-replicating lactic acid bacterial replicon which is functional in a lactic acid bacterium and (iii) an insertion site allowing a DNA sequence to be inserted, and (iv) regulatable lactic acid bacterial promoter, the insertion resulting in that the gene coding for the desired gene product is operably linked to the promoter, whereby the gene is transcribed.

* * * * *

UNITED STATES PATENT AND TRADEMARK OFFICE
CERTIFICATE OF CORRECTION

PATENT NO. : 5,837,509
DATED : November 17, 1998
INVENTOR(S) : Hans ISRAELSEN et al.

It is certified that error appears in the above-identified patent and that said Letters Patent is hereby corrected as shown below:

Column 81, line 13, Claim 20, replace "the promoter" with --a promoter--;

Column 81, line 13, Claim 20, replace "into a" with --into the--;

Column 83, line 16, Claim 50, replace "derivated" with --isolated--;

Column 83, line 34, Claim 53, replace "regulatable" with --regulated--;

Column 83, line 39, Claim 54, replace "regulatable" with --regulated--;

Column 83, line 39, Claim 54, delete "lactic acid bacterial";

UNITED STATES PATENT AND TRADEMARK OFFICE
CERTIFICATE OF CORRECTION

PATENT NO. : 5,837,509                    Page 2 of 3
DATED      : November 17, 1998
INVENTOR(S): Hans ISRAELSEN et al.

It is certified that error appears in the above-identified patent and that said Letters Patent is hereby corrected as shown below:

Column 83, line 50, Claim 56, replace "pormoter" with --promoter--;
Column 83, line 58, Claim 56, replace "puring" with --purine--;
Column 83, line 59, Claim 56, replace "grouth" with --growth--;
Column 83, line 59, Claim 56, after, phase and, insert --growth--;
Column 83, line 65, Claim 59, replace "claim 56" with --claim 58--;
Column 84, line 55, Claim 67, replace "a regulatable lactic acid bacterial promoter" with --a regulated promoter derived from a lactic acid bacterial species";
Column 84, line 62, Claim 69, replace "regulatable" with --regulated--;

UNITED STATES PATENT AND TRADEMARK OFFICE
CERTIFICATE OF CORRECTION

PATENT NO. : 5,837,509
DATED : November 17, 1998
INVENTOR(S) : Hans ISRAELSEN et al.

It is certified that error appears in the above-identified patent and that said Letters Patent is hereby corrected as shown below:

Column 86, line 1, Claim 71, replace "(1)" with --(i)--.

On the Title page, Item No. [21] PCT Filed, should correctly read --January 3, 1994--, also Item No. [56] References Cited, Other Publications, insert --Romero et al., Journal of Bacteriology, Vol. 173, No. 23, pp.7599-7606 (1991).

Signed and Sealed this

Twenty-fourth Day of August, 1999

Q. TODD DICKINSON

*Attest:*

*Attesting Officer*          *Acting Commissioner of Patents and Trademarks*